US005256625A

United States Patent [19]

Bussler et al.

[11] Patent Number: 5,256,625

[45] Date of Patent: Oct. 26, 1993

[54] SAFENING IMIDAZOLINONE HERBICIDES

[75] Inventors: Brett H. Bussler, St. Louis Park, Minn.; Ronald J. Brinker, Ellisville, Mo.

[73] Assignee: Monsanto Company, St. Louis, Mo.

[21] Appl. No.: 459,393

[22] Filed: Dec. 29, 1989

Related U.S. Application Data

[63] Continuation-in-part of Ser. No. 212,621, Jul. 1, 1988, which is a continuation-in-part of Ser. No. 84,786, Aug. 13, 1987, abandoned.

[51] Int. Cl.[5] .................. A01N 25/32; A01N 43/50

[52] U.S. Cl. .................. 504/107; 504/105; 504/108; 504/253

[58] Field of Search .................. 71/88, 92; 504/107, 504/108, 253

[56] References Cited

U.S. PATENT DOCUMENTS

| | | | |
|---|---|---|---|
| 4,197,110 | 4/1980 | Szabo et al. | 71/88 |
| 4,608,079 | 8/1986 | Los | 71/92 |
| 4,726,835 | 2/1988 | Uemura et al. | 71/92 |
| 4,776,876 | 10/1988 | Nordhoff et al. | 71/92 |
| 4,851,031 | 7/1989 | Bellucci et al. | 71/92 |
| 4,938,796 | 7/1990 | Buren et al. | 71/98 |
| 4,992,092 | 2/1991 | Birk et al. | 71/92 |

FOREIGN PATENT DOCUMENTS 304409 2/1989 European Pat. Off. .

OTHER PUBLICATIONS

"Activity and Pre-Emergence Selectivity of Some Recently Developed Herbicides AC-213087 and AC-222293". W. G. Richardson et al, ARC Weed Res. Organization, Technical Report No. 66, pp. 1-31, Dec. 1982.

"Potential Safeners for Imazaquin" NCWCC Proceedings, vol. 39, pp. 39, 40, 1984 M. Barrett et al.

"Protection of Sorghum from Imidazoline Injury", Plant Physiol. 77, No. 4, Suppl. 55, 1985, M. Barrett et al.

"Protection of Corn (Zea mays) and Sorghum (Sorghum bicolor) from Imazethapyr Toxicity with Antidotes" Weed Science, 1989, vol. 37; 296-301 M. Barrett.

*Primary Examiner*—Richard L. Raymond
*Assistant Examiner*—B. Bembenick
*Attorney, Agent, or Firm*—William I. Andress

[57] ABSTRACT

The disclosure herein relates to the use of certain amides of dichloroacetic acid and other compounds as safener/antidotal compounds to reduce the phytotoxicity to crop plants, especially corn, of imidazolinone-type herbicides alone or in admixture with other co-herbicidal compounds, e.g., α-haloacetamides.

17 Claims, No Drawings

SAFENING IMIDAZOLINONE HERBICIDES

This application is a continuation-in-part of copending U.S. application Ser. No. 07/212,621 filed Jul. 1, 1988, which is a continuation-in-part of U.S. application Ser. No. 084,786, filed Aug. 13, 1987, now abandoned.

FIELD OF THE INVENTION

The field of the invention contemplated herein pertains to the safening of herbicidal compounds with antidotal or safener compounds. Particular herbicides involved are imidazolinone compounds with or without co-herbicidal compounds, e.g., α-haloacetanilides.

BACKGROUND OF THE INVENTION

Many herbicides injure crop plants at herbicide application rates necessary to control weed growth. Accordingly, many herbicides cannot be used for controlling weeds in the presence of certain crops. Uncontrolled weed growth, however, results in lower crop yield and reduced crop quality inasmuch as weeds compete with crops for light, water and soil nutrients. Reduction of herbicidal injury to crops without an unacceptable corresponding reduction of herbicidal action on the weeds can be accomplished by use of crop protectants known as herbicide "antagonists", "antidotes" or "safeners".

Weed control for crops, especially corn crops, is one of the oldest and most highly developed areas in weed science. For a herbicide product to be accepted commercially for corn crops, such herbicide product must provide a relatively high level of control of both grassy and broadleaf weeds in corn, in addition to meeting several other criteria. For example, the herbicide should possess relatively high unit activity so that lower rates of herbicide application are feasible. Lower application rates are desirable in order to minimize exposure of the environment to the herbicide. At the same time, such herbicide must be selective in herbicidal effect so as not to injure the crops. Herbicidal selectivity can be enhanced by use of an appropriate antidote in combination with the herbicide. But identification of an antidote which safens a herbicide in crops is a highly complicated task. Whether a compound or class of compounds provides efficacious antidote or safening activity is not a theoretical determination but must be done empirically. Safening activity is determined empirically by observing the complex interaction of several biological and chemical factors, namely: the type of herbicide compound; the type of weed to be controlled; the type of crop to be protected from weed competition and herbicidal injury; and the antidote compound itself. Moreover, the herbicide and antidote must each possess chemical and physical properties enabling preparation of a stable formulation which is environmentally safe and easy to apply to the field.

Among the various classes of compounds found to be suitable for various herbicidal purposes are the α-haloacetanilides and imidazolinones. The former herbicides, e.g., alachlor, acetochlor, metolachlor, etc., are excellent preemergence or early post emergence herbicides for controlling annual grasses and many broadleaved weeds in corn, peanuts, soybeans and other crops, while some of the latter herbicides, exemplified by imazaguin, imazethapyr, imazapyr AC-222293, and AC-263222, may be used as a foliar—or soil-applied herbicide suitable for the control of many annual and perennial broadleaved species in asparagus, cereals, grain, corn, sorghum, sugarcane and other crops and woody brush and vine control in pasture, rangeland and cropland. Other imidazolinones can be used in preplant or preemergence applications.

It is a common agronomic practice to use various antidotal compounds to reduce the phytotoxicity of some herbicides to various crops. For example, fluorazole (active ingredient in SCREEN® safener) is used as a seed dressing to protect sorghum seed from alachlor (active ingredient in LASSO® herbicide). Similarly, cyometrinil (active ingredient in CONCEP® safener) is a corn seed safener for use with metolachlor and oxabetrinil (active ingredient in CONCEP II safener) is used to safen sorghum seed from injury by metolachlor. The compound N,N-diallyl dichloroacetamide (common name R-25788) is used to safen corn from injury by the thiocarbamate 5-ethyl-N,N-dipropylthiocarbamate (active ingredient in ERADICANE® herbicide) and acetochlor (active ingredient in HARNESS® herbicide).

It is not known to our knowledge to safen imidazolinones when used alone or in combination with other herbicides, especially α-haloacetanilides, as co-herbicides. Accordingly, it is an object of this invention to provide compositions of those herbicides in combination with antidotes therefor, which compositions are useful to reduce injury to crops, especially corn, due to phytotoxicity of said herbicides.

SUMMARY OF THE INVENTION

The present invention relates to herbicidal compositions comprising imidazolinone herbicides and antidotal compounds therefor to reduce injury to various crops, particularly corn, from the phytotoxic effects of said herbicide when used alone or in combination with other compounds, particularly α-haloacetanilides, as co-herbicides.

In more particular, in a major aspect, this invention relates to a composition comprising:

(a) a herbicidal compound having the formula

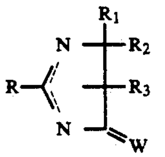
I wherein

R represents one of the radicals

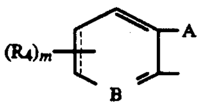
IA

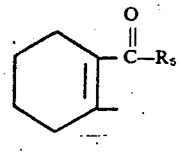
IB or

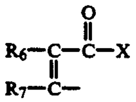
IC wherein in Formulae I and IA, the dashes represent saturation or unsaturation (it being understood that in Formula I when one dashed line represents an unsaturated bond with one N atom, the $R_3$ group will be attached to the other N atom) and in Formula I $R_1$ is H, $C_{1-4}$ alkyl or haloalkyl, $R_2$ is H, $C_{1-6}$ alkyl, $C_{3-6}$ cycloalkyl or cycloalkylmethyl, phenyl, halophenyl, benzyl or $R_1$ and $R_2$ combined form a $C_{3-6}$ cycloalkyl which may be substituted with $C_{1-3}$ $R_3$ is H, $COD_1$ $SOD_2$ or $SO_2D_3$, wherein $D_1$, $D_2$ and $D_3$ are H, $C_{1-10}$ alkyl, halomethyl or phenyl which may be substituted with halogen, $NO_2$ or $C_{1-4}$ alkyl or alkoxy, said $R_3$ being attached to the ring nitrogen atom of the isomer not having a double bond structure; and W is oxygen or sulfur;

where in Formula IA

A is $COOD_4$, $CONHD_5$, $COND_6D_7$, CHO, $CH_2OH$, $COCH_3$, $COC_6H_5$, CN, $CH_3$, CH=NOH, $CH_2COOH$, $CH_2COOD_8$, $CH_2COOH$, CONHOH, $CHD_9OH$,

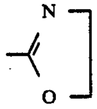

or

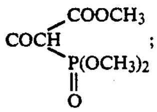

;

$D_4$ is H, diloweralkylimino, $C_{1-12}$ alkyl optionally substituted with $C_{1-3}$ alkoxy, halogen, OH, $C_{3-6}$ cycloalkyl or cycloalkylmethyl; benzyl, benzyloxy, or alkoxy, nitro or carboxyl; furyl, tetrahydrofuryl, dialkylphoshonyl, glycidyl, $COC_{1-4}$ alkoxy, CN, phenyl, $NH(C_{1-4}\ alkyl)_3$, $C_{3-12}$ alkenyl or alkynyl, both optionally substituted with $C_{1-3}$ alkoxy, phenyl, halogen or $COC_{1-4}$ alkoxy; $C_{3-6}$ cycloalkyl or cycloalkylmethyl, both optionally substituted with $C_{1-3}$ alkyl; or a cation selected from alkali and alkaline earth metals, Mn, Sn, Fe, Zn, Co, Pb, Ag, Ni, ammonium and organic ammonium;

$D_5$ is H, OH, $NH_2$, $N(CH_3)_2$, $NHCOCH_3$, $C_6H_5NH_2$, $C_{3-5}$ alkenyl or alkyny or $C_{1-4}$ alkyl optionally substituted with OH or halogen;

$D_6$, $D_7$ and $D_8$ are H, OH or $C_{1-4}$ alkyl;

B is N or CH;

m is 0–3; and $R_4$ is H, halogen, $C_{1-6}$ alkyl, alkoxy, alkylthio, haloalkyl, or hydroxyalkyl; $NO_2$, CN, phenyl or phenoxyl, both optionally substituted with $C_{1-4}$ alkyl, alkoxy or alkoxyalkyl or halogen; $SD_9$ or $OD_{10}$ wherein $D_9$ is H, phenyl or phenyl substituted with halogen, $C_{1-3}$ alkyl or alkoxy or, $NO_2$; pyridyl or $C_{1-3}$ alkyl-substituted pyridyl; $C_{2-8}$ alkyl, alkoxy or polyalkoxy; $C_{3-8}$ cycloalkyl or heterocyclyl containing O, S or N atoms both of which may be substituted with $C_{1-4}$ alkyl, alkoxy or halogen; $C_{5-8}$ cycloalkenyl, and $D_{10}$ is H, $C_{3-8}$ cycloalkyl or heterocyclyl containing O, S or N atoms both of which may be substituted as in $D_8$; or $C_{5-8}$ cycloalkenyl;

when B is N, two $R_4$ radicals may be combined to form a radical having one of the following formulae:

$-(CH=CH)_m-$, where m is 2 or 3; IA(1)

$-(CH_2)_n-$, where n is 2–4); IA(2)

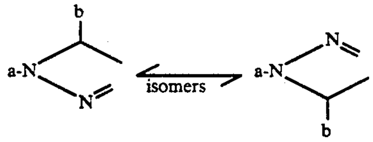

IA(3)

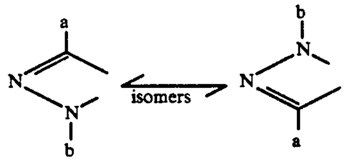

IA(4)

where in formula IA(3) and IA(4)

a is H, $C_{1-4}$ alkyl, alkoxyalkyl or haloalkyl, $C_{5-6}$ cycloalkyl, cycloalkylmethyl, phenyl, benzyl, acyl, pyridyl, alkyl- or arylsulfonyl and b is H, $C_{1-4}$ alkyl, alkoxy, halogen, $NO_2$, $NH_2$, CN, phenyl or benzyl or a and b radicals substituted with $C_{1-4}$ alkyl, haloalkyl, alkoxy, halogen, $NO_2$ or $NH_2$;

provided that when $R_4$ is a radical of the formula IA(3), the ring to which it is attached has only two unsaturated bonds;

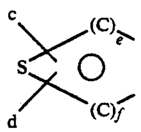

IA(5)

wherein e and f are 0–2 and e+f=2;

c and d are halogen, $C_{1-4}$ alkyl, alkoxy, haloalkyl, hydroxyalkyl, alkylthio, alkylsulphonyl, acyl or alkoxycarbonyl; $C_{3-6}$ cycloalkyl, cycloalkylmethyl or halocycloalkylmethyl; $C_{2-6}$ alkenyl, haloalkenyl, alkynyl or haloalkynyl; phenyl, benzyl or pyridyl and when e or f is 0 and the other is 2, c and d can form a ring;

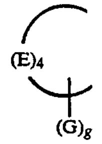

IA(6)

wherein g is 0–6;

one of the E members is O, S, SO, $SO_2$, $ND_{11}$, —CO— or =CH—, the other E members being C atoms, provided that when one E is =C— there is only one double bond in the $(E)_4$ ring and when the E member is not =C—, there may or may not be one double bond in that ring;

$D_{11}$ is H or $C_{1-3}$ alkyl and

G is the same as an uncombined, discrete $R_4$ member in formula IA or tetrahydropyranyl, OH, $CF_3$, phenyl, benzyl or pyridyl or, benzyl- or pyridyl-substituted with $C_{1-4}$ alkyl, alkoxy, alkylthio, $CF_3$, $NO_2$, halogen or

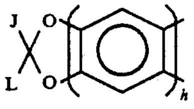

IA(7)

wherein h=0 or 1;

J and L are H, $C_{1-6}$ alkyl or cycloalkyl, both of which may be substituted with $C_{1-3}$ alkyl, alkoxy, hlogen;

when B in formula IA is —CH—, $R_4$ is H, halogen, $NO_2$, $C_{1-3}$ alkyl, haloalkyl, or alkoxy or $C_{2-6}$ alkoxyalkyl or two $R_4$ members together form the radical

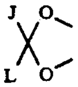

IA(8)

where

J and L are as defined in Formula IA(7);

where in Formula IB, (−) (+)

$R_5$ is $C_{1-5}$ alkyoxy, $NH_2$, —O—$NHD_{12}D_{13}$, or OM; wherein $D_{12}$ and $D_{13}$ are H or $C_{1-4}$ alkyl, and M is an alkali metal or alkaline earth metal and where in Formula IC, $R_6$ and $R_7$ are H or $C_{1-4}$ alkyl, and X is OH, $OD_{14}$, $N(C_{1-3}\ alkyl)_2$, $N(CH_2CH_2OCH_3)_2$, $NHD_{15}$ or one of the following radicals:

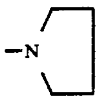 , 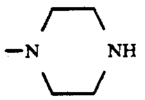 or 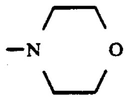

wherein $D_{14}$ is $C_{1-8}$ alkyl or haloalkyl, $C_{3-12}$ alkenyl or alkynyl, $C_{2-12}$ alkoxyalkyl or haloalkoxyalkyl, phenyl, phenoxy, phenyl-$C_{1-8}$ alkyl, phenoxy-$C_{1-8}$-alkyl, a salt-forming cation from ammonium, organic ammonium, alkali and alkaline earth metals, Mn, Cu, Fe, Zn, Co, Pb, Ag, Al or Ni; and $D_{15}$ is H, OH, $C_{3-6}$ cycloalkyl, $C_{1-12}$ alkyl, haloalkyl, hydroxyalkyl, cyanoalkyl, carbamoylalkyl, $C_{3-12}$ alkenyl, haloalkenyl, alkynyl, haloalkynyl, $C_{6-12}$ aryl or aryl-$C_{1-6}$ alkyl or alkoxy, $C_{1-3}$ alkoxycarbonyl-$C_{1-6}$ alkyl, furyl, or tetrahydrofuryl;

said compound of Formula I being used alone or in admixture with other known herbicidal compounds as co-herbicides, preferably an acetanilide of the formula

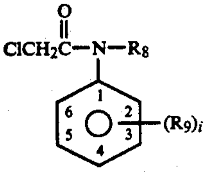

IV wherein $R_8$ is hydrogen, $C_{1-6}$ alkyl, haloalkyl, alkoxy or alkoxyalkyl, alkenyl, haloalkenyl, alkynyl or haloalkynyl having up to 6 carbon atoms, $C_{5-10}$ heterocyclyl or heterocyclylmethyl having O, S and/or N atoms and which may be substituted with halogen, $C_{1-4}$ alkyl, carbonylalkyl or carbonylalkoxyalkyl, nitro, amino or cyano groups;

$R_9$ is hydrogen, halogen, nitro, amino, $C_{1-6}$ alkyl, alkoxy or alkoxyalkyl, and i is 0–5 and (b) an antidotally-effective amount of (i) a compound of the formula

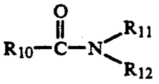

II wherein $R_{10}$ can be selected from the group consisting of haloalkyl; haloalkenyl; alkyl; alkenyl; cycloalkyl; cycloalkylalkyl; halogen; hydrogen; carboalkoxy; N-alkenylcarbamylalkyl; N-alkenylcarbamyl; N-alkyl-N-alkynylcarbamyl; N-alkyl-N-alkynylcarbamylalkyl; N-alkenylcarbamylalkoxyalkyl; N-alkyl-N-alkynylcarbamylalkoxyalkyl; alkynoxy; haloalkoxy; thiocyanatoalkyl; alkenylaminoalkyl; alkylcarboalkyl; cyanoalkyl; cyanatoalkyl; alkenylaminosulfonoalkyl; alkylthioalkyl; haloalkylcarbonyloxyalkyl; alkoxycarboalkyl; haloalkenylcarbonyloxyalkyl; hydroxyhaloalkyloxyalkyl; hydroxyalkylcarboalkyoxyalkyl; hydroxyalkyl; alkoxysulfonoalkyl; furyl, thienyl; alkyldithiolenyl; thienalkyl; phenyl and substituted phenyl wherein said substituents can be selected from halogen, alkyl, haloalkyl, alkoxy, carbamyl, nitro, carboxylic acids and their salts and haloalkylcarbamyl; phenylalkyl; phenylhaloalkyl; phenylalkenyl; substituted phenylalkenyl wherein said substituents can be selected from halogen, alkyl, alkoxy, halophenoxy, phenylalkoxy; phenylalkylcarboxyalkyl; phenylcycloalkyl; halophenylalkenoxy; halothiophenylalkyl; halophenoxyalkyl; bicycloalkyl; alkenylcarbamylpyridinyl; alkynylcarbamylpyridinyl; dialkenylcarbamylbicycloalkenyl; alkynylcarbamylbicycloalkenyl;

$R_{11}$ and $R_{12}$ can be the same or different and can be selected from the group consisting of alkenyl; haloalkenyl; hydrogen; alkyl; haloalkyl; alkynyl; cyanoalkyl; hydroxyalkyl; hydroxyhaloalkyl; haloalkylcarboxyalkyl; alkylcarboxyalkyl; alkoxycarboxyalkyl; thioalkylcarboxyalkyl; alkoxycarboalkyl; alkylcarbamyloxyalkyl; amino; formyl; haloalkyl-N-alkylamido; haloalkylamido; haloalkylamidoalkyl; haloalkyl-N-alkylamidoalkyl; haloalkylamidoalkenyl; alkylimino; cycloalkyl; alkylcycloalkyl; alkoxyalkyl; alkylsulfonyloxyalkyl; mercaptoalkyl; alkylaminoalkyl; alkoxycarboalkenyl; haloalkylcarbonyl; alkylcarbonyl; alkenylcarbamyloxyalkyl; cycloalkylcarbamyloxyalkyl; alkoxycarbonyl; haloalkoxycarbonyl; halophenylcarbamyloxyalkyl; cycloalkenyl; phenyl; substituted phenyl wherein said substituents can be selected from alkyl, halogen, haloalkyl, alkoxy, haloalkylamido, phthalamido, hydroxy, alkylcarbamyloxy, alkenylcarbamyloxy, alkylamido, haloalkylamido or alkylcarboalkenyl; phenylsulfonyl; substituted phenylalkyl wherein said substituents can be selected from halogen or alkyl; dioxyalkylene, halophenoxyalkylamidoalkyl; alkylthiodiazolyi; piperidyl; piperidylalkyl; dioxolanylalkyl, thiazolyl; alkylthiazolyl; benzothiazolyl; halobenzothiazolyl; furyl; alkyl-substituted furyl; furylalkyl; pyridyl; alkylpyridyl; alkyloxazolyl; tetrahydrofurylalkyl; 3-cyano, thienyl; alkyl-substituted thienyl; 4,5-polyalkylene-thienyl; α-haloalkylacetamidophenylalkyl; α-haloalkylacetamidonitrophenylalkyl; α-haloalkylacetamidohalophenylalkyl; cyanoalkenyl;

$R_{11}$ and $R_{12}$ when taken together can form a structure consisting of piperidinyl; alkylpiperidinyl; pyridyl; di- or tetrahydropyridinyl; alkyltetrahydropyridyl; morpholyl; alkylmorpholyl; azabicyclononyl; diazacycloalkanyl, benzoalkylpyrrolidinyl; oxazolidinyl; perhydrooxazolidinyl; alkyloxazolidyl; furyloxazolidinyl, thienyloxazolidinyl, pyridyloxazolidinyl, pyrimidinyloxazolidinyl, benzooxazolidinyl, $C_{3-7}$ spirocycloalkyloxazolidinyl, alkylaminoalkenyl; alkylideneimino; pyrrolidinyl; piperidonyl; perhydroazepinyl; perhydroazocinyl; pyrazolyl; dihydropyrazolyl; piperazinyl; perhydro-1,4-diazepinyl; quinolinyl, isoquinolinyl; di-, tetra- and perhydroquinolyl- or-isoquinolyl; indolyl and di- and perhydroindolyl and said combined $R_{11}$ and $R_{12}$ members substituted with those independent $R_{11}$ and $R_{12}$ radicals enumerated above; or (ii) one of the following compounds α-[(Cyanomethoxy)imino]benzeneacetonitrile, α-[(1,3-Dioxolan-2-yl-methoxy)-iminol]-benzeneacetonitrile, 5-Thiazolecarboxylic acid, 2-chloro-4-trifluoromethyl, benzyl ester, Benzenemethamine, N-[4-(dichloromethylene)-1,3-dithiolan-2-ylidene]-α-methyl, hydrochloride, Diphenylmethoxy acetic acid, methyl ester, 1,8-Naphthalic anhydride, 4,6-Dichloro-2-phenyl-pyrimidine, 2-Chloro-N-[1-(2,4,6-trimethylphenyl)-ethenyl]acetamide, Ethylene glycol acetal of 1,1-dichloroacetone;

provided that when the compound of Formula I is imazaquin, the antidotal compound is other than 1,8-naphthalic anhydride, oxabetrinil, flurazole or N,N-diallyl di-chloroacetamide and when the compound of Formula I is imazethapyr, the antidotal compound is other than 1,8-naphthalic anhydride.

Preferred herbicidal compounds according to Formula I are those wherein $R_1$ and $R_2$ are H, $C_{1-4}$ alkyl or haloalkyl, $R_3$ is H, W is O and R is a radical according to Formula IA wherein the dashed line represents an unsaturated bond, A is COOH or an amide, ester or salt thereof and $R_4$ is at least one $C_{1-4}$ alkyl group or two $R_4$ groups combine to form a benzo radical with the B-containing ring.

Preferred species of herbicidal compounds according to the above formulae include the following 3-Quinolinecarboxylic acid, 2-[4,5-dihydro-4-methyl-4-(1-methylethyl)-5-oxo-1H-imidazol2-yl], (common name "imazaguin", active ingredient in SCEPTER ® herbicide), 3-Pyridinecarboxylic acid, 2-[4,5-dihydro-4-methyl-4-(1-methylethyl)-5-oxo-1H-imidazol-2-yl], (common name "imazapyr", active ingredient in ARSENAL ® herbicide), Benzoic acid, 2-(4,5-dihydro-4-methyl-4-(1-methylethyl)-5-oxo-1H-imidazol-2-yl]-4 (or 5)-methyl-, (common name "AC-222293", active ingredient in ASSERT ® herbicide), 3-Pyridinecarboxylic acid, 5-ethyl-2-[4-methyl-4-(1-methylethyl)-5-oxo-1H-imidazol-2-yl], (common name "imazapyr" (also "AC-263499) active ingredient in PURSUIT ® herbicide), and 3-Pyridinecarboxylic acid, 2-[4,5-dihydro-4-methyl-4-(1-methylethyl)-5-oxo-1H-imidazol-2-yl]-5-methyl-, ammonium salt, (common name "AC263222", active ingredient in CADRE ® herbicide).

2-(5-Methyl-5-trifluoromethyl-1-H-imidazol-4-on-2-yl)-pyridin-3-carboxylic acid;

2-(5-Methyl-5-trifluoromethyl-1-H-imidazol-4-on-2-yl)5-(m)ethyl isonicotinic acid;

2-[5-(1-Fluoroethyl)-5-(m)ethyl-H-imidazol-4-on-2-yl]isonicotinic acid;

2-(5-(Difluoromethyl-5-(m)ethyl-1-H-imidazol-4-on-2yl]-5-(m)ethyl-isonicotinic acid;

2-(5-(1-Fluoroethyl)-5-(m)ethyl)-imidazol-4-on-2-yl]isonicotinic (m)ethyl ester;

Preferred herbicidal acetanilide compounds according to Formula IV are those wherein the $R_8$ member is an alkoxyalkyl group having up to 6 carbon atoms and $R_9$ is a $C_{1\ 6}$ alkyl or alkoxyalkyl radical. The most preferred species are 2-chloro-2'-ethyl-6'-methyl-N-(ethoxymethyl) acetanilide (common name "acetochlor"), 2-chloro-2',6'-diethyl-N-(methoxymethyl)acetanilide (common name "alachlor"), 2-chloro-2',6'-diethyl-N-(butoxymethyl) acetanilide, 2-chloro-2'-ethyl-6'-methyl-N-(1-methyl-2-methoxyethyl) acetanilide (common name "metolachlor") and 2-chloro-2',6'-dimethyl-N-(pyrazolylmethyl) acetanilide (common name "metazachlor").

One group of preferred antidotal compounds includes those according to Formula II wherein $R_{10}$ is $C_{1-3}$ haloalkyl, $R_{11}$ and $R_{12}$ are independently $C_{2-4}$ alkenyl or haloalkenyl or 2,3-dioxolan-2-yl-methyl and $R_{11}$ and $R_{12}$ when combined form a $C_{5-10}$ saturated or unsaturated heterocyclic ring containing O, S and/or N atoms and which may be substituted with $C_{1-5}$ alkyl, haloalkyl, alkoxy, or alkoxyalkyl or haloacyl groups. The preferred haloalkyl $R_{10}$ member in Formula II is dichloromethyl. Preferred species in this group of antidotal compounds are N,N-diallyl-dichloroacetamide and N-(2-propenyl)-N-(1,3-dioxolanylmethyl)dichloroacetamide.

Still more preferred antidotal compounds is according to Formula II is a group of substituted 1,3-oxazolidinyl dichloroacetamide having the formula

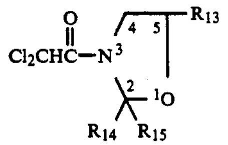

III wherein $R_{13}$ is hydrogen, $C_{1-4}$ alkyl, alkylol, haloalkyl or alkoxy, $C_{2-6}$ alkoxyalkyl, phenyl or a saturated or unsaturated heterocyclic radical having $C_{5-10}$ ring atoms and containing O, S and/or N atoms, and $R_{14}$ and $R_{15}$ are independently hydrogen, $C_{1-4}$ alkyl or haloalkyl, phenyl or a heterocyclic $R_{13}$ member or together with the carbon atom to which they are attached may form a $C_3$–$C_7$ spirocycloalkyl group.

Preferred members according to Formula III are those wherein $R_{13}$ is one of said heterocyclic members and $R_{14}$ and $R_{15}$ are independently methyl, trifluoromethyl or when combined with the carbon atom to which attached form a $C_5$ or $C_6$ cycloalkyl radical.

Preferred antidotal compounds according to Formula III are the following compounds:

Oxazolidine, 3-(dichloroacetyl)-2,2,5-trimethyl-,

Oxazolidine, 3-(dichloroacetyl)-2,2-dimethyl-5-phenyl-,

Oxazolidine, 3-(dichloroacetyl)-2,2-spirocyclohexyl-,

Oxazolidine, 3-(dichloroacetyl)-2,2-dimethyl-5-(2-furanyl)-,

Oxazolidine, 3-(dichloroacetyl)-2,2-dimethyl-5-(2-thienyl)-,

Pyridine, 3-[3-(dichloroacetyl)-2,2-dimethyl-5-oxazolidinyl]-.

Another group of dichloroacetamide antidotal compounds according to Formula II are the following compounds:

4-(Dichloroacetyl)3,4-dihydro-3-methyl-2H-2,4-benzoxazine,

Ethanone, 2,2-dichloro-1-(1,2,3,4-tetrahydro-1-methyl-2-isoquinolinyl)-,

Cis/trans-piperazine, 1,4-bis(dichloroacetyl)-2,5-dimethyl-,

N-(Dichloroacetyl)-1,2,3,4-tetrahydroquinaldine, 1,5-Diazacyclononane, 1,5-bis(dichloroacetyl), 1-Azaspiro[4,4]nonane, 1-(dichloroacetyl).

Still another preferred group of antidotal compounds according to Formula II which do not have the dichloroacetamide structure are the following compounds:

α-[(Cyanomethoxy)imino]benzeneacetonitrile,

α-[(1,3-Dioxolan-2-yl-methoxy) imino]benzeneacetokitrile,

5-Thiazolecarboxylic acid, 2-chloro-4-trifluoromethyl, benzyl ester,

Benzenemethamine, N-[4-(dichloromethylene]-1,3-ditholan-2-ylidene]-α-methyl, hydrochloride, Diphenylmethoxy acetic acid, methyl ester, 1,8-Naphthalic anhydride, 4,6-Dichloro-2-phenyl-pyrimidine, 2-Chloro-N-[1-(2,4,6-trimethylphenyl)ethenyl]acetamide, and Ethylene glycol acetal of 1,1-dichloroacetone.

The herbicidal and antidotal compounds of Formulae I-IV are known in the art. The sub-group of 1,3-oxazolidine dichloroacetamides of Formula III are the subject of copending application, Ser. No. is 07/212,621, of common assignment herewith, priority application for EP 304409 published Feb. 22, 1989.

The term "haloalkyl" embraces radicals wherein any one or more of the carbon atoms, preferably from 1 to 4 in number, is substituted with one or more halo groups, preferably selected from bromo, chloro and fluoro. Specifically embraced by the term "haloalkyl" are monohaloalkyl, dihaloalkyl and polyhaloalkyl groups. A monohaloalkyl group, for example, may have either a bromo, a chloro, or a fluoro atom within the group. Dihaloalkyl and polyhaloalkyl groups may be substituted with two or more of the same halo groups, or may have a combination of different halo groups. A dihaloalkyl group, for example, may have two bromo atoms, such as a dibromomethyl group, or two chloro atoms, such as a dichloromethyl group, or one bromo atom and one chloro atom, such as a bromochloromethyl group. Examples of a polyhaloalkyl are perhaloalkyl groups such as trifluoromethyl and perfluoroethyl groups.

Preferred haloalkyl R members are dihalomethyl, particularly dichloromethyl, while the preferred haloalkyl $R_1$ member is a tri-halogenated methyl radical, preferably trifluoromethyl.

Where the term "alkyl" is used either alone or in compound form (as in "haloalkyl"), it is intended to embrace linear or branched radicals having up to four carbon atoms, the preferred members being methyl and ethyl.

By "agriculturally-acceptable salts" of the compounds defined by the above formula is meant a salt or salts which readily ionize in aqueous media to form a cation of said compounds and a salt anion, which salts have no deleterious effect on the antidotal properties of said compounds or of the herbicidal properties of a given herbicide and which permit formulation of the herbicide-antidote composition without undue problems of mixing, suspension, stability, is applicator equipment use, packaging, etc.

By "antidotally-effective" is meant the amount of antidote required to reduce the phytotoxicity level or effect of a herbicide, preferably by at least 10% or 15%, but naturally the greater the reduction in herbicidal injury the better.

By "herbicidally-effective" is meant the amount of herbicide required to effect a meaningful injury or destruction to a significant portion of affected undesirable plants or weeds. Although of no hard and fast rule, it is desirable from a commercial viewpoint that 80-85% or more of the weeds be destroyed, although commercially significant suppression of weed growth can occur at much lower levels, particularly with some very noxious, herbicide-resistant plants.

The terms "antidote", "safening agent", "safener", "antagonistic agent", "interferant", "counter-agent", "crop protectant" and "crop protective", are often-used terms denoting a compound capable of reducing the phytotoxicity of a herbicide to a crop plant or crop seed. The terms "crop protectant" and "crop protective" are sometimes used to denote a composition containing as the active ingredients, a herbicide-antidote combination which provides protection from competitive weed growth by reducing herbicidal injury to a valuable crop plant while at the same time controlling or suppressing weed growth occurring in the presence of the crop plant. Antidotes protect crop plants by interfering with the herbicidal action of a herbicide on the crop plants so as to render the herbicide selective to weed plants emerging or growing in the presence of crop plants.

Herbicides which may be used as co-herbicides with the imidazolinones of Formula I with benefit in combination with an antidote of the described class include preferably thiocarbamates (including dithiocarbamates), acetamides, heterocyclyl phenyl ethers (especially phenoxypyrazoles), benzoic acid and its salts, esters and amides, pyridines, and sulfonylureas. It is within the purview of this invention that other classes of herbicides, e.g., triazines, ureas, diphenyl ethers, nitroanilines, thiazoles, isoxazoles, etc., the individual members of which classes may be derivatives having one or more substituents selected from a wide variety of radicals may suitably be used as co-herbicides. Such combinations can be used to obtain selective weed control with low crop injury in several varieties of monocotyledonous crop plants such as corn, grain sorghum (milo), and cereals such as wheat, rice, barley, oats, and rye, as well as several varieties of dicotyledonous crop plants including oil-seed crops such as soybeans and cotton. Particular utility for the antidotal compounds of this invention has been experienced with various herbicides in corn, sorghum and soybeans.

Examples of important thiocarbamate herbicides are the following:

cis-/trans-2,3-dichloroallyl-diisopropylthiolcarbamate (common name "diallate");

ethyl dipropylthiocarbamate (common name "EPTC");

S-ethyl diisobutyl (thiocarbamate) (common name "butylate");

S-propyl dipropyl(thiocarbamate) (common name "vernolate");

2,3,3-trichloroallyl-diisopropylthiolcarbamate (common name "triallate")'

Examples of important acetamide herbicides are the following:

2-chloro-N-isopropylacetanilide (common name "propachlor");

2-chloro-1',6'-diethyl-N-(methoxymethyl)-acetanilide (common name "alachlor");

2-chloro-2',6'-diethyl-N-(butoxymethyl)-acetanilide (common name "butachlor");

2-chloro-N-(ethoxymethyl)-6'-ethyl-o-acetotoluidide (common name "acetochlor"); ethyl ester of N-chloroacetyl-N-(2,6-di-ethylphenyl)glycine (common name "diethatyl ethyl");

2-chloro-N-(2,6-dimethylphenyl)-N-(2-methoxy-ethyl-)acetamide (common name "dimethachlor");

2-chloro-N-(2-methoxy-1-methylethyl)-6'-ethyl-o-acetotoluidide (common name "metolachlor");

2-chloro-2'-methyl-6'-methoxy-N-(isopropoxymethyl-)acetanilide;

2-chloro-2',6'-dimethyl-N-(1-pyrazol-1-yl-methyl)-acetanilide (common name "metazochlor")'

2-chloro-N(2,6-dimethyl-1-cyclohexen-1-yl)-N-(1H-pyrazol-1-ylmethyl)acetamide;

2-chloro-6'-trifluoromethyl-N-(isopropoxymethyl) acetanilide;

2-chloro-2'-methyl-6'-trifluoromethyl-N-(ethoxymethyl)acetanilide;

2-chloro-2'-ethyl-6'-trifluoromethyl-N-(1-pyrazolyl-1-ylmethyl)acetanilide;

2-chloro-N-isopropyl-1-(3,5,5-trimethylcyclohexen-1-yl)acetamide (common name "trimexachlor").

Examples of important pyridine herbicides include:

3-pyridinecarboxylic acid, 2-(difluoromethyl)-5-4,5-dihydro-2-thiazolyl)-4-(2-methylpropyl)-6-(trifluoromethyl)-, methyl ester;

3-pyridinecarboxylic acid, 2-(difluoromethyl)-4-(2-methylpropyl)-5-(1H-pyrazol-1-ylcarbonyl)-6-(trifluoromethyl)-, methyl ester;

3,5-pyridine dicarbothioic acid, 2-(difluoromethyl)-4-(2-methylpropyl)-6-(trifluoromethyl)-, S,S-dimethyl ester;

3,5-pyridinedicarboxylic acid, 2-(difluoromethyl)-4-(2-methylpropyl)-6-trifluoromethyl, dimethyl ester.

Examples of important heterocyclyl phenyl ethers include:

5-(trifluoromethyl)-4-chloro-3-(3'-[1-ethoxycarbonyl]-ethoxy-4'-nitrophenoxy)-1-methylpyrazol;

5-(trifluoromethyl)-4-chloro-3-(3'-methoxy-4'-nitrophenoxy)-1-methylpyrazole;

5-(trifluoromethyl)-4-chloro-3(3'-[1-butoxycarbonyl]-ethoxy-4'-nitrophenoxy)-4-methylpyrazol;

5-(trifluoromethyl)-4-chloro-3-(3'-methylsulfamoylcarbonyl propoxy-4'-nitrophenoxy)-4-methylpyrazol;

5-(trifluoromethyl)-4-chloro-3-(3'-propoxycarbonylmethyloxime-4'-nitrophenoxy)-1-methylpyrazole;

(+)-2-[4-[[5-(trifluoromethyl)-2-pyridinyl]oxy] phenoxy]propanoic acid (9CI).

Examples of important sulfonylureas include:

Benzenesulfonamide, 2-chloro-N-[[C(4-methoxy-6-methyl-1, 3, 5-triazin-2-yl) amino) carbonyl]; Benzoic acid, 2-[[[[(4-chloro-6-methoxy-2-pyrimidinyl) amino]carbonyl] amino] sulfonyl]-ethyl ester;

2-Thiophenecarboxylic acid, 3-[[[[(4,6-dimethoxy-1,3,5-triazin-2-yl)amino]carbonyl] amino]sulfonyl]-, methyl ester;

Benzoic acid, 2-[[[[(4, 6-dimethyl-2-pyrimidinyl) amino] carbonyl]amino] sulfonyl] methyl ester;

Benzenesulfonamide, 2-(2-chloroethoxy)-N-[[(4-methoxy-6-methyl-1, 3, 5-triazin-2-yl) amino] carbonyl];

Benzoic acid, 2-[[[[(4-methoxy-6-methyl-1,3,5-triazin-2-yl) amino]carbonyl] amino] sulfonyl]-methyl ester;

Examples of important benzoic acid derivative herbicides include:

3,6-Dichloro-2-methoxybenzoic acid (common name "dicamba"), 2,5-Dichloro-3-aminobenzoic acid (common name "amiben" and "chloramiben"), 5-(2'-Chloro-4'-trifluoromethylphenoxy)-2-nitrobenzoic acid (common name "acifluorfen"), 2,6-Dichlorobenzonitrile (common name "dichlobenil"), 3,5,6-Trichloro-2-methoxybenzoic acid (common name "Tricamba"), 2,3,6-Trichlorobenzoic acid, and 2,3,5,6-Tetrachlorobenzoic acid, and salts, esters and amides of the above acids. Examples of other important herbicides include:

2-Chloro-4-(ethylamino)-6-(isopropylamino)-symbriazine;

4-Amino-6-tertbutyl-3-(methylthio)-AS-triazine-5(4H)one;

Trifluoro-2,6-dinitro-N,N-dipropyl-p-toluidine;

Benzeneamine, N-(1-ethylpropyl)-3, 4-dimethyl-2, 6-dinitro-;

2-Pyrrolidinone, 3-chloro-4-(chloromethyl)-1-[3-(trifluoromethyl) phenyl], trams-;

3-Isoxazolidinone, 2-[(2-chlorophenyl) methyl]-4, 4-dimethyl-;

2-Imidazolidinone, 3-[5-(1,1-dimethylethyl)-3-isoxazolyl]-4-hydroxy-1-methyl-;

2-Chloro-4-(1-cyano-1-methylethylamino)-6-ethylamino-1,3,5-triazine;

Methyl 5-(2,4-dichlorophenoxy)-2-nitrobenzoate;

1'-(Carboethoxy)ethyl 5-[2-chloro-4-(trifluoromethyl)-phenoxy]-2-nitrobenzoate;

Ammonium-DL-homoalanin-4-yl (methyl) phosphinate;

2-(3,4-Dichlorophenyl)-4-methyl-1,2,4-oxadiazolidine-3,5-dione.

The herbicides of particular and preferred interest as co-herbicides with the imidazolinones of Formula I in compositions with antidotes according to this invention include each of the above-mentioned species from different chemical classes of compounds exemplified as important herbicides, particularly those of current commercial interest and use and those which may be determined of commercial utility. Co-herbicidal compounds of preference include the following acetanilides:

alachlor, acetochlor, butachlor, metolachlor, metazochlor, 2-chloro-2'-methyl-6'-methoxy-N-(isopropoxymethyl-)acetanilide, 2-chloro-2'-methyl-6'-trifluoromethyl-N-(ethoxymethyl)acetanilide, and 2-chloro-2',6'-dimethyl-N-(2-methoxyethyl)acetanilide.

All of the above specifically-named herbicides are known in the art.

As further detailed infra, while not necessary, the composition containing the herbicide-antidote combination may also contain other additaments, e.g., biocides such as insecticides, fungicides, nematocides, miticides, etc., fertilizers, inert formulation aids, e.g., surfactants, emulsifiers, defoamers, dyes, etc.

Combinations may be made of any one or more of the described antidote compounds with any one or more of the herbicide compounds of Formula I and coherbicides mentioned herein.

It will be recognized by those skilled in the art that all herbicides have varying degrees of phytotoxicity to various plants because of the sensitivity of the plant to the herbicide. Thus, e.g., although certain crops such as corn and soybeans have a high level of tolerance (i.e., low sensitivity) to the phytotoxic effect of alachlor, other crops, e.g., milo (grain sorghum), rice and wheat, have a low level of tolerance (i.e., high sensitivity) to the phytotoxic effects of alachlor. The same type of sensitivity to herbicides as shown by crop plants is also exhibited by weeds, some of which are very sensitive, others very resistant to the phytotoxic effects of the herbicide.

When the sensitivity of a crop plant to a herbicide is low, whereas the sensitivity of a weed to that herbicide is high, the "selectivity factor" of the herbicide for preferentially injuring the weed while not injuring the crop is high.

In an analogous manner, but more complex, an antidotal compound may, and commonly does, have varying degrees of crop protective effect against different herbicides in different crops. Accordingly, as will be appreciated by those skilled in the art, the various antidotes of this invention, as with all classes of antidotal compounds, will have greater or lesser crop safening effects against various herbicides in various crops than in others. Thus, while a given antidotal compound may have no crop protective ability against a given herbicide in a given crop, that same antidotal compound may have a very high crop protective ability against the same given herbicide in a different crop or against a different herbicide in the same crop. This is an expected phenomenon.

DETAILED DESCRIPTION OF THE INVENTION

Antidote Compounds

As mentioned earlier, the antidotal compounds used in the practice of this invention are known compounds. The preferred compounds used herein are the 1,3-oxazolidine dichloroacetamides according to Formula III wherein the $R_{13}$ member is a heterocyclic radical. Those compounds are separately disclosed and claimed in the assignee's said copending application, Ser. No. 07/212,621 and its corresponding EP 304409, published Feb. 22, 1989. The synthesis methods of said EP 304409 for said 1,3-oxazolidine dichloroacetamide antidotes are also disclosed in said U.S. Ser. No. 07/212,621, and these documents are hereby incorporated by reference.

Biological Evaluation

Effective weed control coupled with low crop injury is a result of treatment of a plant locus with a combination of herbicide compound and antidote compound. By application to the "plant locus" is meant application to the plant growing medium, such as soil, as well as to the seeds, emerging seedlings, roots, stems, leaves, or other plant parts.

The phrase "combination of herbicide compound and antidote compound" embraces various methods of treatment. For example, the soil of a plant locus may be treated with a "tank-mix" composition containing a mixture of the herbicide and the antidote which is "in combination". Or, the soil may be treated with the herbicide and antidote compounds separately so that the "combination" is made on, or in, the soil. After such treatments of the soil with a mixture of herbicide and antidote or by separate or sequential application of the herbicide and antidote to the soil, the herbicide and antidote may be mixed into or incorporated into the soil either by mechanical mixing of the soil with implements or by "watering in" by rainfall or irrigation. The soil of a plant locus may also be treated with antidote by application of the antidote in a dispersible-concentrate form such as a granule. The granule may be applied to a furrow which is prepared for receipt of the crop seed and the herbicide may be applied to the plant locus either before or after in-furrow placement of the antidote-containing granule so that the herbicide and antidote form a "combination". Crop seed may be treated or coated with the antidote compound either while the crop seed is in-furrow just after seeding or, more commonly, the crop seed may be treated or coated with antidote prior to seeding into a furrow. The herbicide may be applied to the soil plant locus before or after seeding and a "combination" is made when both herbicide and antidote-coated seed are in the soil. Also contemplated as a "combination" is a commercially-convenient association or presentation of herbicide and antidote. For example, the herbicide and antidote components in concentrated form may be contained in separate containers, but such containers may be presented for sale or sold together as a "combination". Or, the herbicide and antidote components in concentrated form may be in a mixture in a single container as a "combination". Either such "combination" may be diluted or mixed with adjuvants suitable for soil applications. Another example of a commercially-presented combination is a container of antidote-coated crop seed sold, or presented for sale, along with a container of herbicide material. These containers may, or may not, be physically attached to each other, but nonetheless constitute a "combination of herbicide and antidote" when intended for use ultimately in the same plant locus.

In the foregoing description of various modes of application of the herbicide-antidote combinations, it is inherent that each form of application requires that in some manner, the herbicide and antidote will form a "composition" of those agents.

The amount of antidote employed in the methods and compositions of the invention will vary depending upon the particular herbicide with which the antidote is employed, the rate of application of the herbicide, the particular crop to be protected, and the manner of application to the plant locus. In each instance the amount of antidote employed is a safening-effective amount, that is, the amount which reduces, or protects against, crop injury that otherwise would result from the presence of the herbicide. The amount of antidote employed will be less than an amount that will substantially injure the crop plant.

The antidote can be applied to the crop plant locus in a mixture with the selected herbicide. For example, where the crop seed is first planted, a suitable mixture of antidote and herbicide, whether in a homogeneous liquid, emulsion, suspension or solid form, can be applied to the surface of, or incorporated in, the soil in which the seed has been planted. Or, the herbicide-antidote mixture may be applied to the soil, and then the seed thereafter "drilled" into the soil below the soil layer containing the herbicide-antidote mixture. The herbicide will reduce or eliminate the presence of undesirable weed plants. Where the herbicide would by itself injure the crop seedlings, the presence of the antidote will reduce or eliminate the injury to the crop seed caused by the herbicide. It is not essential that the application of herbicide and the antidote to the plant locus be made using the selected herbicide and antidote in the form of a mixture or composition. The herbicide and the antidote may be applied to the plant locus in a sequential manner. For example, the antidote may be first applied to the plant locus and thereafter the herbicide is applied. Or, the herbicide may be first applied to the plant locus and thereafter the antidote is applied.

The ratio of herbicide to antidote may vary depending upon the crop to be protected, weed to be inhibited, herbicide used, etc., but normally a herbicide-to-antidote ratio ranging from 1:25-to-60:1 (preferably 1:5-to-30:1) parts by weight may be employed, although much higher rates of antidote may be used, e.g., 1:100-1:300 parts by weight of herbicide-to-antidote. As indicated above, the antidote may be applied to the plant locus in a mixture, i.e., a mixture of a herbicidally-effective amount of herbicide and a safening-effective amount of an antidote, or sequentially, i.e., the plant locus may be treated with an effective amount of the herbicide followed by a treatment with the antidote or vice versa. In general, effective herbicidal amounts are in the range of about 0.03 to about 12 kilograms/hectare, but rates as low as 0.004 kg/ha may be used effectively. The preferred range of rate of application is from about 0.1 to about 10 kg/ha. Preferably, antidote application rates range from about 0.5 kg/ha down to about 0.05 kg/ha. It will be appreciated that at times amounts either below or above these ranges will be necessary to obtain the best results. The selection of the herbicide to inhibit the emergence and growth of weeds depends upon the species of weeds to be controlled and the crop to be protected.

The application of the antidote can be made directly to the seed before planting. In this practice, a quantity of crop seed is first coated with the antidote. The coated seed is thereafter planted. The herbicide may be applied to the soil before or after the coated seed is planted.

In field applications, the herbicide, antidote, or a mixture thereof, may be applied to the plant locus without any adjuvants other than a solvent. Usually, the herbicide, antidote, or a mixture thereof, is applied in conjunction with one or more adjuvants in liquid or solid form. Compositions or formulations containing mixtures of an appropriate herbicide and antidote usually are prepared by admixing the herbicide and antidote with one or more adjuvants such as diluents, solvents, extenders, carriers, conditioning agents, water, wetting agents, dispersing agents, or emulsifying agents, or any suitable combination of these adjuvants. These mixtures may be in the form of particulate solids, granules, pellets, wettable powders, dusts, solutions, aqueous dispersions, or emulsions.

Application of the herbicide, antidote, or mixture thereof, can be carried out by conventional techniques utilizing, for example, hand-carried or tractor-mounted spreaders, power dusters, boom and hand sprayers, spray dusters, and granular applicators. If desired, application of the compositions of the invention to plants can be accomplished by incorporating the compositions in the soil or other media.

Evaluations of safening activity of a wide variety of representative antidote compounds and imidazolinone compounds according to this invention were carried out using the specific procedures of Examples 5-13 below in greenhouse testing. Measurements of biological response as reported in Tables 1-9 were made in the following manner. A visual comparison was made between a crop plant treated with a herbicide alone and crop plant having no herbicide or antidote treatment. A number was assigned to this visual comparison indicating the percent injury or inhibition to the herbicide-alone treated crop plant (column "WO" in Tables 1 and 2 indicating herbicide "without" antidote). Also, a visual comparison was made between the crop plant treated with herbicide+antidote combination and the crop plant having no herbicide or antidote treatment. A number was assigned to this visual comparison indicating the percent injury or inhibition to the herbicide+antidote treated crop plant (column "W" in Tables 1 and 2 indicating herbicide "with" antidote). Observations of response by the weed species to herbicide or herbicide+antidote were similarly recorded. The degree of reduction of herbicide injury provided by an antidote compound is indicated by the magnitude that the plant inhibition number of column "WO" exceeds the corresponding number of column "W". Also reported in Tables 1 and 2 are data in parenthesis showing "safening effect" (defined below) for the herbicide+antidote combinations calculated from the plant inhibition numbers. These tables show crop or weed column headings under which there are no data. The lack of such data is not an indication of a failed test; rather it is merely an indication that the particular herbicide+antidote rate combination was not tested with that crop or weed.

In Tables 1 and 2 the symbols used have the following meanings:

W=% Plant Inhibition caused by combination of of herbicide and antidote.

WO=% Plant Inhibition caused by herbicide alone.

Data reported in parentheses = Safening Effect $$(\ ) = \frac{WO - W}{WO} \times 100$$

Herbicide and antidote rates in all tables below are given in kilograms per hectare (Kg/ha).

Listed below are the names of the herbicidal and antidotal compounds for which data are reported in the Tables.

| Herbicide No. | Compound |
|---|---|
| 1 | 3-Quinolinecarboxylic acid, 2-[4,5-dihydro-4-methyl-4-(1-methylethyl)-5-oxo-1H-imidazol-2-yl], (common name "imazaquin", active ingredient in SCEPTER ® herbicide), |
| 2 | 3-Pyridinecarboxylic acid, 2-[4,5-dihydro-4-methyl-4-(1-methylethyl)-5-oxo-1H-imidazol-2-yl], (common name "imazapyr", active ingredient in ARSENAL ® herbicide), |
| 3 | Benzoic acid, 2-[4,5-dihydro-4-methyl-4-(1-methylethyl)-5-oxo- |

-continued

| | Compound |
|---|---|
| | 1H-imidazol-2-yl]-4 (or 5)-methyl-, (common name "AC-222,293", active ingredient in ASSERT ® herbicide), |
| 4 | 3-Pyridinecarboxylic acid, 5-ethyl-2-[4,5-dihydro-4-(1-methylethyl)-5-oxo-1H-imidazol-2-yl], (common name "imazethapyr" [also "AC 263,499'], active ingredient in PURSUIT ® herbicide), and |
| 5 | 3-Pyridinecarboxylic acid, 2-[4,5-dihydro-4-methyl-4-(1-methylethyl)-5-oxo-1H-imidazol-2-yl]-5-methyl-, ammonium salt, (common name "AC-263,222", active ingredient in CADRE ® herbicide). |

| Antidote No. | |
|---|---|
| 1 | Acetamide, N,N-Bis(2-propenyl)-Alpha,Alpha-dichloro-, |
| 2 | Cis/trans-piperazine, 1,4-bis-(dichloroacetyl)-2,5-dimethyl-, |
| 3 | 5-Thiazolecarboxylic acid, 2-chloro-4-(trifluoromethyl)-, (phenylmethyl) ester, |
| 4 | Oxazolidine,3-(dichloroacetyl)-2,2,5-trimethyl-, |
| 5 | Benzeneacetonitrile, Alpha-[(cyanomethoxy)imino]-, |
| 6 | Oxazolidine,3-(dichloroacetyl)-2,2-dimethyl-5-phenyl)-, |
| 7 | Benzeneacetonitrile, Alpha-[[(1,3-dioxolan-2-yl)methoxy] imino)]-, |
| 8 | 1H-1,2,4-Triazole,1-[[(1,1-dimethylethyl)dimethylsilyl]-(phenylsulfonyl)methyl]-, |
| 9 | 1-Diazacyclononane, 1,5-Bis-(Dichloroacetyl)-, |
| 10 | 1-Azaspiro[4.4]nonane, 2-(dichloroacetyl)-, |
| 11 | Acetamide, 2,2-dichloro-N-(1,3-dioxolan-2-ylmethyl)-N-2-propenyl-, |
| 12 | 1-Azaspiro[4.5]decane, 1-bromochloroacetyl-, |
| 13 | Oxazolidine, 3-(dichloroacetyl)-2,2-dimethyl-5-(2-thienyl)-, |
| 14 | Ethanone, 2,2-dichloro-1-(1,2,3,4-tetrahydro-1-methyl-2-isoquinolinyl)-, |
| 15 | 1,3-dioxolane, 2-(dichloromethyl)-2-methyl-, |
| 16 | Acetamide, 2-chloro-N-[1-(2,4,6-trimethylphenyl)-ethenyl]-, |
| 17 | Oxazolidine, 3-(dichloroacetyl)-3,2,2-trimethyl-, |
| 18 | Pyrrolo[1,2-a]pyrimidin-6(2H)-one, 1-(dichloroacetyl)hexahydro-3,3,8a-trimethyl, |
| 19 | Oxazolidine, 3-(dichloroacetyl)-5-(2-furanyl)-2,2-dimethyl-, |
| 20 | Pyridine, 3-[3-(dichloroacetyl)-2,2-dimethyl-5-oxazolidinyl]-, |
| 21 | Para chlorophenylthio acetonitrile, |
| 22 | Piperazine,1,4-bis(dichloroacetyl)-, |
| 23 | Benzenemethanamine, N-[4-(dichloromethylene)-1,3-dithiolan-2-ylidene]-alpha-methyl-, hydrochloride, |
| 24 | 1H,3H-naphtho[1,8-cd]pyran-1,3-dione, |
| 25 | Phosphonic acid,(alpha-(dichloroacetamido)methyl)-, diphenyl ester, |
| 26 | Piperazine, 1,4-bis(dichloro- |

-continued

| | Compound |
|---|---|
| | acetyl)-,2,6-dimethyl-, |
| 27 | 5-thiazolecarboxylic acid, 2-chloro-, 2-chloroethyl ester, 4-(trifluoromethyl)-, |
| 28 | 5-oxazolecarboxylic acid, 2-[(1,1-dimethylethyl)amino]-4-(trifluoromethyl)-, ethyl ester, |
| 29 | Acetic acid, (diphenylmethoxy)-, methyl ester, |
| 30 | 5-Thiazolecarbothioic acid, 2-chloro-4-(trifluoromethyl)-, S-(phenylmethyl)ester, |
| 31 | Acetamide, 2,2-dichloro-N-[3,5-bis(trifluoromethyl)-phenyl]-, |
| 32 | Quinoline, 1-(dichloroacetyl)-1,2,3,4-tetrahydro-2-methyl-, |
| 33 | Isoquinoline, 2-(dichloroacetyl)-1,2,3,4-tetrahydro-, |
| 34 | Quinoline, 1-(dichloroacetyl)-1,2,3,4-tetrahydro-, |
| 35 | Quinoline, 1-(dichloroacetyl)-1,2-dihydro-2,2,4-trimethyl-, |
| 36 | Acetamide, 2,2-dichloro-N-[2-nitro-4-(trifluoromethyl)-phenyl]-, |
| 37 | Acetamide, 2,2-dichloro-N-(3-fluorophenyl)-, |
| 38 | Acetamide, 2,2-dichloro-N-(2,5-difluorophenyl)-, |
| 39 | 1,4-dioxa-8-azaspiro[4,5]-decane, 8-(dichloroacetyl)-, |
| 40 | Thiazolidine, 3-(dichloroacetyl)-, |
| 41 | Acetamide, N-[(1,1'-biphenyl)-2-yl]-2,2-dichloro-, |
| 42 | Acetamide, 2,2-dichloro-N-[2-[2-[(dichloroacetyl)-amino]phenyl]phenyl]-, |
| 43 | 1-Azaspiro[4.4]nonane, 1-bromochloroacetyl-, |
| 44 | Acetamide, 2,2-dichloro-N-[(3-methoxyphenyl)methyl]-N-(2-propenyl)-, |
| 45 | Acetamide, N-[1,1'-biphenyl]-3-yl-2,2-dichloro-, |
| 46 | Acetamide, 2-chloro-N-[1-(2,6-dichlorophenyl)ethenyl]-, |
| 47 | 1-oxa-4-azaspiro[4.5]decane, 4-bromochloroacetyl-, |
| 48 | Acetamide, 2,2-dibromo-N,N-di-2-propenyl-, |
| 49 | Acetamide, N,N-bis[(3-butynyloxy)methyl]-2,2-dichloro-, |
| 50 | Acetamide, N,N-bis[(3-pentynyloxy)methyl]-2-chloro-, |
| 51 | Acetamide, 2,2-dichloro-N,N-bis[(3-pentynyloxy)methyl]-, |
| 52 | Isoquinoline, 2-(dichloroacetyl)-1,2,3,4-tetrahydro-1-propyl-, |
| 53 | 1H-isoindole, 2-(dichloroacetyl) 2,3-dihydro-, |
| 54 | Isoquinoline, 2-(dichloroacetyl)-1,2,3,4-tetrahydro-1-(1-methylethyl)-, |
| 55 | Acetamide, 2,2-dichloro-N-[1-(2,4,6-trimethylphenyl)-ethenyl]-, |
| 56 | Acetamide, 2,2-dichloro-N-ethyl-N-(methoxymethyl), |
| 57 | Acetamide, 2,2-dichloro-N-2-propenyl-N-[3-(trifluoromethyl)phenyl]-, |
| 58 | Acetamide, N,N'-1,2-ethanediylbis[2,2-dichloro-N-(2-methyl-1-propenyl)]-, |
| 59 | Quinoxaline, 1,4-bis(dichloroacetyl)-1,2,3,4-tetrahydro-, |
| 60 | 1H-1,4-diazonine, 1,4-bis- |

-continued

| | Compound |
|---|---|
| | (dichloroacetyl)octahydro-, |
| 61 | 1H-1,5-diazonine, 1,5-bis-(bromochloroacetyl)octahydro-, |
| 62 | 1H-1,5-diazonine, 1,5-bis-(dibromoacetyl)octahydro-, |
| 63 | 1H-1,5-diazonine, 1,5-bis-(dichloroacetyl)octahydro-3-methyl-, |
| 64 | 1H-1,5-diazonine, 1,5-bis-(dichloroacetyl)octahydro-2-methyl-, |
| 65 | 7-Azaspiro[4.5]decane, 7-(dichloroacetyl)-8,8-dimethyl-, |
| 66 | Quinoaline, 1,4-bis(dichloroacetyl)-1,2,3,4-tetrahydro-2-methyl-, |
| 67 | Isoquinoline, 2-(dichloroacetyl)-1,2,3,4-tetrahydro-1-(trifluoromethyl)-, |
| 68 | Acetamide, 2,2-dichloro-N-ethyl-N-(2-phenylethyl)-, |
| 69 | Acetamide, 2,2-dichloro-N-(ethoxymethyl)-N-(2-phenylethyl)-, |
| 70 | Isoquinoline, 2-(dichloroacetyl)-1,2,3,4-tetrahydro-1,3-dimethyl-, |
| 71 | Isoquinoline, 2-(dichloroacetyl)-1-ethyl-1,2,3,4-tetrahydro-3-methyl-, |
| 72 | Isoquinoline, 2-(dichloroacetyl)-1,2,3,4-tetrahydro-1,7-dimethyl-, |
| 73 | 1,5-diazocine, 1,5-bis(dichloroacetyl)octahydro-, |
| 74 | Piperazine, 1,4-bis(dichloroacetyl)-2-methyl-5-(1-methylethyl)-, (2S,5R-trans)-, |
| 75 | Piperazine, 1,4-[bis(dichloroacetyl)]-2-phenyl-, |
| 76 | Oxazolidine, 3-(dichloroacetyl)-5-(3-furanyl)-2,2-dimethyl-, |
| 77 | 4-Pentenenitrile, 2-methyl-2-[(4-methylphenyl)thio]- |

The following examples describe preparation of exemplary formulations of herbicide and antidote and mixtures thereof.

EXAMPLE 1

An emulsifiable concentrate type formulation containing acetochlor was prepared containing the following components:

| | % by Wt. |
|---|---|
| Acetochlor (93.1% technical) | 87.13 |
| Epoxy soybean oil | 0.91 |
| Witco C-5438 emulsifier (blend of anionic/non-ionic emulsifiers in ethylene glycol); Witco Chemical Co., New York, N.Y. | 9.00 |
| Orchex 796 (a spray oil filter) | 2.93 |
| GE AG-78 antifoaming agent (polysiloxane); General Electric Co., Waterford, N.Y. | 0.02 |
| Methyl violet dye; Dye Specialties Co., Jersey City, N.J. | 0.01 |

These components were mixed together at room temperature until a uniform blend was obtained. The formulation had a specific gravity of 1.1101 observed at 20° C. and calculated against water at 15.6° C., and had a flash point above 200° C. (tag closed-cup method). The formulation showed fair emulsion bloom at water hardness concentrations of 114 ppm, 342 ppm and 1000 ppm. The emulsions had 1 ml cream after one hour at each water hardness concentration. The formulation was a purple viscous liquid and contained 87.13% by weight of acetochlor.

EXAMPLE 2

An emulsifiable concentrate formulation containing 1-oxa-4-azaspiro (4,5) decane, 4-(dichloroacetyl), having the common name "AD-67" as the antidote compound was prepared for use in various tests. AD-67 is also named oxazolidine, 3-(dichloroacetyl)-2,2-spirocyclohexyl-. The formulation contained the following ingredients:

| | % by wt. |
|---|---|
| AD-67 (93.5% tech) | 11.44 |
| Sterox NJ | 0.77 |
| FLOMO 54C | 5.96 |
| FLOMO 50H emulsifier | 3.27 |
| Monochlorobenzene | 78.55 |

These components were mixed together at room temperature until a uniform blend was obtained. The formulation had a specific gravity of 1.1222 observed at 20° C. calculated against water at 15.6° C., a solution point of <0° C., and a flash point less than 32° C. The formulation showed good bloom at a concentration in water of 1000 ppm, and perfect bloom at 100 and 342 ppm. Emulsions containing 5% of the formulation were observed one hour after preparation as having a trace cream layer at 114 ppm, and 2 ml layer at 342 ppm and at 1000 ppm water-hardness concentrations.

EXAMPLE 3

An emulsifiable concentrate formulation containing oxazolidine, 3-(dichloroacetyl)-2,2-dimethyl-(5-furanyl)-, was prepared for use in field tests as described later herein. This EC contained the following ingredients:

| | % by wt. |
|---|---|
| Active ingredient (the above compound) | 10.77 |
| Monochlorobenzene | 79.23 |
| Witconate P 1220 | 4.19 |
| Witconol CO-360 | 5.45 |
| Witconol NP-330 | 0.36 |

The above formulation had a specific gravity of 1.1220 at 20° C. calculated against water at 15.6° C. and a flash point of 37.8° C. (100° F.). The formulation exhibited poor bloom in water at concentrations of 114, 342 and 1000 ppm. Emulsions containing 5% of this formulation exhibited a 1 ml layer at the 114 and ppm concentrations and a 10 ml layer at the 1000 ppm concentration.

EXAMPLE 4

Commercially-available or in-house formulations of other herbicides and antidotes used in Examples 5-13 and Tables 1-9 had the following initial compositions (in weight percent) which were then mixed where desired with an appropriate carrier to provide the desired application rate in kg/ha:

| Herbicide | Active Ingredient | Inerts |
|---|---|---|
| SCEPTER ® Herbicide | 17.3 | 82.7 |
| ARSENAL ® Herbicide | 27.6 | 72.4 |
| ASSERT ® Herbicide | 45.5 | 54.5 |
| PURSUIT ® Herbicide | 25.0 | 75.0 |
| CADRE ® Herbicide | 25.0 | 75.0 |
| Acetochlor | 87.3 | 12.7 |
| Metolachlor | 86.4 | 13.6 |

Antidotes - Formulated in acetone to a concentration corresponding to the application rate per hectare.

EXAMPLE 5

The following procedure shows interaction between a herbicide and an antidote when the antidote is applied in a soil furrow containing crop seed and the herbicide is incorporated in a soil cover layer. Containers were filled and compacted with fumigated silt loam soil to a depth of about 1.3 cm from the top of the container. A first container was designated as an untreated control, a second container was designated as a herbicide control, and a third container was designated as a herbicide+antidote test container. Each container was seeded with crop seed in marked furrows. Antidote compound, dissolved in acetone, was applied directly to the seeded furrows of the third container. Antidote application rate was 0.55 mg active compound per inch of furrow (0.22 mg/cm). This rate was comparable to a plot application rate of 0.28 kilogram per hectare (kg/ha), based on 76 cm (30") spaced-apart furrows. Then, each of the second and third containers was filled and leveled with a cover layer of soil having incorporated therein the selected herbicide at a pre-determined concentration. The first container was filled and leveled with soil containing no herbicide. Pots were overhead irrigated with 0.6 cm (¼"), then placed on a bench in a greenhouse and subirrigated as required for the duration of the test. Plant response was observed about three weeks after initial treatment. Results are reported in Table 1.

TABLE 1

% PLANT INHIBITION AND % SAFENING EFFECT ( )

| HERB. NO. | RATE | ANTIDOTE NO. | RATE | CORN W | CORN WO | PIGWEED REDROOT W | PIGWEED REDROOT WO |
|---|---|---|---|---|---|---|---|
| 1 | 0.14 | 21 | 0.28 | 80 (16) | 95 | 85 (4) | 88 |
| 4 | 0.56 | 21 | 0.28 | 60 (37) | 95 | 90 (0) | 90 |
| 1 | 0.14 | 22 | 0.28 | 75 (22) | 95 | 80 (10) | 88 |
| 4 | 0.56 | 22 | 0.28 | 40 (58) | 95 | 90 (0) | 90 |
| 1 | 0.14 | 23 | 0.28 | 90 (6) | 95 | 80 (10) | 88 |
| 4 | 0.56 | 23 | 0.28 | 95 (0) | 95 | 95 | 90 |
| 1 | 0.14 | 24 | 0.28 | 65 (32) | 95 | 85 (4) | 88 |
| 4 | 0.56 | 24 | 0.28 | 30 (69) | 95 | 90 (0) | 90 |
| 1 | 0.14 | 25 | 0.28 | 90 (6) | 95 | 85 (4) | 88 |
| 4 | 0.56 | 25 | 0.28 | 95 (0) | 95 | 95 | 90 |
| 1 | 0.14 | 26 | 0.28 | 95 (0) | 95 | 80 (10) | 88 |
| 4 | 0.56 | 26 | 0.28 | 95 (0) | 95 | 95 | 90 |

TABLE 1-continued

% PLANT INHIBITION AND % SAFENING EFFECT ( )

| HERB. NO. | RATE | ANTIDOTE NO. | RATE | CORN W | CORN WO | PIGWEED REDROOT W | PIGWEED REDROOT WO |
|---|---|---|---|---|---|---|---|
| 1 | 0.14 | 3 | 0.28 | 95 (0) | 95 | 90 | 88 |
| 4 | 0.56 | 3 | 0.28 | 95 (0) | 95 | 90 (0) | 90 |
| 1 | 0.14 | 27 | 0.28 | 80 (16) | 95 | 90 | 88 |
| 1 | 0.14 | 5 | 0.28 | 95 (0) | 95 | 85 (4) | 88 |
| 4 | 0.56 | 5 | 0.28 | 80 (16) | 95 | 90 (0) | 90 |
| 1 | 0.14 | 28 | 0.28 | 80 (16) | 95 | 90 | 88 |
| 4 | 0.56 | 28 | 0.28 | 75 (22) | 95 | 90 (0) | 90 |
| 1 | 0.14 | 28 | 0.28 | 95 (0) | 95 | 60 (32) | 88 |
| 4 | 0.56 | 20 | 0.28 | 65 (32) | 95 | 95 | 90 |
| 1 | 0.14 | 30 | 0.28 | 95 (0) | 95 | 85 (4) | 88 |
| 4 | 0.56 | 30 | 0.28 | 90 (6) | 95 | 95 | 90 |
| 1 | 0.14 | 31 | 0.28 | 75 (22) | 95 | 85 (4) | 88 |
| 4 | 0.56 | 31 | 0.28 | 80 (16) | 95 | 95 | 90 |
| 1 | 0.14 | 32 | 0.28 | 90 (6) | 95 | 80 (10) | 88 |
| 4 | 0.56 | 32 | 0.28 | 95 (0) | 95 | 90 (0) | 90 |
| 1 | 0.14 | 33 | 0.28 | 95 (0) | 95 | 90 | 88 |
| 4 | 0.56 | 33 | 0.28 | 85 (11) | 95 | 95 | 90 |
| 1 | 0.14 | 34 | 0.28 | 95 (0) | 95 | 80 (10) | 88 |
| 4 | 0.56 | 34 | 0.28 | 75 (22) | 95 | 85 (6) | 90 |
| 1 | 0.14 | 35 | 0.28 | 95 (0) | 95 | 85 (4) | 88 |
| 4 | 0.56 | 35 | 0.28 | 95 (0) | 95 | 90 (0) | 90 |
| 1 | 0.14 | 36 | 0.28 | 100 | 95 | 90 | 88 |
| 4 | 0.56 | 36 | 0.28 | 95 (0) | 95 | 90 (0) | 90 |
| 1 | 0.14 | 37 | 0.28 | 95 (0) | 95 | 60 (32) | 88 |
| 4 | 0.56 | 37 | 0.28 | 95 (0) | 95 | 90 (0) | 90 |
| 1 | 0.14 | 38 | 0.28 | 100 | 95 | 25 (72) | 88 |
| 4 | 0.56 | 38 | 0.28 | 95 (0) | 95 | 90 (0) | 90 |
| 1 | 0.14 | 39 | 0.28 | 95 (0) | 95 | 90 | 88 |
| 4 | 0.56 | 39 | 0.28 | 85 (11) | 95 | 90 (0) | 90 |
| 1 | 0.14 | 40 | 0.28 | 95 (0) | 95 | 85 (4) | 88 |
| 4 | 0.56 | 40 | 0.28 | 75 (22) | 95 | 90 (0) | 90 |
| 1 | 0.14 | 41 | 0.28 | 95 (0) | 95 | 85 (4) | 88 |
| 4 | 0.56 | 41 | 0.28 | 90 (6) | 95 | 85 (6) | 90 |
| 1 | 0.14 | 42 | 0.28 | 95 (0) | 95 | 85 (4) | 88 |
| 4 | 0.56 | 42 | 0.28 | 50 (48) | 95 | 90 (0) | 90 |
| 1 | 0.14 | 43 | 0.28 | 90 (6) | 95 | 85 (4) | 88 |

TABLE 1-continued

| % PLANT INHIBITION AND % SAFENING EFFECT ( ) | | | | | | | |
|---|---|---|---|---|---|---|---|
| HERB. NO. | RATE | ANTI-DOTE NO. | RATE | CORN W | CORN WO | PIGWEED REDROOT W | PIGWEED REDROOT WO |
| 4 | 0.56 | 43 | 0.28 | 60 (37) | 95 | 80 (12) | 90 |
| 1 | 0.14 | 44 | 0.28 | 95 (0) | 95 | 85 (4) | 88 |
| 4 | 0.56 | 44 | 0.28 | 45 (53) | 95 | 90 (0) | 90 |
| 1 | 0.14 | 45 | 0.28 | 95 (0) | 95 | 80 (10) | 88 |
| 4 | 0.56 | 45 | 0.28 | 85 (11) | 95 | 95 | 90 |
| 1 | 0.14 | 46 | 0.28 | 95 (0) | 95 | 80 (10) | 88 |
| 4 | 0.56 | 46 | 0.28 | 95 (0) | 95 | 95 | 90 |
| 1 | 0.14 | 47 | 0.28 | 95 (0) | 95 | 75 (15) | 88 |
| 4 | 0.56 | 47 | 0.28 | 80 (16) | 95 | 90 (0) | 90 |
| 1 | 0.14 | 13 | 0.28 | 80 (16) | 95 | 80 (10) | 88 |
| 4 | 0.56 | 13 | 0.28 | 60 (37) | 95 | 80 (12) | 90 |
| 1 | 0.14 | 48 | 0.28 | 90 (6) | 95 | 85 (4) | 88 |
| 4 | 0.56 | 48 | 0.28 | 80 (16) | 95 | 85 (6) | 90 |
| 1 | 0.14 | 49 | 0.28 | 95 (0) | 95 | 90 | 88 |
| 4 | 0.56 | 49 | 0.28 | 90 (6) | 95 | 85 (6) | 90 |
| 1 | 0.14 | 50 | 0.28 | 100 | 95 | 95 | 88 |
| 4 | 0.56 | 50 | 0.28 | 100 | 95 | 100 | 90 |
| 1 | 0.14 | 51 | 0.28 | 95 (0) | 95 | 90 | 88 |
| 4 | 0.56 | 51 | 0.28 | 95 (0) | 95 | 90 (0) | 90 |
| 1 | 0.14 | 52 | 0.28 | 95 (0) | 95 | 85 (4) | 88 |
| 4 | 0.56 | 52 | 0.28 | 90 (6) | 95 | 90 (0) | 90 |
| 1 | 0.14 | 53 | 0.28 | 95 (0) | 95 | 80 (10) | 88 |
| 4 | 0.56 | 53 | 0.28 | 95 (0) | 95 | 90 (0) | 90 |
| 1 | 0.14 | 54 | 0.28 | 65 (32) | 95 | 85 (4) | 88 |
| 4 | 0.56 | 54 | 0.28 | 15 (85) | 95 | 95 | 90 |
| 1 | 0.14 | 55 | 0.28 | 95 (0) | 95 | 90 | 88 |
| 4 | 0.56 | 55 | 0.28 | 65 (32) | 95 | 90 (0) | 90 |
| 1 | 0.14 | 56 | 0.28 | 80 (16) | 95 | 90 | 88 |
| 4 | 0.56 | 56 | 0.28 | 90 (6) | 95 | 90 (0) | 90 |
| 1 | 0.14 | 57 | 0.28 | 70 (27) | 95 | 80 (10) | 88 |
| 4 | 0.56 | 57 | 0.28 | 55 (43) | 95 | 95 | 90 |
| 1 | 0.14 | 58 | 0.28 | 85 (11) | 95 | 70 (21) | 88 |
| 4 | 0.56 | 58 | 0.28 | 55 (43) | 95 | 95 | 90 |
| 1 | 0.14 | 59 | 0.28 | 75 (22) | 95 | 85 (4) | 88 |
| 4 | 0.56 | 59 | 0.28 | 85 (11) | 95 | 90 (0) | 90 |
| 1 | 0.14 | 60 | 0.28 | 95 (0) | 95 | 80 (10) | 88 |

TABLE 1-continued

| % PLANT INHIBITION AND % SAFENING EFFECT ( ) | | | | | | | |
|---|---|---|---|---|---|---|---|
| HERB. NO. | RATE | ANTI-DOTE NO. | RATE | CORN W | CORN WO | PIGWEED REDROOT W | PIGWEED REDROOT WO |
| 4 | 0.56 | 60 | 0.28 | 60 (37) | 95 | 90 (0) | 90 |
| 1 | 0.14 | 61 | 0.28 | 95 (0) | 95 | 80 (10) | 88 |
| 4 | 0.56 | 61 | 0.28 | 45 (53) | 95 | 80 (12) | 90 |
| 1 | 0.14 | 62 | 0.28 | 95 (0) | 95 | 80 (10) | 88 |
| 4 | 0.56 | 62 | 0.28 | 5 (95) | 95 | 90 (0) | 90 |
| 1 | 0.14 | 63 | 0.28 | 85 (11) | 95 | 90 | 88 |
| 4 | 0.56 | 63 | 0.28 | 25 (74) | 95 | 95 | 90 |
| 1 | 0.14 | 64 | 0.28 | 90 (6) | 95 | 85 (4) | 88 |
| 4 | 0.56 | 64 | 0.28 | 90 (6) | 95 | 85 (6) | 90 |
| 1 | 0.14 | 65 | 0.28 | 95 (0) | 95 | 80 (10) | 88 |
| 4 | 0.56 | 65 | 0.28 | 95 (0) | 95 | 90 (0) | 90 |
| 1 | 0.14 | 66 | 0.28 | 85 (11) | 95 | 85 (4) | 88 |
| 4 | 0.56 | 66 | 0.28 | 90 (6) | 95 | 95 | 90 |
| 1 | 0.14 | 67 | 0.28 | 95 (0) | 95 | 80 (10) | 88 |
| 4 | 0.56 | 67 | 0.28 | 65 (32) | 95 | 90 (0) | 90 |
| 1 | 0.14 | 68 | 0.28 | 95 (0) | 95 | 85 (4) | 88 |
| 4 | 0.56 | 68 | 0.28 | 40 (58) | 95 | 85 (6) | 90 |
| 1 | 0.14 | 69 | 0.28 | 95 (0) | 95 | 90 | 88 |
| 4 | 0.56 | 69 | 0.28 | 80 (16) | 95 | 85 (6) | 90 |
| 1 | 0.14 | 70 | 0.28 | 95 (0) | 95 | 95 | 88 |
| 4 | 0.56 | 70 | 0.28 | 50 (48) | 95 | 95 | 90 |
| 1 | 0.14 | 71 | 0.28 | 90 (6) | 95 | 85 (4) | 88 |
| 4 | 0.56 | 71 | 0.28 | 70 (27) | 95 | 85 (6) | 90 |
| 1 | 0.14 | 72 | 0.28 | 95 (0) | 95 | 95 | 88 |
| 4 | 0.56 | 72 | 0.28 | 75 (22) | 95 | 90 (0) | 90 |
| 1 | 0.14 | 73 | 0.28 | 75 (22) | 95 | 85 (4) | 88 |
| 4 | 0.56 | 73 | 0.28 | 85 (11) | 95 | 90 (0) | 90 |
| 1 | 0.14 | 74 | 0.28 | 80 (16) | 95 | 95 | 88 |
| 4 | 0.56 | 74 | 0.28 | 80 (16) | 95 | 95 | 90 |
| 1 | 0.14 | 75 | 0.28 | 90 (6) | 95 | 85 (4) | 88 |
| 4 | 0.56 | 75 | 0.28 | 90 (6) | 95 | 95 | 90 |
| 1 | 0.14 | 76 | 0.28 | 90 (6) | 95 | 80 (10) | 88 |
| 4 | 0.56 | 76 | 0.28 | 55 (43) | 95 | 90 (0) | 90 |

EXAMPLE 6

The following procedure shows interaction between herbicide and antidote when both are incorporated in a soil cover layer before emergnece of crop and weed species. Containers were filled and compacted with a fumigated silt loam top soil to a depth of about 1.3 cm from the top of the container. A first container was designated as an untreated control, a second container was designated as a herbicide control, and a third container was designated as a herbicide+antidote test container. Each of the containers was seeded with a crop species. A measured amount of herbicide dispersed or dissolved in acetone was applied to a measured quantity of soil. To this same quantity is of soil treated with herbicide, there was added a measured amount of antidote dispersed or dissolved in acetone. The quantity of soil treated with the herbicide and antidote was thoroughly mixed to incorporate the herbicide and antidote in the soil uniformly. The seed bed in the third container of soil was covered with the soil treated with the herbicide and antidote and the container was leveled. For each test series, the seed beds of the first and second containers were likewise covered by soil layers. The cover layer of the first container was not treated with herbicide or antidote. The cover layer of the second container had a measured quantity of herbicide alone incorporated therein. the containers were then placed on a bench in a greenhouse and sub-irrigated as required for the duration of the test. Plant response was observed about three weeks after initial treatment. Results are reported in Table 2.

TABLE 2

| HERB. NO. | RATE | ANTI-DOTE NO. | RATE | SORGHUM GRAIN W | | SORGHUM GRAIN WO | WHEAT W | | WHEAT WO | PIGWEED REDROOT W | | PIGWEED REDROOT WO | CORN W | | CORN WO | TARTARY BUCKWHEAT W | | TARTARY BUCKWHEAT WO | SOYBEAN W | | SOYBEAN WO | RICE W | RICE WO | VELVET LEAF W | VELVET LEAF WO |
|---|---|---|---|---|---|---|---|---|---|---|---|---|---|---|---|---|---|---|---|---|---|---|---|---|---|
| | | | | % PLANT INHIBITION AND % SAFENING EFFECT ( ) | | | | | | | | | | | | | | | | | | | | | |
| 1 | 0.03 | 1 | 0.56 | 15 | (58) | 35 | 30 | (34) | 45 | 80 | | 65 | 25 | (0) | 25 | 25 | (0) | 25 | | | | | | | |
| 1 | 0.14 | 1 | 0.56 | 90 | (6) | 95 | 100 | | 97 | 90 | (0) | 90 | 80 | (0) | 80 | 60 | | 50 | | | | | | | |
| 1 | 0.03 | 1 | 2.24 | 80 | | 35 | 25 | (45) | 45 | 95 | | 65 | 10 | (60) | 25 | 25 | (0) | 25 | | | | | | | |
| 1 | 0.14 | 1 | 2.24 | 60 | (37) | 95 | 85 | (13) | 97 | 95 | | 90 | 75 | (7) | 80 | 40 | (20) | 50 | | | | | | | |
| 1 | 0.03 | 1 | 8.96 | 10 | (72) | 35 | 0 | (100) | 45 | 70 | | 65 | 25 | (0) | 25 | 10 | (60) | 25 | | | | | | | |
| 1 | 0.14 | 1 | 8.96 | 85 | (11) | 95 | 90 | (8) | 97 | 100 | | 90 | 30 | (63) | 80 | 25 | (50) | 50 | | | | | | | |
| 2 | 0.14 | 1 | 0.56 | 60 | | 43 | 90 | (3) | 92 | 35 | (0) | 35 | | | | | | | | | | | | | |
| 2 | 0.14 | 1 | 0.56 | | | | | | | 20 | (67) | 60 | | | | | | | 40 | | 38 | | | | |
| 2 | 0.28 | 1 | 0.56 | | | | | | | 95 | (4) | 98 | 70 | (15) | 82 | | | | | | | | | | |
| 2 | 0.28 | 1 | 0.56 | | | | | | | 70 | | 60 | 65 | (30) | 92 | | | | | | | | | | |
| 2 | 0.56 | 1 | 0.56 | | | | | | | 70 | (18) | 85 | | | | | | | 80 | | 77 | | | | |
| 2 | 0.56 | 1 | 0.56 | 95 | (0) | 95 | 95 | (0) | 95 | 90 | | 80 | | | | | | | | | | | | | |
| 2 | 1.12 | 1 | 0.56 | | | | | | | 100 | (0) | 100 | 100 | (0) | 100 | | | | | | | | | | |
| 2 | 1.12 | 1 | 0.56 | | | | | | | 70 | (0) | 70 | 95 | (5) | 100 | | | | | | | | | | |
| 2 | 0.14 | 1 | 2.24 | 10 | (77) | 43 | 75 | (19) | 92 | 50 | | 35 | | | | | | | | | | | | | |
| 2 | 0.14 | 1 | 2.24 | | | | | | | 0 | (100) | 60 | | | | | | | 65 | | 38 | | | | |
| 2 | 0.28 | 1 | 2.24 | | | | | | | 100 | | 98 | 100 | | 82 | | | | | | | | | | |
| 2 | 0.28 | 1 | 2.24 | | | | | | | 95 | | 60 | 95 | | 92 | | | | | | | | | | |
| 2 | 0.56 | 1 | 2.24 | | | | | | | 95 | | 85 | | | | | | | 95 | | 77 | | | | |
| 2 | 0.56 | 1 | 2.24 | 95 | (0) | 95 | 95 | (0) | 95 | 90 | | 80 | | | | | | | | | | | | | |
| 2 | 1.12 | 1 | 2.24 | | | | | | | 100 | (0) | 100 | 100 | (0) | 100 | | | | | | | | | | |
| 2 | 1.12 | 1 | 2.24 | | | | | | | 55 | (22) | 70 | 100 | (0) | 100 | | | | | | | | | | |
| 2 | 0.14 | 1 | 8.96 | | | | | | | 0 | (100) | 60 | | | | | | | 15 | (61) | 38 | | | | |
| 2 | 0.14 | 1 | 8.96 | 25 | (42) | 43 | 80 | (14) | 92 | 75 | | 35 | | | | | | | | | | | | | |
| 2 | 0.28 | 1 | 8.96 | | | | | | | 95 | (4) | 98 | 100 | | 82 | | | | | | | | | | |

-continued

| | | | | | | | | | | | | | | | | | | | | |
|---|---|---|---|---|---|---|---|---|---|---|---|---|---|---|---|---|---|---|---|---|
| 2 | 0.28 | 1 | 8.96 | | | | | | | 90 | | 60 | 95 | | 92 | | | | | |
| 2 | 0.56 | 1 | 8.96 | | | | | | | 15 | | 85 | | | | | | 75 | | 77 |
| | | | | | | | | | | | (83) | | | | | | | | (3) | |
| 2 | 0.56 | 1 | 8.96 | 85 | | 95 | 95 | | 95 | 30 | | 80 | | | | | | | | |
| | | | | | (1) | | | (0) | | | (63) | | | | | | | | | |
| 2 | 1.12 | 1 | 8.96 | | | | | | | 100 | | 100 | 100 | | 100 | | | | | |
| | | | | | | | | | | | (0) | | | (0) | | | | | | |
| 2 | 1.12 | 1 | 8.96 | | | | | | | 55 | | 70 | 100 | | 100 | | | | | |
| | | | | | | | | | | | (22) | | | (0) | | | | | | |
| 3 | 2.24 | 1 | 0.56 | | | | | | | 15 | | 55 | 5 | | 10 | | | | | |
| | | | | | | | | | | | (73) | | | (50) | | | | | | |
| 3 | 4.48 | 1 | 0.56 | | | | | | | 25 | | 55 | 5 | | 40 | | | | | |
| | | | | | | | | | | | (55) | | | (88) | | | | | | |
| 3 | 2.24 | 1 | 2.24 | | | | | | | 35 | | 55 | 0 | | 10 | | | | | |
| | | | | | | | | | | | (37) | | | (100) | | | | | | |
| 3 | 4.48 | 1 | 2.24 | | | | | | | 15 | | 55 | 5 | | 40 | | | | | |
| | | | | | | | | | | | (73) | | | (88) | | | | | | |
| 3 | 2.24 | 1 | 8.96 | | | | | | | 0 | | 55 | 0 | | 10 | | | | | |
| | | | | | | | | | | | (100) | | | (100) | | | | | | |
| 3 | 4.48 | 1 | 8.96 | | | | | | | 20 | | 55 | 5 | | 40 | | | | | |
| | | | | | | | | | | | (64) | | | (88) | | | | | | |
| 4 | 0.14 | 1 | 0.56 | 95 | | 98 | 95 | | 98 | 90 | | 95 | | | | | | | | |
| | | | | | (4) | | | (4) | | | (6) | | | | | | | | | |
| 4 | 0.56 | 1 | 0.56 | 100 | | 100 | 100 | | 100 | 100 | | 100 | | | | | | | | |
| | | | | | (0) | | | (0) | | | (0) | | | | | | | | | |
| 4 | 0.56 | 1 | 0.56 | | | | | | | 85 | | 80 | 90 | | 90 | | | | | |
| | | | | | | | | | | | | | | (0) | | | | | | |
| 4 | 1.12 | 1 | 0.56 | | | | | | | 80 | | 80 | 90 | | 97 | | | | | |
| | | | | | | | | | | | (0) | | | (8) | | | | | | |
| 4 | 1.12 | 1 | 0.56 | | | | | | | 40 | | 70 | | | | | | 0 | | 7 |
| | | | | | | | | | | | (43) | | | | | | | | (100) | |
| 4 | 2.24 | 1 | 0.56 | | | | | | | 75 | | 73 | | | | | | 10 | | 30 |
| | | | | | | | | | | | | | | | | | | | (67) | |
| 4 | 0.14 | 1 | 2.24 | 100 | | 98 | 100 | | 98 | 95 | | 95 | | | | | | | | |
| | | | | | | | | | | | (0) | | | | | | | | | |
| 4 | 0.56 | 1 | 2.24 | 100 | | 100 | 100 | | 100 | 100 | | 100 | | | | | | | | |
| | | | | | (0) | | | (0) | | | (0) | | | | | | | | | |
| 4 | 0.56 | 1 | 2.24 | | | | | | | 85 | | 80 | 65 | | 90 | | | | | |
| | | | | | | | | | | | | | | (28) | | | | | | |
| 4 | 1.12 | 1 | 2.24 | | | | | | | 80 | | 80 | 80 | | 97 | | | | | |
| | | | | | | | | | | | (0) | | | (18) | | | | | | |
| 4 | 1.12 | 1 | 2.24 | | | | | | | 60 | | 70 | | | | | | 15 | | 7 |
| | | | | | | | | | | | (15) | | | | | | | | | |
| 4 | 2.24 | 1 | 2.24 | | | | | | | 55 | | 73 | | | | | | 20 | | 30 |
| | | | | | | | | | | | (25) | | | | | | | | (34) | |
| 4 | 0.14 | 1 | 8.96 | 95 | | 98 | 90 | | 98 | 95 | | 95 | | | | | | | | |
| | | | | | (4) | | | (9) | | | (0) | | | | | | | | | |
| 4 | 0.56 | 1 | 8.96 | 100 | | 100 | 100 | | 100 | 95 | | 100 | | | | | | | | |
| | | | | | (0) | | | (0) | | | (5) | | | | | | | | | |
| 4 | 0.56 | 1 | 8.96 | | | | | | | 35 | | 80 | 20 | | 90 | | | | | |
| | | | | | | | | | | | (57) | | | (78) | | | | | | |
| 4 | 1.12 | 1 | 8.96 | | | | | | | 85 | | 80 | 90 | | 97 | | | | | |
| | | | | | | | | | | | | | | (8) | | | | | | |
| 4 | 1.12 | 1 | 8.96 | | | | | | | 70 | | 70 | | | | 0 | 7 | | | |

-continued

| | | | | | | | | | | | | | | | | | | | | | | | | |
|---|---|---|---|---|---|---|---|---|---|---|---|---|---|---|---|---|---|---|---|---|---|---|---|---|
| | | | | | | | | | | | (0) | | | | | | (100) | | | | | | | |
| 4 | 2.24 | 1 | 8.96 | | | | | | | 65 | | 73 | | | | | | | 20 | | 30 | | | |
| | | | | | | | | | | | (11) | | | | | | | | | (34) | | | | |
| 5 | 0.14 | 1 | 0.56 | | | | | | | 85 | | 85 | | | | | | | 40 | | 28 | | | |
| | | | | | | | | | | | (0) | | | | | | | | | | | | | |
| 5 | 0.14 | 1 | 0.56 | | | | | | | 50 | | 35 | 0 | | | | | | | | | | | |
| 5 | 0.14 | 1 | 0.56 | | | | 30 | | 32 | 80 | | 60 | | | | | | | | | | 95 | | 100 |
| | | | | | | | | (7) | | | | | | | | | | | | | | | (5) | |
| 5 | 0.56 | 1 | 0.56 | | | | | | | 85 | | 80 | 0 | | 75 | | | | | | | | | |
| | | | | | | | | | | | | | | (100) | | | | | | | | | | |
| 5 | 0.56 | 1 | 0.56 | | | | 90 | | 95 | 95 | | 90 | | | | | | | | | | 100 | | 100 |
| | | | | | | | | (6) | | | | | | | | | | | | | | | (0) | |
| 5 | 0.56 | 1 | 0.56 | | | | | | | 90 | | 90 | | | | | | | 45 | | 50 | | | |
| | | | | | | | | | | | (0) | | | | | | | | | (10) | | | | |
| 5 | 0.14 | 1 | 2.24 | | | | 40 | | 32 | 85 | | 60 | | | | | | | | | | 95 | | 100 |
| | | | | | | | | | | | | | | | | | | | | | | | (5) | |
| 5 | 0.14 | 1 | 2.24 | | | | | | | 60 | | 35 | 5 | | | | | | | | | | | |
| 5 | 0.14 | 1 | 2.24 | | | | | | | 80 | | 85 | | | | | | | 45 | | 28 | | | |
| | | | | | | | | | | | (6) | | | | | | | | | | | | | |
| 5 | 0.56 | 1 | 2.24 | | | | 85 | | 95 | 90 | | 90 | | | | | | | | | | 100 | | 100 |
| | | | | | | | | (11) | | | (0) | | | | | | | | | | | | (0) | |
| 5 | 0.56 | 1 | 2.24 | | | | | | | 85 | | 90 | | | | | | | 80 | | 50 | | | |
| | | | | | | | | | | | (6) | | | | | | | | | | | | | |
| 5 | 0.56 | 1 | 2.24 | | | | | | | 65 | | 80 | 15 | | 75 | | | | | | | | | |
| | | | | | | | | | | | (19) | | | (80) | | | | | | | | | | |
| 5 | 0.14 | 1 | 8.96 | | | | 25 | | 32 | 100 | | 60 | | | | | | | | | | 95 | | 100 |
| | | | | | | | | (22) | | | | | | | | | | | | | | | (5) | |
| 5 | 0.14 | 1 | 8.96 | | | | | | | 25 | | 35 | 0 | | | | | | | | | | | |
| | | | | | | | | | | | (29) | | | | | | | | | | | | | |
| 5 | 0.14 | 1 | 8.96 | | | | | | | 20 | | 85 | | | | | | | 5 | | 28 | | | |
| | | | | | | | | | | | (77) | | | | | | | | | (83) | | | | |
| 5 | 0.56 | 1 | 8.96 | | | | 95 | | 95 | 90 | | 90 | | | | | | | | | | 100 | | 100 |
| | | | | | | | | (0) | | | (0) | | | | | | | | | | | | (0) | |
| 5 | 0.56 | 1 | 8.96 | | | | | | | 85 | | 90 | | | | | | | 25 | | 50 | | | |
| | | | | | | | | | | | (6) | | | | | | | | | (50) | | | | |
| 5 | 0.56 | 1 | 8.96 | | | | | | | 65 | | 80 | 0 | | 75 | | | | | | | | | |
| | | | | | | | | | | | (19) | | | (100) | | | | | | | | | | |
| 1 | 0.03 | 2 | 0.56 | 0 | | 35 | 15 | | 45 | 85 | | 65 | 0 | | 25 | 40 | | 25 | | | | | | |
| | | | | | (100) | | | (67) | | | | | | (100) | | | | | | | | | | |
| 1 | 0.14 | 2 | 0.56 | 60 | | 95 | 95 | | 97 | 95 | | 90 | 65 | | 80 | 65 | | 50 | | | | | | |
| | | | | | (37) | | | (3) | | | | | | (19) | | | | | | | | | | |
| 1 | 0.03 | 2 | 2.24 | 20 | | 35 | 10 | | 45 | 95 | | 65 | 5 | | 25 | 20 | | 25 | | | | | | |
| | | | | | (43) | | | (78) | | | | | | (80) | | | (20) | | | | | | | |
| 1 | 0.14 | 2 | 2.24 | 60 | | 95 | 95 | | 97 | 95 | | 90 | 70 | | 80 | 55 | | 50 | | | | | | |
| | | | | | (37) | | | (3) | | | | | | (13) | | | | | | | | | | |
| 1 | 0.03 | 2 | 8.96 | 10 | | 35 | 10 | | 45 | 85 | | 65 | 15 | | 25 | 15 | | 25 | | | | | | |
| | | | | | (72) | | | (78) | | | | | | (40) | | | (40) | | | | | | | |
| 1 | 0.14 | 2 | 8.96 | 45 | | 95 | 60 | | 97 | 95 | | 90 | 50 | | 80 | 50 | | 50 | | | | | | |
| | | | | | (53) | | | (39) | | | | | | (38) | | | (0) | | | | | | | |
| 2 | 0.14 | 2 | 0.56 | 0 | | 43 | 95 | | 92 | 40 | | 35 | | | | | | | | | | | | |
| | | | | | (100) | | | | | | | | | | | | | | | | | | | |
| 2 | 0.14 | 2 | 0.56 | | | | | | | 75 | | 60 | | | | | | | 60 | | 38 | | | |
| 2 | 0.28 | 2 | 0.56 | | | | | | | 100 | | 98 | 100 | | 82 | | | | | | | | | |
| 2 | 0.28 | 2 | 0.56 | | | | | | | 80 | | 60 | 90 | | 92 | | | | | | | | | |

-continued

| | | | | | | | | | | | | | | (3) | | | | |
|---|---|---|---|---|---|---|---|---|---|---|---|---|---|---|---|---|---|---|
| 2 | 0.56 | 2 | 0.56 | 95 | (0) | 95 | 95 | (0) | 95 | 30 | (63) | 80 | | | | | | |
| 2 | 0.56 | 2 | 0.56 | | | | | | | 15 | (83) | 85 | | | | 65 | (16) | 77 |
| 2 | 1.12 | 2 | 0.56 | | | | | | | 100 | (0) | 100 | 100 | (0) | 100 | | | |
| 2 | 1.12 | 2 | 0.56 | | | | | | | 95 | | 70 | 95 | (5) | 100 | | | |
| 2 | 0.14 | 2 | 2.24 | 25 | (42) | 43 | 90 | (3) | 92 | 20 | (43) | 35 | | | | | | |
| 2 | 0.14 | 2 | 2.24 | | | | | | | 25 | (59) | 60 | | | | 40 | | 38 |
| 2 | 0.28 | 2 | 2.24 | | | | | | | 100 | | 98 | 100 | | 82 | | | |
| 2 | 0.28 | 2 | 2.24 | | | | | | | 65 | | 60 | 95 | | 92 | | | |
| 2 | 0.56 | 2 | 2.24 | 95 | (0) | 95 | 95 | (0) | 95 | 70 | (13) | 80 | | | | | | |
| 2 | 0.56 | 2 | 2.24 | | | | | | | 95 | | 85 | | | | 95 | | 77 |
| 2 | 1.12 | 2 | 2.24 | | | | | | | 100 | (0) | 100 | 100 | (0) | 100 | | | |
| 2 | 1.12 | 2 | 2.24 | | | | | | | 85 | | 70 | 100 | (0) | 100 | | | |
| 2 | 0.14 | 2 | 8.96 | 0 | (100) | 43 | 15 | (84) | 92 | 0 | (100) | 35 | | | | | | |
| 2 | 0.14 | 2 | 8.96 | | | | | | | 0 | (100) | 60 | | | | 0 | (100) | 38 |
| 2 | 0.28 | 2 | 8.96 | | | | | | | 95 | (4) | 98 | 100 | | 82 | | | |
| 2 | 0.28 | 2 | 8.96 | | | | | | | 55 | (9) | 60 | 70 | (24) | 92 | | | |
| 2 | 0.56 | 2 | 8.96 | 95 | (0) | 95 | 95 | (0) | 95 | 100 | | 80 | | | | | | |
| 2 | 0.56 | 2 | 8.96 | | | | | | | 0 | (100) | 85 | | | | 85 | | 77 |
| 2 | 1.12 | 2 | 8.96 | | | | | | | 100 | (0) | 100 | 100 | (0) | 100 | | | |
| 2 | 1.12 | 2 | 8.96 | | | | | | | 90 | | 70 | 95 | (5) | 100 | | | |
| 3 | 2.24 | 2 | 0.56 | | | | | | | 45 | (19) | 55 | 55 | | 10 | | | |
| 3 | 4.48 | 2 | 0.56 | | | | | | | 65 | | 55 | 75 | | 40 | | | |
| 3 | 2.24 | 2 | 2.24 | | | | | | | 0 | (100) | 55 | 50 | | 10 | | | |
| 3 | 4.48 | 2 | 2.24 | | | | | | | 85 | | 55 | 65 | | 40 | | | |
| 3 | 2.24 | 2 | 8.96 | | | | | | | 65 | | 55 | 90 | | 10 | | | |
| 3 | 4.48 | 2 | 8.96 | | | | | | | 70 | | 55 | 5 | (88) | 40 | | | |
| 4 | 0.14 | 2 | 0.56 | 100 | | 98 | 100 | | 98 | 95 | (0) | 95 | | | | | | |
| 4 | 0.56 | 2 | 0.56 | 100 | (0) | 100 | 100 | (0) | 100 | 100 | (0) | 100 | | | | | | |
| 4 | 0.56 | 2 | 0.56 | | | | | | | 80 | (0) | 80 | 95 | | 90 | | | |
| 4 | 1.12 | 2 | 0.56 | | | | | | | 85 | | 80 | 95 | | 97 | | | |

-continued

| | | | | | | | | | | | | | | (3) | | | | | | | | |
|---|---|---|---|---|---|---|---|---|---|---|---|---|---|---|---|---|---|---|---|---|---|---|
| 4 | 1.12 | 2 | 0.56 | | | | | | | 80 | | 70 | | | | 20 | | 7 | | | | |
| 4 | 2.24 | 2 | 0.56 | | | | | | | 75 | | 73 | | | | 35 | | 30 | | | | |
| 4 | 0.14 | 2 | 2.24 | 95 | | 98 | 95 | | 98 | 100 | | 95 | | | | | | | | | | |
| | | | | | (4) | | | (4) | | | | | | | | | | | | | | |
| 4 | 0.56 | 2 | 2.24 | 100 | | 100 | 100 | | 100 | 95 | | 100 | | | | | | | | | | |
| | | | | | (0) | | | (0) | | | (5) | | | | | | | | | | | |
| 4 | 0.56 | 2 | 2.24 | | | | | | | 65 | | 80 | 15 | | 90 | | | | | | | |
| | | | | | | | | | | | (19) | | | (84) | | | | | | | | |
| 4 | 1.12 | 2 | 2.24 | | | | | | | 75 | | 80 | 95 | | 97 | | | | | | | |
| | | | | | | | | | | | (7) | | | (3) | | | | | | | | |
| 4 | 1.12 | 2 | 2.24 | | | | | | | 65 | | 70 | | | | 5 | | 7 | | | | |
| | | | | | | | | | | | (8) | | | | | | (29) | | | | | |
| 4 | 2.24 | 2 | 2.24 | | | | | | | 60 | | 73 | | | | 5 | | 30 | | | | |
| | | | | | | | | | | | (18) | | | | | | (84) | | | | | |
| 4 | 0.14 | 2 | 8.96 | 95 | | 98 | 100 | | 98 | 95 | | 95 | | | | | | | | | | |
| | | | | | (4) | | | | | | (0) | | | | | | | | | | | |
| 4 | 0.56 | 2 | 8.96 | 100 | | 100 | 100 | | 100 | 100 | | 100 | | | | | | | | | | |
| | | | | | (0) | | | (0) | | | (0) | | | | | | | | | | | |
| 4 | 0.56 | 2 | 8.96 | | | | | | | 90 | | 80 | 20 | | 90 | | | | | | | |
| | | | | | | | | | | | | | | (78) | | | | | | | | |
| 4 | 1.12 | 2 | 8.96 | | | | | | | 70 | | 80 | 75 | | 97 | | | | | | | |
| | | | | | | | | | | | (13) | | | (23) | | | | | | | | |
| 4 | 1.12 | 2 | 8.96 | | | | | | | 75 | | 70 | | | | 25 | | 7 | | | | |
| 4 | 2.24 | 2 | 8.96 | | | | | | | 60 | | 73 | | | | 0 | | 30 | | | | |
| | | | | | | | | | | | (18) | | | | | | (100) | | | | | |
| 4 | 0.14 | 2 | 0.56 | | | | | | | 55 | | 85 | | | | 55 | | 28 | | | | |
| | | | | | | | | | | | (36) | | | | | | | | | | | |
| 5 | 0.14 | 2 | 0.56 | | | | | | | 60 | | 35 | 0 | | | | | | | | | |
| 5 | 0.14 | 2 | 0.56 | | | | 15 | | 32 | 80 | | 60 | | | | | | | 95 | | 100 | |
| | | | | | | | | | | | | (54) | | | | | | | | | | (5) |
| 5 | 0.56 | 2 | 0.56 | | | | 95 | | 95 | 85 | | 90 | | | | | | | 95 | | 100 | |
| | | | | | | | | (0) | | | (6) | | | | | | | | | (5) | | |
| 5 | 0.56 | 2 | 0.56 | | | | | | | 85 | | 90 | | | | 60 | | 50 | | | | |
| | | | | | | | | | | | (6) | | | | | | | | | | | |
| 5 | 0.56 | 2 | 0.56 | | | | | | | 75 | | 80 | 0 | | 75 | | | | | | | |
| | | | | | | | | | | | (7) | | | (100) | | | | | | | | |
| 5 | 0.14 | 2 | 2.24 | | | | | | | 60 | | 35 | 0 | | | | | | | | | |
| 5 | 0.14 | 2 | 2.24 | | | | | | | 60 | | 85 | | | | 40 | | 28 | | | | |
| | | | | | | | | | | | (30) | | | | | | | | | | | |
| 5 | 0.14 | 2 | 2.24 | | | | 15 | | 32 | 85 | | 60 | | | | | | | 90 | | 100 | |
| | | | | | | | | (54) | | | | | | | | | | | | (10) | | |
| 5 | 0.56 | 2 | 2.24 | | | | 90 | | 95 | 95 | | 90 | | | | | | | 100 | | 100 | |
| | | | | | | | | (6) | | | | | | | | | | | | (0) | | |
| 5 | 0.56 | 2 | 2.24 | | | | | | | 100 | | 80 | 0 | | 75 | | | | | | | |
| | | | | | | | | | | | | | | (100) | | | | | | | | |
| 5 | 0.56 | 2 | 2.24 | | | | | | | 90 | | 90 | | | | 30 | | 50 | | | | |
| | | | | | | | | | | | (0) | | | | | | (40) | | | | | |
| 5 | 0.14 | 2 | 8.96 | | | | | | | 65 | | 85 | | | | 40 | | 28 | | | | |
| | | | | | | | | | | | (24) | | | | | | | | | | | |
| 5 | 0.14 | 2 | 8.96 | | | | | | | 35 | | 35 | 0 | | | | | | | | | |
| | | | | | | | | | | | (0) | | | | | | | | | | | |
| 5 | 0.14 | 2 | 8.96 | | | | 30 | | 32 | 70 | | 60 | | | | | | | 95 | | 100 | |
| | | | | | | | | (7) | | | | | | | | | | | | (5) | | |

-continued

| | | | | | | | | | | | | | | | | | | | | | |
|---|---|---|---|---|---|---|---|---|---|---|---|---|---|---|---|---|---|---|---|---|---|
| 5 | 0.56 | 2 | 8.96 | | | | | | | 90 | (0) | 90 | | | | 45 | (10) | 50 | | | |
| 5 | 0.56 | 2 | 8.96 | | | | 85 | (11) | 95 | 90 | (0) | 90 | | | | | | | 100 | (0) | 100 |
| 5 | 0.56 | 2 | 8.96 | | | | | | | 70 | (13) | 80 | 25 | (67) | 75 | | | | | | |
| 2 | 0.14 | 3 | 0.56 | | | | | | | 25 | (59) | 60 | | | | 50 | | 38 | | | |
| 2 | 0.14 | 3 | 0.56 | 60 | | 43 | 85 | (8) | 92 | 50 | | 35 | | | | | | | | | |
| 2 | 0.28 | 3 | 0.56 | | | | | | | 95 | (4) | 98 | 95 | | 82 | | | | | | |
| 2 | 0.28 | 3 | 0.56 | | | | | | | 85 | | 60 | 90 | (3) | 92 | | | | | | |
| 2 | 0.56 | 3 | 0.56 | | | | | | | 0 | (100) | 85 | | | | 70 | (10) | 77 | | | |
| 2 | 0.56 | 3 | 0.56 | 95 | (0) | 95 | 95 | (0) | 95 | 85 | | 80 | | | | | | | | | |
| 2 | 1.12 | 3 | 0.56 | | | | | | | 95 | (5) | 100 | 100 | (0) | 100 | | | | | | |
| 2 | 1.12 | 3 | 0.56 | | | | | | | 80 | | 70 | 100 | (0) | 100 | | | | | | |
| 2 | 0.14 | 3 | 2.24 | 0 | (100) | 43 | 25 | (73) | 92 | 35 | (0) | 35 | | | | | | | | | |
| 2 | 0.14 | 3 | 2.24 | | | | | | | 25 | (59) | 60 | | | | 5 | (87) | 38 | | | |
| 2 | 0.28 | 3 | 2.24 | | | | | | | 95 | (4) | 98 | 100 | | 82 | | | | | | |
| 2 | 0.28 | 3 | 2.24 | | | | | | | 70 | | 60 | 95 | | 92 | | | | | | |
| 2 | 0.56 | 3 | 2.24 | | | | | | | 85 | (0) | 85 | | | | 90 | | 77 | | | |
| 2 | 0.56 | 3 | 2.24 | 95 | (0) | 95 | 95 | (0) | 95 | 90 | | 80 | | | | | | | | | |
| 2 | 1.12 | 3 | 2.24 | | | | | | | 95 | (5) | 100 | 100 | (0) | 100 | | | | | | |
| 2 | 1.12 | 3 | 2.24 | | | | | | | 90 | | 70 | 100 | (0) | 100 | | | | | | |
| 2 | 0.14 | 3 | 8.96 | 10 | (77) | 43 | 85 | (8) | 92 | 65 | | 35 | | | | | | | | | |
| 2 | 0.14 | 3 | 8.96 | | | | | | | 0 | (100) | 60 | | | | 40 | | 38 | | | |
| 2 | 0.28 | 3 | 8.96 | | | | | | | 100 | | 98 | 90 | | 82 | | | | | | |
| 2 | 0.28 | 3 | 8.96 | | | | | | | 70 | | 60 | 75 | (19) | 92 | | | | | | |
| 2 | 0.56 | 3 | 8.96 | | | | | | | 95 | | 85 | | | | 60 | (23) | 77 | | | |
| 2 | 0.56 | 3 | 8.96 | 70 | (27) | 95 | 95 | (0) | 95 | 75 | (7) | 80 | | | | | | | | | |
| 2 | 1.12 | 3 | 8.96 | | | | | | | 100 | (0) | 100 | 100 | (0) | 100 | | | | | | |
| 2 | 1.12 | 3 | 8.96 | | | | | | | 90 | | 70 | 95 | (5) | 100 | | | | | | |
| 3 | 2.24 | 3 | 0.56 | | | | | | | 75 | | 55 | 80 | | 10 | | | | | | |
| 3 | 4.48 | 3 | 0.56 | | | | | | | 80 | | 55 | 10 | | 40 | | | | | | |

-continued

| | | | | | | | | | | | | | | | | | | | | | |
|---|---|---|---|---|---|---|---|---|---|---|---|---|---|---|---|---|---|---|---|---|---|
| 3 | 2.24 | 3 | 2.24 | | | | | | | 80 | | 55 | 10 | (75) | 10 | | | | | | |
| 3 | 4.48 | 3 | 2.24 | | | | | | | 85 | | 55 | 15 | (0) | 40 | | | | | | |
| 3 | 2.24 | 3 | 8.96 | | | | | | | 40 | | 55 | 5 | (63) | 10 | | | | | | |
| 3 | 4.48 | 3 | 8.96 | | | | | | | 45 | (28) | 55 | 60 | (50) | 40 | | | | | | |
| 4 | 0.14 | 3 | 0.56 | 100 | | 98 | 95 | | 98 | 95 | (19) | 95 | | | | | | | | | |
| 4 | 0.56 | 3 | 0.56 | 100 | | 100 | 100 | (4) | 100 | 95 | (0) | 100 | | | | | | | | | |
| 4 | 0.56 | 3 | 0.56 | | (0) | | | (0) | | 90 | (5) | 80 | 55 | | 90 | | | | | | |
| 4 | 1.12 | 3 | 0.56 | | | | | | | 70 | | 80 | 95 | (39) | 97 | | | | | | |
| 4 | 1.12 | 3 | 0.56 | | | | | | | 60 | (13) | 70 | | (3) | | 45 | | 7 | | | |
| 4 | 2.24 | 3 | 0.56 | | | | | | | 80 | (15) | 73 | | | | 15 | | 30 | | | |
| 4 | 0.14 | 3 | 2.24 | 100 | | 98 | 90 | | 98 | 100 | | 95 | | | | | (50) | | | | |
| 4 | 0.56 | 3 | 2.24 | | | | | (9) | | 85 | | 80 | 70 | | 90 | | | | | | |
| 4 | 0.56 | 3 | 2.24 | 100 | | 100 | 100 | | 100 | 95 | | 100 | | (23) | | | | | | | |
| 4 | 1.12 | 3 | 2.24 | | (0) | | | (0) | | 90 | (5) | 80 | 95 | | 97 | | | | | | |
| 4 | 1.12 | 3 | 2.24 | | | | | | | 55 | | 70 | | (3) | | 15 | | 7 | | | |
| 4 | 2.24 | 3 | 2.24 | | | | | | | 60 | (22) | 73 | | | | 0 | | 30 | | | |
| 4 | 0.14 | 3 | 8.96 | 95 | | 98 | 100 | | 98 | 100 | (18) | 95 | | | | | (100) | | | | |
| 4 | 0.56 | 3 | 8.96 | | (4) | | | | | 90 | | 80 | 60 | | 90 | | | | | | |
| 4 | 0.56 | 3 | 8.96 | 100 | | 100 | 100 | | 100 | 100 | | 100 | | (34) | | | | | | | |
| 4 | 1.12 | 3 | 8.96 | | (0) | | | (0) | | 90 | (0) | 80 | 90 | | 97 | | | | | | |
| 4 | 1.12 | 3 | 8.96 | | | | | | | 90 | | 70 | | (8) | | 20 | | 7 | | | |
| 4 | 2.24 | 3 | 8.96 | | | | | | | 75 | | 73 | | | | 35 | | 30 | | | |
| 5 | 0.14 | 3 | 0.56 | | | | | | | 60 | | 35 | 0 | | | | | | | | |
| 5 | 0.14 | 3 | 0.56 | | | | | | | 35 | | 85 | | | | 45 | | 28 | | | |
| 5 | 0.14 | 3 | 0.56 | | | | 0 | | 32 | 80 | (59) | 60 | | | | | | | 95 | | 100 |
| 5 | 0.56 | 3 | 0.56 | | | | | (100) | | 75 | | 80 | 75 | | 75 | | | | | (5) | |
| 5 | 0.56 | 3 | 0.56 | | | | 95 | | 95 | 85 | (7) | 90 | | (0) | | | | | 100 | | 100 |
| 5 | 0.56 | 3 | 0.56 | | | | | (0) | | 95 | (6) | 90 | | | | 40 | (20) | 50 | | (0) | |

-continued

| | | | | | | | | | | | | | | | | | | | | | | | | |
|---|---|---|---|---|---|---|---|---|---|---|---|---|---|---|---|---|---|---|---|---|---|---|---|---|
| 5 | 0.14 | 3 | 2.24 | | | | | | | 70 | | 35 | 0 | | | | | | | | | | | |
| 5 | 0.14 | 3 | 2.24 | 30 | (7) | 32 | 50 | (17) | 60 | | | | | | | | | | 95 | (5) | 100 | | | |
| 5 | 0.14 | 3 | 2.24 | | | | | | | 50 | (42) | 85 | | | | | | | 60 | | 28 | | | |
| 5 | 0.56 | 3 | 2.24 | | | | 75 | (22) | 95 | 85 | (6) | 90 | | | | | | | | | | 0 | (100) | 100 |
| 5 | 0.56 | 3 | 2.24 | | | | | | | 80 | (12) | 90 | | | | | | | 40 | (20) | 50 | | | |
| 5 | 0.56 | 3 | 2.24 | | | | | | | 75 | (7) | 80 | 35 | (54) | 75 | | | | | | | | | |
| 5 | 0.14 | 3 | 8.96 | | | | | | | 60 | (30) | 85 | | | | | | | 60 | | 28 | | | |
| 5 | 0.14 | 3 | 8.96 | | | | | | | 70 | | 35 | 0 | | | | | | | | | | | |
| 5 | 0.14 | 3 | 8.96 | | | | 50 | | 32 | 65 | | 60 | | | | | | | | | | 85 | (15) | 100 |
| 5 | 0.56 | 3 | 8.96 | | | | | | | 80 | (0) | 80 | 50 | (34) | 75 | | | | | | | | | |
| 5 | 0.56 | 3 | 8.96 | | | | 90 | (6) | 95 | 90 | (0) | 90 | | | | | | | | | | 100 | (0) | 100 |
| 5 | 0.56 | 3 | 8.96 | | | | | | | 90 | (0) | 90 | | | | | | | 30 | (40) | 50 | | | |
| 1 | 0.03 | 4 | 0.56 | 5 | (86) | 35 | 0 | (100) | 45 | 95 | | 65 | 30 | | 25 | 15 | (40) | 25 | | | | | | |
| 1 | 0.14 | 4 | 0.56 | 95 | (0) | 95 | 95 | (3) | 97 | 95 | | 90 | 75 | (7) | 80 | 50 | (0) | 50 | | | | | | |
| 1 | 0.03 | 4 | 2.24 | 0 | (100) | 35 | 0 | (100) | 45 | 85 | | 65 | 45 | | 25 | 25 | (0) | 25 | | | | | | |
| 1 | 0.14 | 4 | 2.24 | 75 | (22) | 95 | 85 | (13) | 97 | 100 | | 90 | 15 | (82) | 80 | 20 | (60) | 50 | | | | | | |
| 1 | 0.03 | 4 | 8.96 | 10 | (72) | 35 | 0 | (100) | 45 | 85 | | 65 | 15 | (40) | 25 | 10 | (60) | 25 | | | | | | |
| 1 | 0.14 | 4 | 8.96 | 5 | (95) | 95 | 80 | (18) | 97 | 100 | | 90 | 30 | (63) | 80 | 30 | (40) | 50 | | | | | | |
| 2 | 0.14 | 4 | 0.56 | | | | | | | 80 | | 60 | | | | | | | 65 | | 38 | | | |
| 2 | 0.14 | 4 | 0.56 | 95 | | 43 | 95 | | 92 | 95 | | 35 | | | | | | | | | | | | |
| 2 | 0.28 | 4 | 0.56 | | | | | | | 95 | (4) | 98 | 100 | | 82 | | | | | | | | | |
| 2 | 0.28 | 4 | 0.56 | | | | | | | 80 | | 60 | 95 | | 92 | | | | | | | | | |
| 2 | 0.56 | 4 | 0.56 | | | | | | | 50 | (42) | 85 | | | | | | | 85 | | 77 | | | |
| 2 | 0.56 | 4 | 0.56 | 90 | (6) | 95 | 95 | (0) | 95 | 85 | | 80 | | | | | | | | | | | | |
| 2 | 1.12 | 4 | 0.56 | | | | | | | 100 | (0) | 100 | 100 | (0) | 100 | | | | | | | | | |
| 2 | 1.12 | 4 | 0.56 | | | | | | | 80 | | 70 | 100 | (0) | 100 | | | | | | | | | |
| 2 | 0.14 | 4 | 2.24 | 30 | (31) | 43 | 70 | (24) | 92 | 10 | (72) | 35 | | | | | | | | | | | | |
| 2 | 0.14 | 4 | 2.24 | | | | | | | 100 | | 60 | | | | | | | 55 | | 38 | | | |
| 2 | 0.28 | 4 | 2.24 | | | | | | | 95 | (4) | 98 | 95 | | 82 | | | | | | | | | |
| 2 | 0.28 | 4 | 2.24 | | | | | | | 75 | | 60 | 100 | | 92 | | | | | | | | | |
| 2 | 0.56 | 4 | 2.24 | | | | | | | 95 | | 85 | | | | | | | 95 | | 77 | | | |

-continued

| | | | | | | | | | | | | | | | | | | |
|---|---|---|---|---|---|---|---|---|---|---|---|---|---|---|---|---|---|---|
| 2 | 0.56 | 4 | 2.24 | 95 | (0) | 95 | 95 | (0) | 95 | 90 | | 80 | | | | | | |
| 2 | 1.12 | 4 | 2.24 | | | | | | | 95 | (5) | 100 | 100 | (0) | 100 | | | |
| 2 | 1.12 | 4 | 2.24 | | | | | | | 40 | (43) | 70 | 95 | (5) | 100 | | | |
| 2 | 0.14 | 4 | 8.96 | 45 | | 43 | 90 | (3) | 92 | 85 | | 35 | | | | | | |
| 2 | 0.14 | 4 | 8.96 | | | | | | | 10 | (84) | 60 | 45 | | 38 | | | |
| 2 | 0.28 | 4 | 8.96 | | | | | | | 95 | (4) | 98 | 100 | | 82 | | | |
| 2 | 0.28 | 4 | 8.96 | | | | | | | 70 | | 60 | 85 | (8) | 92 | | | |
| 2 | 0.56 | 4 | 8.96 | | | | | | | 85 | (0) | 85 | | | | 90 | | 77 |
| 2 | 0.56 | 4 | 8.96 | 95 | (0) | 95 | 95 | (0) | 95 | 95 | | 80 | | | | | | |
| 2 | 1.12 | 4 | 8.96 | | | | | | | 95 | (5) | 100 | 100 | (0) | 100 | | | |
| 2 | 1.12 | 4 | 8.96 | | | | | | | 60 | (15) | 70 | 100 | (0) | 100 | | | |
| 3 | 2.24 | 4 | 0.56 | | | | | | | 15 | (73) | 55 | 40 | | 10 | | | |
| 3 | 4.48 | 4 | 0.56 | | | | | | | 25 | (55) | 55 | 55 | | 40 | | | |
| 3 | 2.24 | 4 | 2.24 | | | | | | | 10 | (82) | 55 | 10 | (0) | 10 | | | |
| 3 | 4.48 | 4 | 2.24 | | | | | | | 60 | | 55 | 55 | | 40 | | | |
| 3 | 2.24 | 4 | 8.96 | | | | | | | 55 | (0) | 55 | 45 | | 10 | | | |
| 3 | 4.48 | 4 | 8.96 | | | | | | | 25 | (55) | 55 | 75 | | 40 | | | |
| 4 | 0.14 | 4 | 0.56 | 95 | (4) | 98 | 100 | | 98 | 95 | (0) | 95 | | | | | | |
| 4 | 0.56 | 4 | 0.56 | 100 | (0) | 100 | 100 | (0) | 100 | 100 | (0) | 100 | | | | | | |
| 4 | 0.56 | 4 | 0.56 | | | | | | | 80 | (0) | 80 | 75 | (17) | 90 | | | |
| 4 | 1.12 | 4 | 0.56 | | | | | | | 85 | | 80 | 85 | (13) | 97 | | | |
| 4 | 1.12 | 4 | 0.56 | | | | | | | 65 | (8) | 70 | | | | 15 | | 7 |
| 4 | 2.24 | 4 | 0.56 | | | | | | | 35 | (53) | 73 | | | | 25 | (17) | 30 |
| 4 | 0.14 | 4 | 2.24 | 95 | (4) | 98 | 95 | (4) | 98 | 95 | (0) | 95 | | | | | | |
| 4 | 0.56 | 4 | 2.24 | 100 | (0) | 100 | 100 | (0) | 100 | 95 | (5) | 100 | | | | | | |
| 4 | 0.56 | 4 | 2.24 | | | | | | | 80 | (0) | 80 | 65 | (28) | 90 | | | |
| 4 | 1.12 | 4 | 2.24 | | | | | | | 50 | (38) | 80 | 85 | (13) | 97 | | | |
| 4 | 1.12 | 4 | 2.24 | | | | | | | 75 | | 70 | | | | 0 | | 7 |

-continued

| | | | | | | | | | | | | | | | | | | | | | |
|---|---|---|---|---|---|---|---|---|---|---|---|---|---|---|---|---|---|---|---|---|---|
| 4 | 2.24 | 4 | 2.24 | | | | | | | 65 | (11) | 73 | | | | 20 | (100) (34) | 30 | | | |
| 4 | 0.14 | 4 | 8.96 | 95 | (4) | 98 | 90 | (9) | 98 | 95 | (0) | 95 | | | | | | | | | |
| 4 | 0.56 | 4 | 8.96 | | | | | | | 85 | | 80 | 0 | (100) | 90 | | | | | | |
| 4 | 0.56 | 4 | 8.96 | 100 | (0) | 100 | 100 | (0) | 100 | 95 | (5) | 100 | | | | | | | | | |
| 4 | 1.12 | 4 | 8.96 | | | | | | | 90 | | 80 | 65 | (33) | 97 | | | | | | |
| 4 | 1.12 | 4 | 8.96 | | | | | | | 65 | (8) | 70 | | | | 25 | | 7 | | | |
| 4 | 2.24 | 4 | 8.96 | | | | | | | 65 | (11) | 73 | | | | 60 | | 30 | | | |
| 5 | 0.14 | 4 | 0.56 | | | | | | | 50 | | 35 | 5 | | | | | | | | |
| 5 | 0.14 | 4 | 0.56 | | | | 35 | | 32 | 10 | (84) | 60 | | | | | | | 80 | (20) | 100 |
| 5 | 0.14 | 4 | 0.56 | | | | | | | 55 | (36) | 85 | | | | 40 | | 28 | | | |
| 5 | 0.56 | 4 | 0.56 | | | | | | | 70 | (13) | 80 | 0 | (100) | 75 | | | | | | |
| 5 | 0.56 | 4 | 0.56 | | | | 80 | (16) | 95 | 80 | (12) | 90 | | | | | | | 100 | (0) | 100 |
| 5 | 0.56 | 4 | 0.56 | | | | | | | 75 | (17) | 90 | | | | 80 | | 50 | | | |
| 5 | 0.14 | 4 | 2.24 | | | | | | | 65 | | 35 | 0 | | | | | | | | |
| 5 | 0.14 | 4 | 2.24 | | | | 30 | (7) | 32 | 15 | (75) | 60 | | | | | | | 95 | (5) | 100 |
| 5 | 0.14 | 4 | 2.24 | | | | | | | 70 | (18) | 85 | | | | 40 | | 28 | | | |
| 5 | 0.56 | 4 | 2.24 | | | | | | | 65 | (19) | 80 | 0 | (100) | 75 | | | | | | |
| 5 | 0.56 | 4 | 2.24 | | | | | | | 85 | (6) | 90 | | | | 35 | (30) | 50 | | | |
| 5 | 0.56 | 4 | 2.24 | | | | 85 | (11) | 95 | 80 | (12) | 90 | | | | | | | 100 | (0) | 100 |
| 5 | 0.14 | 4 | 8.96 | | | | 45 | | 32 | 85 | | 60 | | | | | | | 95 | (5) | 100 |
| 5 | 0.14 | 4 | 8.96 | | | | | | | 50 | | 35 0 | | | | | | | | | |
| 5 | 0.14 | 4 | 8.96 | | | | | | | 65 | (24) | 85 | | | | 60 | | 28 | | | |
| 5 | 0.56 | 4 | 8.96 | | | | | | | 65 | (19) | 80 | 10 | (87) | 75 | | | | | | |
| 5 | 0.56 | 4 | 8.96 | | | | 70 | (27) | 95 | 85 | (6) | 90 | | | | | | | 95 | (5) | 100 |
| 5 | 0.56 | 4 | 8.96 | | | | | | | 80 | (12) | 90 | | | | 35 | (30) | 50 | | | |
| 2 | 0.14 | 5 | 0.56 | 25 | (42) | 43 | 95 | | 92 | 90 | | 35 | | | | | | | | | |
| 2 | 0.14 | 5 | 0.56 | | | | | | | 95 | | 60 | | | | 90 | | 38 | | | |
| 2 | 0.28 | 5 | 0.56 | | | | | | | 75 | | 60 | 95 | | 92 | | | | | | |
| 2 | 0.28 | 5 | 0.56 | | | | | | | 100 | | 98 | 25 | (70) | 82 | | | | | | |

-continued

| | | | | | | | | | | | | | | | | | | |
|---|---|---|---|---|---|---|---|---|---|---|---|---|---|---|---|---|---|---|
| 2 | 0.56 | 5 | 0.56 | 95 | (0) | 95 | 95 | (0) | 95 | 85 | | 80 | | | | | | |
| 2 | 0.56 | 5 | 0.56 | | | | | | | 80 | (6) | 85 | | | | 70 | (10) | 77 |
| 2 | 1.12 | 5 | 0.56 | | | | | | | 70 | (0) | 70 | 95 | (5) | 100 | | | |
| 2 | 1.12 | 5 | 0.56 | | | | | | | 100 | (0) | 100 | 100 | (0) | 100 | | | |
| 2 | 0.14 | 5 | 2.24 | 15 | (66) | 43 | 60 | (35) | 92 | 30 | (15) | 35 | | | | | | |
| 2 | 0.14 | 5 | 2.24 | | | | | | | 0 | (100) | 60 | | | | 20 | (48) | 38 |
| 2 | 0.28 | 5 | 2.24 | | | | | | | 100 | | 98 | 95 | | 82 | | | |
| 2 | 0.28 | 5 | 2.24 | | | | | | | 85 | | 60 | 95 | | 92 | | | |
| 2 | 0.56 | 5 | 2.24 | 90 | (6) | 95 | 95 | (0) | 95 | 90 | | 80 | | | | | | |
| 2 | 0.56 | 5 | 2.24 | | | | | | | 95 | | 85 | | | | 80 | | 77 |
| 2 | 1.12 | 5 | 2.24 | | | | | | | 100 | (0) | 100 | 100 | (0) | 100 | | | |
| 2 | 1.12 | 5 | 2.24 | | | | | | | 100 | | 70 | 100 | (0) | 100 | | | |
| 2 | 0.14 | 5 | 8.96 | 60 | | 43 | 85 | (8) | 92 | 55 | | 35 | | | | | | |
| 2 | 0.14 | 5 | 8.96 | | | | | | | 55 | (9) | 60 | | | | 80 | | 38 |
| 2 | 0.28 | 5 | 8.96 | | | | | | | 100 | | 98 | 100 | | 82 | | | |
| 2 | 0.28 | 5 | 8.96 | | | | | | | 95 | | 60 | 80 | (14) | 92 | | | |
| 2 | 0.56 | 5 | 8.96 | 80 | (16) | 95 | 95 | (0) | 95 | 90 | | 80 | | | | | | |
| 2 | 0.56 | 5 | 8.96 | | | | | | | 25 | (71) | 85 | | | | 85 | | 77 |
| 2 | 1.12 | 5 | 8.96 | | | | | | | 100 | (0) | 100 | 100 | (0) | 100 | | | |
| 2 | 1.12 | 5 | 8.96 | | | | | | | 95 | | 70 | 100 | (0) | 100 | | | |
| 3 | 2.24 | 5 | 0.56 | | | | | | | 20 | (64) | 55 | 5 | (50) | 10 | | | |
| 3 | 4.48 | 5 | 0.56 | | | | | | | 40 | (28) | 55 | 10 | (75) | 40 | | | |
| 3 | 2.24 | 5 | 2.24 | | | | | | | 50 | (10) | 55 | 15 | | 10 | | | |
| 3 | 4.48 | 5 | 2.24 | | | | | | | 25 | (55) | 55 | 15 | (63) | 40 | | | |
| 3 | 2.24 | 5 | 8.96 | | | | | | | 55 | (0) | 55 | 30 | | 10 | | | |
| 3 | 4.48 | 5 | 8.96 | | | | | | | 90 | | 55 | 10 | (75) | 40 | | | |
| 4 | 0.14 | 5 | 0.56 | 100 | | 98 | 95 | (4) | 98 | 95 | (0) | 95 | | | | | | |
| 4 | 0.56 | 5 | 0.56 | 100 | (0) | 100 | 100 | (0) | 100 | 100 | (0) | 100 | | | | | | |
| 4 | 0.56 | 5 | 0.56 | | | | | | | 80 | (0) | 80 | 60 | (34) | 90 | | | |

-continued

| | | | | | | | | | | | | | | | | | | | | | |
|---|---|---|---|---|---|---|---|---|---|---|---|---|---|---|---|---|---|---|---|---|---|
| 4 | 1.12 | 5 | 0.56 | | | | | | | 95 | | 80 | 95 | (3) | 97 | | | | | | |
| 4 | 1.12 | 5 | 0.56 | | | | | | | 60 | (15) | 70 | | | | 50 | | 7 | | | |
| 4 | 2.24 | 5 | 0.56 | | | | | | | 55 | (25) | 73 | | | | 40 | | 30 | | | |
| 4 | 0.14 | 5 | 2.24 | 100 | | 98 | 100 | | 98 | 100 | | 95 | | | | | | | | | |
| 4 | 0.56 | 5 | 2.24 | 100 | (0) | 100 | 100 | (0) | 100 | 95 | (5) | 100 | | | | | | | | | |
| 4 | 0.56 | 5 | 2.24 | | | | | | | 80 | (0) | 80 | 15 | (84) | 90 | | | | | | |
| 4 | 1.12 | 5 | 2.24 | | | | | | | 85 | | 80 | 90 | (8) | 97 | | | | | | |
| 4 | 1.12 | 5 | 2.24 | | | | | | | 70 | (0) | 70 | | | | 0 | (100) | 7 | | | |
| 4 | 2.24 | 5 | 2.24 | | | | | | | 80 | | 73 | | | | 85 | | 30 | | | |
| 4 | 0.14 | 5 | 8.96 | 95 | (4) | 98 | 90 | (9) | 98 | 100 | | 95 | | | | | | | | | |
| 4 | 0.56 | 5 | 8.96 | 100 | (0) | 100 | 100 | (0) | 100 | 100 | (0) | 100 | | | | | | | | | |
| 4 | 0.56 | 5 | 8.96 | | | | | | | 90 | | 80 | 15 | (84) | 90 | | | | | | |
| 4 | 1.12 | 5 | 8.96 | | | | | | | 95 | | 80 | 30 | (70) | 97 | | | | | | |
| 4 | 1.12 | 5 | 8.96 | | | | | | | 75 | | 70 | | | | 0 | (100) | 7 | | | |
| 4 | 2.24 | 5 | 8.96 | | | | | | | 100 | | 73 | | | | 95 | | 30 | | | |
| 5 | 0.14 | 5 | 0.56 | | | | | | | 70 | (18) | 85 | | | | 20 | (29) | 28 | | | |
| 5 | 0.14 | 5 | 0.56 | | | | | | | 45 | | 35 | 0 | | | | | | | | |
| 5 | 0.14 | 5 | 0.56 | | | | 25 | (22) | 32 | 40 | (34) | 60 | | | | | | | 95 | (5) | 100 |
| 5 | 0.56 | 5 | 0.56 | | | | 95 | (0) | 95 | 80 | (12) | 90 | | | | | | | 100 | (0) | 100 |
| 5 | 0.56 | 5 | 0.56 | | | | | | | 90 | (0) | 90 | | | | 65 | | 50 | | | |
| 5 | 0.56 | 5 | 0.56 | | | | | | | 60 | (25) | 80 | 55 | (27) | 75 | | | | | | |
| 5 | 0.14 | 5 | 2.24 | | | | | | | 90 | | 85 | | | | 80 | | 28 | | | |
| 5 | 0.14 | 5 | 2.24 | | | | | | | 65 | | 35 | 0 | | | | | | | | |
| 5 | 0.14 | 5 | 2.24 | | | | 40 | | 32 | 0 | (100) | 60 | | | | | | | 65 | (35) | 100 |
| 5 | 0.56 | 5 | 2.24 | | | | | | | 90 | (0) | 90 | | | | 35 | (30) | 50 | | | |
| 5 | 0.56 | 5 | 2.24 | | | | | | | 70 | (13) | 80 | 0 | (100) | 75 | | | | | | |
| 5 | 0.56 | 5 | 2.24 | | | | 80 | (16) | 95 | 95 | | 90 | | | | | | | 100 | (0) | 100 |
| 5 | 0.14 | 5 | 8.96 | | | | | | | 65 | (24) | 85 | | | | 55 | | 28 | | | |
| 5 | 0.14 | 5 | 8.96 | | | | 20 | (38) | 32 | 95 | | 60 | | | | | | | 95 | (5) | 100 |
| 5 | 0.14 | 5 | 8.96 | | | | | | | 75 | | 35 | 0 | | | | | | | | |
| 5 | 0.56 | 5 | 8.96 | | | | | | | 95 | | 90 | | | | 65 | | 50 | | | |

-continued

| | | | | | | | | | | | | | | | | | | | | | | | | |
|---|---|---|---|---|---|---|---|---|---|---|---|---|---|---|---|---|---|---|---|---|---|---|---|---|
| 5 | 0.56 | 5 | 8.96 | | | | | | | 70 | (13) | 80 | 0 | (100) | 75 | | | | | | | | | |
| 5 | 0.56 | 5 | 8.96 | | | | 55 | (43) | 95 | 95 | | 90 | | | | | | | | | | 100 | (0) | 100 |
| 1 | 0.03 | 6 | 0.56 | 0 | (100) | 35 | 80 | | 45 | 95 | | 65 | 0 | (100) | 25 | 25 | (0) | 25 | | | | | | |
| 1 | 0.14 | 6 | 0.56 | 15 | (85) | 95 | 90 | (8) | 97 | 95 | | 90 | 90 | | 80 | 45 | (10) | 50 | | | | | | |
| 1 | 0.03 | 6 | 2.24 | 0 | (100) | 35 | 65 | | 45 | 95 | | 65 | 10 | (60) | 25 | 0 | (100) | 25 | | | | | | |
| 1 | 0.14 | 6 | 2.24 | 70 | (27) | 95 | 90 | (8) | 97 | 95 | | 90 | 80 | (0) | 80 | 60 | | 50 | | | | | | |
| 1 | 0.03 | 6 | 8.96 | 0 | (100) | 35 | 0 | (100) | 45 | 95 | | 65 | 5 | (80) | 25 | 40 | | 25 | | | | | | |
| 1 | 0.14 | 6 | 8.96 | 75 | (22) | 95 | 100 | | 97 | 100 | | 90 | 25 | (69) | 80 | 35 | (30) | 50 | | | | | | |
| 2 | 0.14 | 6 | 0.56 | 5 | (89) | 43 | 80 | (14) | 92 | 10 | (72) | 35 | | | | | | | | | | | | |
| 2 | 0.14 | 6 | 0.56 | | | | | | | 0 | (100) | 60 | | | | | | | 30 | (22) | 38 | | | |
| 2 | 0.28 | 6 | 0.56 | | | | | | | 100 | | 98 | 90 | | 82 | | | | | | | | | |
| 2 | 0.28 | 6 | 0.56 | | | | | | | 70 | | 60 | 95 | | 92 | | | | | | | | | |
| 2 | 0.56 | 6 | 0.56 | 95 | (0) | 95 | 95 | (0) | 95 | 90 | | 80 | | | | | | | | | | | | |
| 2 | 0.56 | 6 | 0.56 | | | | | | | 60 | (30) | 85 | | | | | | | 95 | | 77 | | | |
| 2 | 1.12 | 6 | 0.56 | | | | | | | 100 | (0) | 100 | 100 | (0) | 100 | | | | | | | | | |
| 2 | 1.12 | 6 | 0.56 | | | | | | | 85 | | 70 | 100 | (0) | 100 | | | | | | | | | |
| 2 | 0.14 | 6 | 2.24 | 20 | (54) | 43 | 85 | (8) | 92 | 80 | | 35 | | | | | | | | | | | | |
| 2 | 0.14 | 6 | 2.24 | | | | | | | 65 | | 60 | | | | | | | 65 | | 38 | | | |
| 2 | 0.28 | 6 | 2.24 | | | | | | | 100 | | 98 | 75 | (9) | 82 | | | | | | | | | |
| 2 | 0.28 | 6 | 2.24 | | | | | | | 75 | | 60 | 95 | | 92 | | | | | | | | | |
| 2 | 0.56 | 6 | 2.24 | 60 | (37) | 95 | 95 | (0) | 95 | 90 | | 80 | | | | | | | | | | | | |
| 2 | 0.56 | 6 | 2.24 | | | | | | | 95 | | 85 | | | | | | | 90 | | 77 | | | |
| 2 | 1.12 | 6 | 2.24 | | | | | | | 100 | (0) | 100 | 100 | (0) | 100 | | | | | | | | | |
| 2 | 1.12 | 6 | 2.24 | | | | | | | 70 | (0) | 70 | 100 | (0) | 100 | | | | | | | | | |
| 2 | 0.14 | 6 | 8.96 | 40 | (7) | 43 | 65 | (30) | 92 | 70 | | 35 | | | | | | | | | | | | |
| 2 | 0.14 | 6 | 8.96 | | | | | | | 50 | (17) | 60 | | | | | | | 20 | (48) | 38 | | | |
| 2 | 0.28 | 6 | 8.96 | | | | | | | 100 | | 98 | 95 | | 82 | | | | | | | | | |
| 2 | 0.28 | 6 | 8.96 | | | | | | | 85 | | 60 | 100 | | 92 | | | | | | | | | |
| 2 | 0.56 | 6 | 8.96 | 80 | (16) | 95 | 95 | (0) | 95 | 80 | (0) | 80 | | | | | | | | | | | | |
| 2 | 0.56 | 6 | 8.96 | | | | | | | 65 | (24) | 85 | | | | | | | 70 | (10) | 77 | | | |
| 2 | 1.12 | 6 | 8.96 | | | | | | | 100 | | 100 | 100 | | 100 | | | | | | | | | |

-continued

| | | | | | | | | | | | | | | | | | | | | | |
|---|---|---|---|---|---|---|---|---|---|---|---|---|---|---|---|---|---|---|---|---|---|
| 2 | 1.12 | 6 | 8.96 | | | | | | | 90 | (0) | 70 | 100 | (0) (0) | 100 | | | | | | |
| 3 | 2.24 | 6 | 0.56 | | | | | | | 25 | (55) | 55 | 40 | | 10 | | | | | | |
| 3 | 4.48 | 6 | 0.56 | | | | | | | 50 | (10) | 55 | 90 | | 40 | | | | | | |
| 3 | 2.24 | 6 | 2.24 | | | | | | | 20 | (64) | 55 | 35 | | 10 | | | | | | |
| 3 | 4.48 | 6 | 2.24 | | | | | | | 25 | (55) | 55 | 55 | | 40 | | | | | | |
| 3 | 2.24 | 6 | 8.96 | | | | | | | 45 | (19) | 55 | 50 | | 10 | | | | | | |
| 3 | 4.48 | 6 | 8.96 | | | | | | | 30 | (46) | 55 | 80 | | 40 | | | | | | |
| 4 | 0.14 | 6 | 0.56 | 95 | (4) | 98 | 95 | (4) | 98 | 95 | (0) | 95 | | | | | | | | | |
| 4 | 0.56 | 6 | 0.56 | 100 | (0) | 100 | 100 | (0) | 100 | 100 | (0) | 100 | | | | | | | | | |
| 4 | 0.56 | 6 | 0.56 | | | | | | | 30 | (63) | 80 | 25 | (73) | 90 | | | | | | |
| 4 | 1.12 | 6 | 0.56 | | | | | | | 80 | (0) | 80 | 85 | (13) | 97 | | | | | | |
| 4 | 1.12 | 6 | 0.56 | | | | | | | 60 | (15) | 70 | | | | 20 | | 7 | | | |
| 4 | 2.24 | 6 | 0.56 | | | | | | | 75 | | 73 | | | | 25 | (17) | 30 | | | |
| 4 | 0.14 | 6 | 2.24 | 100 | | 98 | 95 | (4) | 98 | 95 | (0) | 95 | | | | | | | | | |
| 4 | 0.56 | 6 | 2.24 | 100 | (0) | 100 | 100 | (0) | 100 | 100 | (0) | 100 | | | | | | | | | |
| 4 | 0.56 | 6 | 2.24 | | | | | | | 85 | | 80 | 75 | (17) | 90 | | | | | | |
| 4 | 1.12 | 6 | 2.24 | | | | | | | 90 | | 80 | 75 | (23) | 97 | | | | | | |
| 4 | 1.12 | 6 | 2.24 | | | | | | | 80 | | 70 | | | | 20 | | 7 | | | |
| 4 | 2.24 | 6 | 2.24 | | | | | | | 85 | | 73 | | | | 5 | (84) | 30 | | | |
| 4 | 0.14 | 6 | 8.96 | 95 | (4) | 98 | 85 | (14) | 98 | 100 | | 95 | | | | | | | | | |
| 4 | 0.56 | 6 | 8.96 | 100 | (0) | 100 | 100 | (0) | 100 | 100 | (0) | 100 | | | | | | | | | |
| 4 | 0.56 | 6 | 8.96 | | | | | | | 100 | | 80 | 5 | (95) | 90 | | | | | | |
| 4 | 1.12 | 6 | 8.96 | | | | | | | 90 | | 80 | 50 | (49) | 97 | | | | | | |
| 4 | 1.12 | 6 | 8.96 | | | | | | | 95 | | 70 | | | | 45 | | 7 | | | |
| 4 | 2.24 | 6 | 8.96 | | | | | | | 80 | | 73 | | | | 20 | (34) | 30 | | | |
| 5 | 0.14 | 6 | 0.56 | | | | | | | 85 | (0) | 85 | | | | 20 | (29) | 28 | | | |
| 5 | 0.14 | 6 | 0.56 | | | | | | | 65 | | 35 | 0 | | | | | | 40 | | 100 |
| 5 | 0.14 | 6 | 0.56 | | | | 65 | | 32 | 60 | (0) | 60 | | | | | | | | (60) | |

-continued

| | | | | | | | | | | | | | | | | | | | | | | | | |
|---|---|---|---|---|---|---|---|---|---|---|---|---|---|---|---|---|---|---|---|---|---|---|---|---|
| 5 | 0.56 | 6 | 0.56 | | | | 80 | (16) | 95 | 95 | | 90 | | | | | | | | | | 100 | (0) | 100 |
| 5 | 0.56 | 6 | 0.56 | | | | | | | 90 | (0) | 90 | | | | | | | 40 | (20) | 50 | | | |
| 5 | 0.56 | 6 | 0.56 | | | | | | | 75 | (7) | 80 | 40 | (47) | 75 | | | | | | | | | |
| 5 | 0.14 | 6 | 2.24 | | | | | | | 100 | | 85 | | | | | | | 20 | (29) | 28 | | | |
| 5 | 0.14 | 6 | 2.24 | | | | | | | 65 | | 35 | 0 | | | | | | | | | | | |
| 5 | 0.14 | 6 | 2.24 | | | | 40 | | 32 | 50 | (17) | 60 | | | | | | | | | | 95 | (5) | 100 |
| 5 | 0.56 | 6 | 2.24 | | | | | | | 90 | (0) | 90 | | | | | | | 45 | (10) | 50 | | | |
| 5 | 0.56 | 6 | 2.24 | | | | 90 | (6) | 95 | 90 | (0) | 90 | | | | | | | | | | 100 | (0) | 100 |
| 5 | 0.56 | 6 | 2.24 | | | | | | | 75 | (7) | 80 | 0 | (100) | 75 | | | | | | | | | |
| 5 | 0.14 | 6 | 8.96 | | | | | | | 90 | | 85 | | | | | | | 45 | | 28 | | | |
| 5 | 0.14 | 6 | 8.96 | | | | | | | 55 | | 35 | 0 | | | | | | | | | | | |
| 5 | 0.14 | 6 | 8.96 | | | | 10 | (69) | 32 | 75 | | 60 | | | | | | | | | | 90 | (10) | 100 |
| 5 | 0.56 | 6 | 8.96 | | | | | | | 100 | | 90 | | | | | | | 50 | (0) | 50 | | | |
| 5 | 0.56 | 6 | 8.96 | | | | | | | 70 | (13) | 80 | 15 | (80) | 75 | | | | | | | | | |
| 5 | 0.56 | 6 | 8.96 | | | | 95 | (0) | 95 | 90 | (0) | 90 | | | | | | | | | | 100 | (0) | 100 |
| 1 | 0.03 | 7 | 0.56 | 0 | (100) | 35 | 95 | | 45 | 90 | | 65 | 15 | (40) | 25 | 30 | | 25 | | | | | | |
| 1 | 0.14 | 7 | 0.56 | 80 | (16) | 95 | 100 | | 97 | 100 | | 90 | 95 | | 80 | 50 | (0) | 50 | | | | | | |
| 1 | 0.03 | 7 | 2.24 | 0 | (100) | 35 | 10 | (78) | 45 | 95 | | 65 | 0 | (100) | 25 | 25 | (0) | 25 | | | | | | |
| 1 | 0.14 | 7 | 2.24 | 35 | (64) | 95 | 80 | (18) | 97 | 95 | | 90 | 60 | (25) | 80 | 45 | (10) | 50 | | | | | | |
| 1 | 0.03 | 7 | 8.96 | 15 | (58) | 35 | 40 | (12) | 45 | 95 | | 65 | 0 | (100) | 25 | 45 | | 25 | | | | | | |
| 1 | 0.14 | 7 | 8.96 | 10 | (90) | 95 | 95 | (3) | 97 | 95 | | 90 | 5 | (94) | 80 | 30 | (40) | 50 | | | | | | |
| 2 | 0.14 | 7 | 0.56 | 35 | (19) | 43 | 90 | (3) | 92 | 0 | (100) | 35 | | | | | | | | | | | | |
| 2 | 0.14 | 7 | 0.56 | | | | | | | 0 | (100) | 60 | | | | | | | 10 | (74) | 38 | | | |
| 2 | 0.28 | 7 | 0.56 | | | | | | | 100 | | 98 | 100 | | 82 | | | | | | | | | |
| 2 | 0.28 | 7 | 0.56 | | | | | | | 80 | | 60 | 90 | (3) | 92 | | | | | | | | | |
| 2 | 0.56 | 7 | 0.56 | 90 | (6) | 95 | 95 | (0) | 95 | 80 | (0) | 80 | | | | | | | | | | | | |
| 2 | 0.56 | 7 | 0.56 | | | | | | | 100 | | 85 | | | | | | | 90 | | 77 | | | |
| 2 | 1.12 | 7 | 0.56 | | | | | | | 100 | (0) | 100 | 100 | (0) | 100 | | | | | | | | | |
| 2 | 1.12 | 7 | 0.56 | | | | | | | 80 | (0) | 70 | 100 | | 100 | | | | | | | | | |
| 2 | 0.14 | 7 | 2.24 | 10 | | 43 | 80 | | 92 | 60 | | 35 | | | | | | | | | | | | |

-continued

| | | | | | | | | | | | | | | | | | | |
|---|---|---|---|---|---|---|---|---|---|---|---|---|---|---|---|---|---|---|
| | | | | | (77) | | | (14) | | | | | | | | | | |
| 2 | 0.14 | 7 | 2.24 | | | | | | | 90 | | 60 | | | | 75 | | 38 |
| 2 | 0.28 | 7 | 2.24 | | | | | | | 100 | | 98 | 100 | | 82 | | | |
| 2 | 0.28 | 7 | 2.24 | | | | | | | 90 | | 60 | 95 | | 92 | | | |
| 2 | 0.56 | 7 | 2.24 | 90 | | 95 | 95 | | 95 | 90 | | 80 | | | | | | |
| | | | | | (6) | | | (0) | | | | | | | | | | |
| 2 | 0.56 | 7 | 2.24 | | | | | | | 100 | | 85 | | | | 95 | | 77 |
| 2 | 1.12 | 7 | 2.24 | | | | | | | 100 | | 100 | 100 | | 100 | | | |
| | | | | | | | | | | | (0) | | | (0) | | | | |
| 2 | 1.12 | 7 | 2.24 | | | | | | | 80 | | 70 | 100 | | 100 | | | |
| | | | | | | | | | | | | | | (0) | | | | |
| 2 | 0.14 | 7 | 8.96 | 0 | | 43 | 80 | | 92 | 95 | | 35 | | | | | | |
| | | | | | (100) | | | (14) | | | | | | | | | | |
| 2 | 0.14 | 7 | 8.96 | | | | | | | 95 | | 60 | | | | 30 | | 38 |
| | | | | | | | | | | | | | | | | | (22) | |
| 2 | 0.28 | 7 | 8.96 | | | | | | | 100 | | 98 | 70 | | 82 | | | |
| | | | | | | | | | | | | | | (15) | | | | |
| 2 | 0.28 | 7 | 8.96 | | | | | | | 100 | | 60 | 90 | | 92 | | | |
| | | | | | | | | | | | | | | (3) | | | | |
| 2 | 0.56 | 7 | 8.96 | 90 | | 95 | 95 | | 95 | 100 | | 80 | | | | | | |
| | | | | | (6) | | | (0) | | | | | | | | | | |
| 2 | 0.56 | 7 | 8.96 | | | | | | | 95 | | 85 | | | | 90 | | 77 |
| 2 | 1.12 | 7 | 8.96 | | | | | | | 100 | | 100 | 100 | | 100 | | | |
| | | | | | | | | | | | (0) | | | (0) | | | | |
| 2 | 1.12 | 7 | 8.96 | | | | | | | 85 | | 70 | 100 | | 100 | | | |
| | | | | | | | | | | | | | | (0) | | | | |
| 3 | 2.24 | 7 | 0.56 | | | | | | | 35 | | 55 | 30 | | 10 | | | |
| | | | | | | | | | | | (37) | | | | | | | |
| 3 | 4.48 | 7 | 0.56 | | | | | | | 25 | | 55 | 40 | | 40 | | | |
| | | | | | | | | | | | (55) | | | (0) | | | | |
| 3 | 2.24 | 7 | 2.24 | | | | | | | 95 | | 55 | 75 | | 10 | | | |
| 3 | 4.48 | 7 | 2.24 | | | | | | | 50 | | 55 | 55 | | 40 | | | |
| | | | | | | | | | | | (10) | | | | | | | |
| 3 | 2.24 | 7 | 8.96 | | | | | | | 85 | | 55 | 30 | | 10 | | | |
| 3 | 4.48 | 7 | 8.96 | | | | | | | 100 | | 55 | 50 | | 40 | | | |
| 3 | 0.14 | 7 | 0.56 | 100 | | 98 | 100 | | 98 | 100 | | 95 | | | | | | |
| 3 | 0.56 | 7 | 0.56 | 100 | | 100 | 100 | | 100 | 95 | | 100 | | | | | | |
| | | | | | (0) | | | (0) | | | (5) | | | | | | | |
| 4 | 0.56 | 7 | 0.56 | | | | | | | 75 | | 80 | 85 | | 90 | | | |
| | | | | | | | | | | | (7) | | | (6) | | | | |
| 4 | 1.12 | 7 | 0.56 | | | | | | | 65 | | 80 | 95 | | 97 | | | |
| | | | | | | | | | | | (19) | | | (3) | | | | |
| 4 | 1.12 | 7 | 0.56 | | | | | | | 65 | | 70 | | | | 10 | | 7 |
| | | | | | | | | | | | (8) | | | | | | | |
| 4 | 2.24 | 7 | 0.56 | | | | | | | 45 | | 73 | | | | 20 | | 30 |
| | | | | | | | | | | | (39) | | | | | | (34) | |

| | | | | | | | | | | | | | | | | | | | | | | | | |
|---|---|---|---|---|---|---|---|---|---|---|---|---|---|---|---|---|---|---|---|---|---|---|---|---|
| 4 | 0.14 | 7 | 2.24 | 95 | (4) | 98 | 90 | (9) | 98 | 100 | | 95 | | | | | | | | | | | | |
| 4 | 0.56 | 7 | 2.24 | 100 | (0) | 100 | 100 | (0) | 100 | 100 | (0) | 100 | | | | | | | | | | | | |
| 4 | 0.56 | 7 | 2.24 | | | | | | | 85 | | 80 | 50 | (45) | 90 | | | | | | | | | |
| 4 | 1.12 | 7 | 2.24 | | | | | | | 65 | (19) | 80 | 70 | (28) | 97 | | | | | | | | | |
| 4 | 1.12 | 7 | 2.24 | | | | | | | 90 | | 70 | | | | | | | 20 | | 7 | | | |
| 4 | 2.24 | 7 | 2.24 | | | | | | | 70 | (5) | 73 | | | | | | | 25 | (17) | 30 | | | |
| 4 | 0.14 | 7 | 8.96 | 100 | | 98 | 70 | (29) | 98 | 100 | | 95 | | | | | | | | | | | | |
| 4 | 0.56 | 7 | 8.96 | 100 | (0) | 100 | 100 | (0) | 100 | 100 | (0) | 100 | | | | | | | | | | | | |
| 4 | 0.56 | 7 | 8.96 | | | | | | | 100 | | 80 | 5 | (95) | 90 | | | | | | | | | |
| 4 | 1.12 | 7 | 8.96 | | | | | | | 100 | | 80 | 85 | (13) | 97 | | | | | | | | | |
| 4 | 1.12 | 7 | 8.96 | | | | | | | 100 | | 70 | | | | | | | 85 | | 7 | | | |
| 4 | 2.24 | 7 | 8.96 | | | | | | | 100 | | 73 | | | | | | | 95 | | 30 | | | |
| 5 | 0.14 | 7 | 0.56 | | | | | | | 85 | (0) | 85 | | | | | | | 60 | | 28 | | | |
| 5 | 0.14 | 7 | 0.56 | | | | | | | 60 | | 35 | 0 | | | | | | | | | | | |
| 5 | 0.14 | 7 | 0.56 | | | | 50 | | 32 | 15 | (75) | 60 | | | | | | | | | | 90 | (10) | 100 |
| 5 | 0.56 | 7 | 0.56 | | | | 70 | (27) | 95 | 90 | (0) | 90 | | | | | | | | | | 100 | (0) | 100 |
| 5 | 0.56 | 7 | 0.56 | | | | | | | 95 | | 90 | | | | | | | 75 | | 50 | | | |
| 5 | 0.56 | 7 | 0.56 | | | | | | | 70 | (13) | 80 | 35 | (54) | 75 | | | | | | | | | |
| 5 | 0.14 | 7 | 2.24 | | | | | | | 90 | | 85 | | | | | | | 60 | | 28 | | | |
| 5 | 0.14 | 7 | 2.24 | | | | | | | 65 | | 35 | 0 | | | | | | | | | | | |
| 5 | 0.14 | 7 | 2.24 | | | | 10 | (69) | 32 | 25 | (59) | 60 | | | | | | | | | | 90 | (10) | 100 |
| 5 | 0.56 | 7 | 2.24 | | | | | | | 95 | | 90 | | | | | | | 50 | (0) | 50 | | | |
| 5 | 0.56 | 7 | 2.24 | | | | 85 | (11) | 95 | 90 | (0) | 90 | | | | | | | | | | 90 | (10) | 100 |
| 5 | 0.56 | 7 | 2.24 | | | | | | | 70 | (13) | 80 | 0 | (100) | 75 | | | | | | | | | |
| 5 | 0.14 | 7 | 8.96 | | | | | | | 90 | | 85 | | | | | | | 90 | | 28 | | | |
| 5 | 0.14 | 7 | 8.96 | | | | | | | 75 | | 35 | 0 | | | | | | | | | | | |
| 5 | 0.14 | 7 | 8.96 | | | | 15 | (54) | 32 | 95 | | 60 | | | | | | | | | | 85 | (15) | 100 |
| 5 | 0.56 | 7 | 8.96 | | | | | | | 95 | | 90 | | | | | | | 90 | | 50 | | | |
| 5 | 0.56 | 7 | 8.96 | | | | | | | 80 | (0) | 80 | 20 | (74) | 75 | | | | | | | | | |
| 5 | 0.56 | 7 | 8.96 | | | | 70 | (27) | 95 | 100 | | 90 | | | | | | | | | | 100 | (0) | 100 |
| 1 | 0.03 | 9 | 0.56 | 10 | (72) | 35 | 70 | | 45 | 85 | | 65 | 15 | (40) | 25 | 5 | (80) | 25 | | | | | | |
| 1 | 0.14 | 9 | 0.56 | 95 | (0) | 95 | 100 | | 97 | 95 | | 90 | 45 | (44) | 80 | 20 | (60) | 50 | | | | | | |

-continued

| | | | | | | | | | | | | | | | | | | | | | |
|---|---|---|---|---|---|---|---|---|---|---|---|---|---|---|---|---|---|---|---|---|---|
| 1 | 0.03 | 9 | 2.24 | 0 | (100) | 35 | 60 | | 45 | 90 | | 65 | 0 | (100) | 25 | 10 | (60) | 25 | | | |
| 1 | 0.14 | 9 | 2.24 | 85 | (11) | 95 | 90 | (8) | 97 | 90 | (0) | 90 | 20 | (75) | 80 | 20 | (60) | 50 | | | |
| 1 | 0.03 | 9 | 8.96 | 10 | (72) | 35 | 0 | (100) | 45 | 85 | | 65 | 0 | (100) | 25 | 5 | (80) | 25 | | | |
| 1 | 0.14 | 9 | 8.96 | 65 | (32) | 95 | 75 | (23) | 97 | 95 | | 90 | 20 | (75) | 80 | 25 | (50) | 50 | | | |
| 2 | 0.14 | 9 | 0.56 | 25 | (42) | 43 | 80 | (14) | 92 | 10 | (72) | 35 | | | | | | | | | |
| 2 | 0.14 | 9 | 0.56 | | | | | | | 0 | (100) | 60 | | | | | | | 75 | | 38 |
| 2 | 0.28 | 9 | 0.56 | | | | | | | 100 | | 98 | 95 | | 82 | | | | | | |
| 2 | 0.28 | 9 | 0.56 | | | | | | | 80 | | 60 | 85 | (8) | 92 | | | | | | |
| 2 | 0.56 | 9 | 0.56 | 95 | (0) | 95 | 95 | (0) | 95 | 90 | | 80 | | | | | | | | | |
| 2 | 0.56 | 9 | 0.56 | | | | | | | 85 | (0) | 85 | | | | | | | 95 | | 77 |
| 2 | 1.12 | 9 | 0.56 | | | | | | | 100 | (0) | 100 | 100 | (0) | 100 | | | | | | |
| 2 | 1.12 | 9 | 0.56 | | | | | | | 70 | (0) | 70 | 100 | (0) | 100 | | | | | | |
| 2 | 0.14 | 9 | 2.24 | 20 | (54) | 43 | 85 | (8) | 92 | 95 | | 35 | | | | | | | | | |
| 2 | 0.14 | 9 | 2.24 | | | | | | | 0 | (100) | 60 | | | | | | | 95 | | 38 |
| 2 | 0.28 | 9 | 2.24 | | | | | | | 100 | | 98 | 90 | | 82 | | | | | | |
| 2 | 0.28 | 9 | 2.24 | | | | | | | 75 | | 60 | 95 | | 92 | | | | | | |
| 2 | 0.56 | 9 | 2.24 | 75 | (22) | 95 | 95 | (0) | 95 | 90 | | 80 | | | | | | | | | |
| 2 | 0.56 | 9 | 2.24 | | | | | | | 70 | (18) | 85 | | | | | | | 95 | | 77 |
| 2 | 1.12 | 9 | 2.24 | | | | | | | 100 | (0) | 100 | 100 | (0) | 100 | | | | | | |
| 2 | 1.12 | 9 | 2.24 | | | | | | | 25 | (65) | 70 | 100 | (0) | 100 | | | | | | |
| 2 | 0.14 | 9 | 8.96 | 40 | (7) | 43 | 85 | (8) | 92 | 10 | (72) | 35 | | | | | | | | | |
| 2 | 0.14 | 9 | 8.96 | | | | | | | 100 | | 60 | | | | | | | 30 | (22) | 38 |
| 2 | 0.28 | 9 | 8.96 | | | | | | | 95 | (4) | 98 | 95 | | 82 | | | | | | |
| 2 | 0.28 | 9 | 8.96 | | | | | | | 75 | | 60 | 85 | (8) | 92 | | | | | | |
| 2 | 0.56 | 9 | 8.96 | 70 | (27) | 95 | 95 | (0) | 95 | 20 | (75) | 80 | | | | | | | | | |
| 2 | 0.56 | 9 | 8.96 | | | | | | | 90 | | 85 | | | | | | | 90 | | 77 |
| 2 | 1.12 | 9 | 8.96 | | | | | | | 100 | (0) | 100 | 100 | (0) | 100 | | | | | | |
| 2 | 1.12 | 9 | 8.96 | | | | | | | 75 | | 70 | 100 | (0) | 100 | | | | | | |
| 3 | 2.24 | 9 | 0.56 | | | | | | | 95 | | 55 | 15 | | 10 | | | | | | |
| 3 | 4.48 | 9 | 0.56 | | | | | | | 30 | | 55 | 15 | | 40 | | | | | | |

-continued

| | | | | | | | | | | | | | | | | | | | | | |
|---|---|---|---|---|---|---|---|---|---|---|---|---|---|---|---|---|---|---|---|---|---|
| | | | | | | | | | | | (46) | | | (63) | | | | | | | |
| 3 | 2.24 | 9 | 2.24 | | | | | | | 70 | | 55 | 5 | | 10 | | | | | | |
| | | | | | | | | | | | | | | (50) | | | | | | | |
| 3 | 4.48 | 9 | 2.24 | | | | | | | 40 | | 55 | 0 | | 40 | | | | | | |
| | | | | | | | | | | | (28) | | | (100) | | | | | | | |
| 3 | 2.24 | 9 | 8.96 | | | | | | | 60 | | 55 | 5 | | 10 | | | | | | |
| | | | | | | | | | | | | | | (50) | | | | | | | |
| 3 | 4.48 | 9 | 8.96 | | | | | | | 65 | | 55 | 10 | | 40 | | | | | | |
| | | | | | | | | | | | | | | (75) | | | | | | | |
| 4 | 0.14 | 9 | 0.56 | 100 | | 98 | 90 | | 98 | 95 | | 95 | | | | | | | | | |
| | | | | | | | | (9) | | | (0) | | | | | | | | | | |
| 4 | 0.56 | 9 | 0.56 | 100 | | 100 | 100 | | 100 | 95 | | 100 | | | | | | | | | |
| | | | | | (0) | | | (0) | | | (5) | | | | | | | | | | |
| 4 | 0.56 | 9 | 0.56 | | | | | | | 65 | | 80 | 50 | | 90 | | | | | | |
| | | | | | | | | | | | (19) | | | (45) | | | | | | | |
| 4 | 1.12 | 9 | 0.56 | | | | | | | 60 | | 80 | 95 | | 97 | | | | | | |
| | | | | | | | | | | | (25) | | | (3) | | | | | | | |
| 4 | 1.12 | 9 | 0.56 | | | | | | | 70 | | 70 | | | | 30 | | 7 | | | |
| | | | | | | | | | | | (0) | | | | | | | | | | |
| 4 | 2.24 | 9 | 0.56 | | | | | | | 75 | | 73 | | | | 45 | | 30 | | | |
| 4 | 0.14 | 9 | 2.24 | 95 | | 98 | 95 | | 98 | 95 | | 95 | | | | | | | | | |
| | | | | | (4) | | | (4) | | | (0) | | | | | | | | | | |
| 4 | 0.56 | 9 | 2.24 | 100 | | 100 | 100 | | 100 | 100 | | 100 | | | | | | | | | |
| | | | | | (0) | | | (0) | | | (0) | | | | | | | | | | |
| 4 | 0.56 | 9 | 2.24 | | | | | | | 65 | | 80 | 30 | | 90 | | | | | | |
| | | | | | | | | | | | (19) | | | (67) | | | | | | | |
| 4 | 1.12 | 9 | 2.24 | | | | | | | 85 | | 80 | 85 | | 97 | | | | | | |
| | | | | | | | | | | | | | | (13) | | | | | | | |
| 4 | 1.12 | 9 | 2.24 | | | | | | | 80 | | 70 | | | | 0 | | 7 | | | |
| | | | | | | | | | | | | | | | | | (100) | | | | |
| 4 | 2.24 | 9 | 2.24 | | | | | | | 70 | | 73 | | | | 55 | | 30 | | | |
| | | | | | | | | | | | (5) | | | | | | | | | | |
| 4 | 0.14 | 9 | 8.96 | 95 | | 98 | 100 | | 98 | 95 | | 95 | | | | | | | | | |
| | | | | | (4) | | | | | | (0) | | | | | | | | | | |
| 4 | 0.56 | 9 | 8.96 | 100 | | 100 | 100 | | 100 | 100 | | 100 | | | | | | | | | |
| | | | | | (0) | | | (0) | | | (0) | | | | | | | | | | |
| 4 | 0.56 | 9 | 8.96 | | | | | | | 85 | | 80 | 65 | | 90 | | | | | | |
| | | | | | | | | | | | | | | (28) | | | | | | | |
| 4 | 1.12 | 9 | 8.96 | | | | | | | 80 | | 80 | 80 | | 97 | | | | | | |
| | | | | | | | | | | | (0) | | | (18) | | | | | | | |
| 4 | 1.12 | 9 | 8.96 | | | | | | | 85 | | 70 | | | | 45 | | 7 | | | |
| 4 | 2.24 | 9 | 8.96 | | | | | | | 60 | | 73 | | | | 50 | | 30 | | | |
| | | | | | | | | | | | (18) | | | | | | | | | | |
| 5 | 0.14 | 9 | 0.56 | | | | | | | 95 | | 85 | | | | 10 | | 28 | | | |
| | | | | | | | | | | | | | | | | | (65) | | | | |
| 5 | 0.14 | 9 | 0.56 | | | | | | | 50 | | 35 | 0 | | | | | | | | |
| 5 | 0.14 | 9 | 0.56 | | | | 40 | | 32 | 10 | | 60 | | | | | | | 35 | | 100 |
| | | | | | | | | | | | (84) | | | | | | | | | (65) | |
| 5 | 0.56 | 9 | 0.56 | | | | 95 | | 95 | 90 | | 90 | | | | | | | 95 | | 100 |
| | | | | | | | | (0) | | | (0) | | | | | | | | | (5) | |
| 5 | 0.56 | 9 | 0.56 | | | | | | | 100 | | 90 | | | | 60 | | 50 | | | |
| 5 | 0.56 | 9 | 0.56 | | | | | | | 65 | | 80 | 15 | | 75 | | | | | | |
| | | | | | | | | | | | (19) | | | (80) | | | | | | | |
| 5 | 0.14 | 9 | 2.24 | | | | | | | 90 | | 85 | | | | 60 | | 28 | | | |

-continued

| | | | | | | | | | | | | | | | | | | | | | | | | |
|---|---|---|---|---|---|---|---|---|---|---|---|---|---|---|---|---|---|---|---|---|---|---|---|---|
| 5 | 0.14 | 9 | 2.24 | | | | | | | 55 | | 35 | 0 | | | | | | | | | | | |
| 5 | 0.14 | 9 | 2.24 | | | | 80 | | 32 | 65 | | 60 | | | | | | | | | | 90 | (10) | 100 |
| 5 | 0.56 | 9 | 2.24 | | | | | | | 90 | (0) | 90 | | | | | | | 45 | (10) | 50 | | | |
| 5 | 0.56 | 9 | 2.24 | | | | | | | 65 | (19) | 80 | 10 | (87) | 75 | | | | | | | | | |
| 5 | 0.56 | 9 | 2.24 | | | | 95 | (0) | 95 | 95 | | 90 | | | | | | | | | | 100 | (0) | 100 |
| 5 | 0.14 | 9 | 8.96 | | | | | | | 70 | (18) | 85 | | | | | | | 60 | | 28 | | | |
| 5 | 0.14 | 9 | 8.96 | | | | 0 | (100) | 32 | 100 | | 60 | | | | | | | | | | 65 | (35) | 100 |
| 5 | 0.14 | 9 | 8.96 | | | | | | | 60 | | 35 | 0 | | | | | | | | | | | |
| 5 | 0.56 | 9 | 8.96 | | | | | | | 85 | (6) | 90 | | | | | | | 60 | | 50 | | | |
| 5 | 0.56 | 9 | 8.96 | | | | | | | 65 | (19) | 80 | 20 | (74) | 75 | | | | | | | | | |
| 5 | 0.56 | 9 | 8.96 | | (27) | | 70 | (12) | 95 | 80 | | 90 | | | | | | | | (0) | | 100 | | 100 |
| 1 | 0.03 | 10 | 0.56 | 0 | (100) | 35 | 75 | | 45 | 90 | | 65 | 10 | (60) | 25 | 15 | (40) | 25 | | | | | | |
| 1 | 0.14 | 10 | 0.56 | 95 | (0) | 95 | 50 | (49) | 97 | 95 | | 90 | 45 | (44) | 80 | 20 | (60) | 50 | | | | | | |
| 1 | 0.03 | 10 | 2.24 | 20 | (43) | 35 | 0 | (100) | 45 | 95 | | 65 | 5 | (80) | 25 | 25 | (0) | 25 | | | | | | |
| 1 | 0.14 | 10 | 2.24 | 95 | (0) | 95 | 95 | (3) | 97 | 95 | | 90 | 70 | (13) | 80 | 50 | (0) | 50 | | | | | | |
| 1 | 0.03 | 10 | 8.96 | 10 | (72) | 35 | 0 | (100) | 45 | 95 | | 65 | 5 | (80) | 25 | 35 | | 25 | | | | | | |
| 1 | 0.14 | 10 | 8.96 | 55 | (43) | 95 | 15 | (85) | 97 | 95 | | 90 | 50 | (38) | 80 | 45 | (10) | 50 | | | | | | |
| 2 | 0.14 | 10 | 0.56 | 10 | (77) | 43 | 80 | (14) | 92 | 0 | (100) | 35 | | | | | | | | | | | | |
| 2 | 0.14 | 10 | 0.56 | | | | | | | 45 | (25) | 60 | | | | | | | 30 | (22) | 38 | | | |
| 2 | 0.28 | 10 | 0.56 | | | | | | | 100 | | 98 | 100 | | 82 | | | | | | | | | |
| 2 | 0.28 | 10 | 0.56 | | | | | | | 70 | | 60 | 80 | (14) | 92 | | | | | | | | | |
| 2 | 0.56 | 10 | 0.56 | 85 | (11) | 95 | 95 | (0) | 95 | 85 | | 80 | | | | | | | | | | | | |
| 2 | 0.56 | 10 | 0.56 | | | | | | | 90 | | 85 | | | | | | | 95 | | 77 | | | |
| 2 | 1.12 | 10 | 0.56 | | | | | | | 100 | (0) | 100 | 100 | (0) | 100 | | | | | | | | | |
| 2 | 1.12 | 10 | 0.56 | | | | | | | 65 | (8) | 70 | 100 | (0) | 100 | | | | | | | | | |
| 2 | 0.14 | 10 | 2.24 | 65 | | 43 | 90 | (3) | 92 | 35 | (0) | 35 | | | | | | | | | | | | |
| 2 | 0.14 | 10 | 2.24 | | | | | | | 0 | (100) | 60 | | | | | | | 75 | | 38 | | | |
| 2 | 0.28 | 10 | 2.24 | | | | | | | 95 | (4) | 98 | 100 | | 82 | | | | | | | | | |
| 2 | 0.28 | 10 | 2.24 | | | | | | | 65 | | 60 | 85 | (8) | 92 | | | | | | | | | |

-continued

| | | | | | | | | | | | | | | | | | | |
|---|---|---|---|---|---|---|---|---|---|---|---|---|---|---|---|---|---|---|
| 2 | 0.56 | 10 | 2.24 | 95 | (0) | 95 | 95 | (0) | 95 | 75 | (7) | 80 | | | | | | |
| 2 | 0.56 | 10 | 2.24 | | | | | | | 45 | (48) | 85 | | | | 85 | | 77 |
| 2 | 1.12 | 10 | 2.24 | | | | | | | 100 | (0) | 100 | 100 | (0) | 100 | | | |
| 2 | 1.12 | 10 | 2.24 | | | | | | | 75 | | 70 | 100 | (0) | 100 | | | |
| 2 | 0.14 | 10 | 8.96 | 35 | (19) | 43 | 55 | (41) | 92 | 25 | (29) | 35 | | | | | | |
| 2 | 0.14 | 10 | 8.96 | | | | | | | 0 | (100) | 60 | | | | 20 | (48) | 38 |
| 2 | 0.28 | 10 | 8.96 | | | | | | | 95 | (4) | 98 | 100 | | 82 | | | |
| 2 | 0.28 | 10 | 8.96 | | | | | | | 80 | | 60 | 90 | (3) | 92 | | | |
| 2 | 0.56 | 10 | 8.96 | 85 | (11) | 95 | 95 | (0) | 95 | 65 | (19) | 80 | | | | | | |
| 2 | 0.56 | 10 | 8.96 | | | | | | | 90 | | 85 | | | | 90 | | 77 |
| 2 | 1.12 | 10 | 8.96 | | | | | | | 95 | (5) | 100 | 100 | (0) | 100 | | | |
| 2 | 1.12 | 10 | 8.96 | | | | | | | 85 | | 70 | 95 | (5) | 100 | | | |
| 3 | 2.24 | 10 | 0.56 | | | | | | | 0 | (100) | 55 | 10 | (0) | 10 | | | |
| 3 | 4.48 | 10 | 0.56 | | | | | | | 0 | (100) | 55 | 0 | (100) | 40 | | | |
| 3 | 2.24 | 10 | 2.24 | | | | | | | 0 | (100) | 55 | 5 | (50) | 10 | | | |
| 3 | 4.48 | 10 | 2.24 | | | | | | | 15 | (73) | 55 | 0 | (100) | 40 | | | |
| 3 | 2.24 | 10 | 8.96 | | | | | | | 10 | (82) | 55 | 0 | (100) | 10 | | | |
| 3 | 4.48 | 10 | 8.96 | | | | | | | 50 | (10) | 55 | 10 | (75) | 40 | | | |
| 4 | 0.14 | 10 | 0.56 | 95 | (4) | 98 | 70 | (29) | 98 | 95 | (0) | 95 | | | | | | |
| 4 | 0.56 | 10 | 0.56 | 100 | (0) | 100 | 95 | (5) | 100 | 100 | (0) | 100 | | | | | | |
| 4 | 0.56 | 10 | 0.56 | | | | | | | 70 | (13) | 80 | 85 | (6) | 90 | | | |
| 4 | 1.12 | 10 | 0.56 | | | | | | | 85 | | 80 | 95 | (3) | 97 | | | |
| 4 | 1.12 | 10 | 0.56 | | | | | | | 70 | (0) | 70 | | | | 15 | | 7 |
| 4 | 2.24 | 10 | 0.56 | | | | | | | 55 | (25) | 73 | | | | 5 | (84) | 30 |
| 4 | 0.56 | 10 | 2.24 | 95 | (4) | 98 | 25 | (75) | 98 | 100 | | 95 | | | | | | |
| 4 | 0.56 | 10 | 2.24 | 100 | (0) | 100 | 95 | (5) | 100 | 95 | (5) | 100 | | | | | | |
| 4 | 0.56 | 10 | 2.24 | | | | | | | 70 | (13) | 80 | 55 | (39) | 90 | | | |
| 4 | 1.12 | 10 | 2.24 | | | | | | | 70 | | 80 | 80 | | 97 | | | |

-continued

| | | | | | | | | | | | | | | | | | | | | | | | | |
|---|---|---|---|---|---|---|---|---|---|---|---|---|---|---|---|---|---|---|---|---|---|---|---|---|
| | | | | | | | | | | | (13) | | | (18) | | | | | | | | | | |
| 4 | 1.12 | 10 | 2.24 | | | | | | | 55 | (22) | 70 | | | | | | | 0 | (100) | 7 | | | |
| 4 | 2.24 | 10 | 2.24 | | | | | | | 65 | (11) | 73 | | | | | | | 20 | (34) | 30 | | | |
| 4 | 0.14 | 10 | 8.96 | 100 | | 98 | 35 | (65) | 98 | 95 | (0) | 95 | | | | | | | | | | | | |
| 4 | 0.56 | 10 | 8.96 | 100 | (0) | 100 | 85 | (15) | 100 | 95 | (5) | 100 | | | | | | | | | | | | |
| 4 | 0.56 | 10 | 8.96 | | | | | (32) | | 55 | (34) | 80 | 60 | | 90 | | | | | | | | | |
| 4 | 1.12 | 10 | 8.96 | | | | | | | 60 | (25) | 80 | 85 | (13) | 97 | | | | | | | | | |
| 4 | 1.12 | 10 | 8.96 | | | | | | | 65 | (8) | 70 | | | | | | | 5 | (29) | 7 | | | |
| 4 | 2.24 | 10 | 8.96 | | | | | | | 75 | | 73 | | | | | | | 50 | | 30 | | | |
| 5 | 0.14 | 10 | 0.56 | | | | | | | 90 | | 85 | | | | | | | 20 | (29) | 28 | | | |
| 5 | 0.14 | 10 | 0.56 | | | | | | | 70 | | 35 | 0 | | | | | | | | | | | |
| 5 | 0.14 | 10 | 0.56 | | | | 35 | | 32 | 40 | (34) | 60 | | | | | | | | | | 55 | (45) | 100 |
| 5 | 0.56 | 10 | 0.56 | | | | 70 | (27) | 95 | 80 | (12) | 90 | | | | | | | | | | 100 | (0) | 100 |
| 5 | 0.56 | 10 | 0.56 | | | | | | | 90 | (0) | 90 | | | | | | | 25 | (50) | 50 | | | |
| 5 | 0.56 | 10 | 0.56 | | | | | | | 70 | (13) | 80 | 30 | (60) | 75 | | | | | | | | | |
| 5 | 0.14 | 10 | 2.24 | | | | | | | 65 | | 35 | 0 | | | | | | | | | | | |
| 5 | 0.14 | 10 | 2.24 | | | | | | | 65 | (24) | 85 | | | | | | | 60 | | 28 | | | |
| 5 | 0.14 | 10 | 2.24 | | | | 25 | (22) | 32 | 30 | (50) | 60 | | | | | | | | | | 45 | (55) | 100 |
| 5 | 0.56 | 10 | 2.24 | | | | 85 | (11) | 95 | 85 | (6) | 90 | | | | | | | | | | 100 | (0) | 100 |
| 5 | 0.56 | 10 | 2.24 | | | | | | | 65 | (19) | 80 | 25 | (67) | 75 | | | | | | | | | |
| 5 | 0.56 | 10 | 2.24 | | | | | | | 95 | | 90 | | | | | | | 25 | (50) | 50 | | | |
| 5 | 0.14 | 10 | 8.96 | | | | | | | 75 | (12) | 85 | | | | | | | 20 | (29) | 28 | | | |
| 5 | 0.14 | 10 | 8.96 | | | | | | | 60 | | 35 | 0 | | | | | | | | | | | |
| 5 | 0.14 | 10 | 8.96 | | | | 0 | (100) | 32 | 70 | | 60 | | | | | | | | | | 95 | (5) | 100 |
| 5 | 0.56 | 10 | 8.96 | | | | | | | 95 | | 90 | | | | | | | 75 | | 50 | | | |
| 5 | 0.56 | 10 | 8.96 | | | | 65 | (32) | 95 | 90 | (0) | 90 | | | | | | | | | | 90 | (10) | 100 |
| 5 | 0.56 | 10 | 8.96 | | | | | | | 65 | (19) | 80 | 20 | (74) | 75 | | | | | | | | | |
| 1 | 0.03 | 11 | 0.56 | 0 | (100) | 35 | 10 | (78) | 45 | 80 | | 65 | 0 | (100) | 25 | 5 | (80) | 25 | | | | | | |
| 1 | 0.14 | 11 | 0.56 | 85 | (11) | 95 | 95 | (3) | 97 | 95 | | 90 | 75 | (7) | 80 | 15 | (70) | 50 | | | | | | |
| 1 | 0.03 | 11 | 2.24 | 30 | (15) | 35 | 55 | | 45 | 95 | | 65 | 10 | (60) | 25 | 20 | (20) | 25 | | | | | | |

-continued

| | | | | | | | | | | | | | | | | | | | | |
|---|---|---|---|---|---|---|---|---|---|---|---|---|---|---|---|---|---|---|---|---|
| 1 | 0.14 | 11 | 2.24 | 85 | (11) | 95 | 35 | (64) | 97 | 95 | | 90 | 80 | (0) | 80 | 100 | | 50 | | |
| 1 | 0.03 | 11 | 8.96 | 15 | (58) | 35 | 0 | (100) | 45 | 100 | | 65 | 15 | (40) | 25 | 10 | (60) | 25 | | |
| 1 | 0.14 | 11 | 8.96 | 25 | (74) | 95 | 10 | (90) | 97 | 100 | | 90 | 75 | (7) | 80 | 20 | (60) | 50 | | |
| 2 | 0.14 | 11 | 0.56 | 35 | (19) | 43 | 60 | (35) | 92 | 0 | (100) | 35 | | | | | | | | |
| 2 | 0.14 | 11 | 0.56 | | | | | | | 90 | | 60 | | | | | | | 55 | 38 |
| 2 | 0.28 | 11 | 0.56 | | | | | | | 100 | | 98 | 100 | | 82 | | | | | |
| 2 | 0.28 | 11 | 0.56 | | | | | | | 65 | | 60 | 80 | (14) | 92 | | | | | |
| 2 | 0.56 | 11 | 0.56 | 60 | (37) | 95 | 95 | (0) | 95 | 10 | (88) | 80 | | | | | | | | |
| 2 | 0.56 | 11 | 0.56 | | | | | | | 95 | | 85 | | | | | | | 95 | 77 |
| 2 | 1.12 | 11 | 0.56 | | | | | | | 100 | (0) | 100 | 100 | (0) | 100 | | | | | |
| 2 | 1.12 | 11 | 0.56 | | | | | | | 80 | | 70 | 100 | (0) | 100 | | | | | |
| 2 | 0.14 | 11 | 2.24 | 45 | | 43 | 65 | (30) | 92 | 0 | (100) | 35 | | | | | | | | |
| 2 | 0.14 | 11 | 2.24 | | | | | | | 85 | | 60 | | | | | | | 75 | 38 |
| 2 | 0.28 | 11 | 2.24 | | | | | | | 95 | (4) | 98 | 95 | | 82 | | | | | |
| 2 | 0.28 | 11 | 2.24 | | | | | | | 75 | | 60 | 85 | (8) | 92 | | | | | |
| 2 | 0.56 | 11 | 2.24 | 90 | (6) | 95 | 95 | (0) | 95 | 80 | (0) | 80 | | | | | | | | |
| 2 | 0.56 | 11 | 2.24 | | | | | | | 95 | | 85 | | | | | | | 95 | 77 |
| 2 | 1.12 | 11 | 2.24 | | | | | | | 95 | (5) | 100 | 100 | (0) | 100 | | | | | |
| 2 | 1.12 | 11 | 2.24 | | | | | | | 85 | | 70 | 95 | (5) | 100 | | | | | |
| 2 | 0.14 | 11 | 8.96 | 35 | (19) | 43 | 30 | (68) | 92 | 10 | (72) | 35 | | | | | | | | |
| 2 | 0.14 | 11 | 8.96 | | | | | | | 90 | | 60 | | | | | | | 70 | 38 |
| 2 | 0.28 | 11 | 8.96 | | | | | | | 95 | (4) | 98 | 95 | | 82 | | | | | |
| 2 | 0.28 | 11 | 8.96 | | | | | | | 80 | | 60 | 80 | (14) | 92 | | | | | |
| 2 | 0.56 | 11 | 8.96 | | | | | | | 90 | | 85 | | | | | | | 85 | 77 |
| 2 | 0.56 | 11 | 8.96 | 85 | (11) | 95 | 95 | (0) | 95 | 20 | (75) | 80 | | | | | | | | |
| 2 | 1.12 | 11 | 8.96 | | | | | | | 100 | (0) | 100 | 100 | (0) | 100 | | | | | |
| 2 | 1.12 | 11 | 8.96 | | | | | | | 90 | | 70 | 100 | (0) | 100 | | | | | |
| 3 | 2.24 | 11 | 0.56 | | | | | | | 50 | (10) | 55 | 45 | | 10 | | | | | |
| 3 | 4.48 | 11 | 0.56 | | | | | | | 50 | (10) | 55 | 50 | | 40 | | | | | |
| 3 | 2.24 | 11 | 2.24 | | | | | | | 15 | (73) | 55 | 55 | | 10 | | | | | |
| 3 | 4.48 | 11 | 2.24 | | | | | | | 90 | | 55 | 80 | | 40 | | | | | |

-continued

| | | | | | | | | | | | | | | | | | | | | | |
|---|---|---|---|---|---|---|---|---|---|---|---|---|---|---|---|---|---|---|---|---|---|
| 3 | 2.24 | 11 | 8.96 | | | | | | | 85 | | 55 | 50 | | 10 | | | | | | |
| 3 | 4.48 | 11 | 8.96 | | | | | | | 50 | (10) | 55 | 45 | | 40 | | | | | | |
| 4 | 0.14 | 11 | 0.56 | 95 | (4) | 98 | 95 | (4) | 98 | 95 | (0) | 95 | | | | | | | | | |
| 4 | 0.56 | 11 | 0.56 | 100 | (0) | 100 | 95 | (5) | 100 | 100 | (0) | 100 | | | | | | | | | |
| 4 | 0.56 | 11 | 0.56 | | | | | | | 90 | | 80 | 90 | (0) | 90 | | | | | | |
| 4 | 1.12 | 11 | 0.56 | | | | | | | 90 | | 80 | 95 | (3) | 97 | | | | | | |
| 4 | 1.12 | 11 | 0.56 | | | | | | | 70 | (0) | 70 | | | | 0 | (100) | 7 | | | |
| 4 | 2.24 | 11 | 0.56 | | | | | | | 70 | (5) | 73 | | | | 0 | (100) | 30 | | | |
| 4 | 0.14 | 11 | 2.24 | 95 | (4) | 98 | 95 | (4) | 98 | 95 | (0) | 95 | | | | | | | | | |
| 4 | 0.56 | 11 | 2.24 | 100 | (0) | 100 | 100 | (0) | 100 | 100 | (0) | 100 | | | | | | | | | |
| 4 | 0.56 | 11 | 2.24 | | | | | | | 60 | (25) | 80 | 55 | (39) | 90 | | | | | | |
| 4 | 1.12 | 11 | 2.24 | | | | | | | 85 | | 80 | 95 | (3) | 97 | | | | | | |
| 4 | 1.12 | 11 | 2.24 | | | | | | | 70 | (0) | 70 | | | | 10 | | 7 | | | |
| 4 | 2.24 | 11 | 2.24 | | | | | | | 70 | (5) | 73 | | | | 55 | | 30 | | | |
| 4 | 0.14 | 11 | 8.96 | 95 | (4) | 98 | 25 | (75) | 98 | 95 | (0) | 95 | | | | | | | | | |
| 4 | 0.56 | 11 | 8.96 | 100 | (0) | 100 | 100 | (0) | 100 | 100 | (0) | 100 | | | | | | | | | |
| 4 | 0.56 | 11 | 8.96 | | | | | | | 85 | | 80 | 70 | (23) | 90 | | | | | | |
| 4 | 1.12 | 11 | 8.96 | | | | | | | 100 | | 80 | 95 | (3) | 97 | | | | | | |
| 4 | 1.12 | 11 | 8.96 | | | | | | | 75 | | 70 | | | | 25 | | 7 | | | |
| 4 | 2.24 | 11 | 8.96 | | | | | | | 75 | | 73 | | | | 50 | | 30 | | | |
| 5 | 0.14 | 11 | 0.56 | | | | | | | 70 | (18) | 85 | | | | 40 | | 28 | | | |
| 5 | 0.14 | 11 | 0.56 | | | | | | | 60 | | 35 | 0 | | | | | | 85 | (15) | 100 |
| 5 | 0.14 | 11 | 0.56 | | | | 60 | | 32 | 50 | (17) | 60 | | | | | | | | | |
| 5 | 0.56 | 11 | 0.56 | | | | | | | 90 | (0) | 90 | | | | 50 | (0) | 50 | | | |
| 5 | 0.56 | 11 | 0.56 | | | | | | | 65 | (19) | 80 | 40 | (47) | 75 | | | | | | |
| 5 | 0.56 | 11 | 0.56 | | | | 80 | (16) | 95 | 85 | (6) | 90 | | | | | | | 100 | (0) | 100 |
| 5 | 0.14 | 11 | 2.24 | | | | 35 | | 32 | 70 | | 60 | | | | | | | 95 | (5) | 100 |
| 5 | 0.14 | 11 | 2.24 | | | | | | | 50 | | 35 | 0 | | | 0 | (100) | 28 | | | |
| 5 | 0.14 | 11 | 2.24 | | | | | | | 60 | (30) | 85 | | | | | | | | | |
| 5 | 0.56 | 11 | 2.24 | | | | | | | 80 | | 90 | | | | 50 | | 50 | | | |

-continued

| | | | | | | | | | | | | | | | | | | | | | | | | |
|---|---|---|---|---|---|---|---|---|---|---|---|---|---|---|---|---|---|---|---|---|---|---|---|---|
| | | | | | | | | | | | (12) | | | | | | | | | (0) | | | | |
| 5 | 0.56 | 11 | 2.24 | | | | 90 | (6) | 95 | 75 | (17) | 90 | | | | | | | | | | 100 | (0) | 100 |
| 5 | 0.56 | 11 | 2.24 | | | | | | | 65 | (19) | 80 | 45 | (40) | 75 | | | | | | | | | |
| 5 | 0.14 | 11 | 8.96 | | | | | | | 80 | (6) | 85 | | | | | | | 20 | (29) | 28 | | | |
| 5 | 0.14 | 11 | 8.96 | | | | 20 (38) | | 32 | 70 | | 60 | | | | | | | | | | 60 (40) | | 100 |
| 5 | 0.14 | 11 | 8.96 | | | | | | | 65 | | 35 | 0 | | | | | | | | | | | |
| 5 | 0.56 | 11 | 8.96 | | | | | | | 95 | | 90 | | | | | | | 60 | | 50 | | | |
| 5 | 0.56 | 11 | 8.96 | | | | | | | 80 | (0) | 80 | 15 | (80) | 75 | | | | | | | | | |
| 5 | 0.56 | 11 | 8.96 | | | | 70 | (27) | 95 | 80 | (12) | 90 | | | | | | | | | | 100 | (0) | 100 |
| 1 | 0.03 | 12 | 0.56 | 5 | (86) | 35 | 60 | | 45 | 90 | | 65 | 5 | (80) | 25 | 15 | (40) | 25 | | | | | | |
| 1 | 0.14 | 12 | 0.56 | 95 | (0) | 95 | 100 | | 97 | 100 | | 90 | 80 | (0) | 80 | 40 | (20) | 50 | | | | | | |
| 1 | 0.03 | 12 | 2.24 | 10 | (72) | 35 | 15 | (67) | 45 | 95 | | 65 | 10 | (60) | 25 | 10 | (60) | 25 | | | | | | |
| 1 | 0.14 | 12 | 2.24 | 50 | (48) | 95 | 90 | (8) | 97 | 90 | (0) | 90 | 85 | | 80 | 50 | (0) | 50 | | | | | | |
| 1 | 0.03 | 12 | 8.96 | 0 | (100) | 35 | 0 | (100) | 45 | 95 | | 65 | 25 | (0) | 25 | 20 | (20) | 25 | | | | | | |
| 1 | 0.14 | 12 | 8.96 | 20 | (79) | 95 | 40 | (59) | 97 | 100 | | 90 | 65 | (19) | 80 | 50 | (0) | 50 | | | | | | |
| 2 | 0.14 | 12 | 0.56 | 20 | (54) | 43 | 25 | (73) | 92 | 15 | (58) | 35 | | | | | | | | | | | | |
| 2 | 0.14 | 12 | 0.56 | | | | | | | 75 | | 60 | | | | | | | 60 | | 38 | | | |
| 2 | 0.28 | 12 | 0.56 | | | | | | | 95 | (4) | 98 | 100 | | 82 | | | | | | | | | |
| 2 | 0.28 | 12 | 0.56 | | | | | | | 45 | (25) | 60 | 50 | (46) | 92 | | | | | | | | | |
| 2 | 0.56 | 12 | 0.56 | 90 | (6) | 95 | 95 | (0) | 95 | 75 | (7) | 80 | | | | | | | | | | | | |
| 2 | 0.56 | 12 | 0.56 | | | | | | | 75 | (12) | 85 | | | | | | | 90 | | 77 | | | |
| 2 | 1.12 | 12 | 0.56 | | | | | | | 100 | (0) | 100 | 100 | (0) | 100 | | | | | | | | | |
| 2 | 1.12 | 12 | 0.56 | | | | | | | 80 | | 70 | 95 | (5) | 100 | | | | | | | | | |
| 2 | 0.14 | 12 | 2.24 | 40 | (7) | 43 | 50 | (46) | 92 | 25 | (29) | 35 | | | | | | | | | | | | |
| 2 | 0.14 | 12 | 2.24 | | | | | | | 80 | | 60 | | | | | | | 60 | | 38 | | | |
| 2 | 0.28 | 12 | 2.24 | | | | | | | 95 | (4) | 98 | 95 | | 82 | | | | | | | | | |
| 2 | 0.28 | 12 | 2.24 | | | | | | | 85 | | 60 | 95 | | 92 | | | | | | | | | |
| 2 | 0.56 | 12 | 2.24 | 85 | (11) | 95 | 95 | (0) | 95 | 85 | | 80 | | | | | | | | | | | | |
| 2 | 0.56 | 12 | 2.24 | | | | | | | 95 | | 85 | | | | | | | 60 | (23) | 77 | | | |
| 2 | 1.12 | 12 | 2.24 | | | | | | | 95 | (5) | 100 | 100 | (0) | 100 | | | | | | | | | |

-continued

| | | | | | | | | | | | | | | | | | | |
|---|---|---|---|---|---|---|---|---|---|---|---|---|---|---|---|---|---|---|
| 2 | 1.12 | 12 | 2.24 | | | | | | | 100 | | 70 | 100 | (0) | 100 | | | |
| 2 | 0.14 | 12 | 8.96 | | | | | | | 95 | | 60 | | | | 10 | (74) | 38 |
| 2 | 0.14 | 12 | 8.96 | 30 | (31) | 43 | 25 | (73) | 92 | 20 | (43) | 35 | | | | | | |
| 2 | 0.28 | 12 | 8.96 | | | | | | | 100 | | 98 | 95 | | 82 | | | |
| 2 | 0.28 | 12 | 8.96 | | | | | | | 90 | | 60 | 85 | (8) | 92 | | | |
| 2 | 0.56 | 12 | 8.96 | 60 | (37) | 95 | 95 | (0) | 95 | 85 | | 80 | | | | | | |
| 2 | 0.56 | 12 | 8.96 | | | | | | | 95 | | 85 | | | | 60 | (23) | 77 |
| 2 | 1.12 | 12 | 8.96 | | | | | | | 100 | (0) | 100 | 100 | (0) | 100 | | | |
| 2 | 1.12 | 12 | 8.96 | | | | | | | 75 | | 70 | 100 | (0) | 100 | | | |
| 3 | 2.24 | 12 | 0.56 | | | | | | | 0 | (100) | 55 | 10 | (0) | 10 | | | |
| 3 | 4.48 | 12 | 0.56 | | | | | | | 25 | (55) | 55 | 30 | (25) | 40 | | | |
| 3 | 2.24 | 12 | 2.24 | | | | | | | 20 | (64) | 55 | 5 | (50) | 10 | | | |
| 3 | 4.48 | 12 | 2.24 | | | | | | | 80 | | 55 | 15 | (63) | 40 | | | |
| 3 | 2.24 | 12 | 8.96 | | | | | | | 95 | | 55 | 10 | (0) | 10 | | | |
| 3 | 4.48 | 12 | 8.96 | | | | | | | 85 | | 55 | 60 | | 40 | | | |
| 4 | 0.14 | 12 | 0.56 | 100 | | 98 | 85 | (14) | 98 | 100 | | 95 | | | | | | |
| 4 | 0.56 | 12 | 0.56 | 100 | (0) | 100 | 95 | (5) | 100 | 100 | (0) | 100 | | | | | | |
| 4 | 0.56 | 12 | 0.56 | | | | | | | 70 | (13) | 80 | 90 | (0) | 90 | | | |
| 4 | 1.12 | 12 | 0.56 | | | | | | | 85 | | 80 | 85 | (13) | 97 | | | |
| 4 | 1.12 | 12 | 0.56 | | | | | | | 55 | (22) | 70 | | | | 25 | | 7 |
| 4 | 2.24 | 12 | 0.56 | | | | | | | 100 | | 73 | | | | 30 | (0) | 30 |
| 4 | 0.14 | 12 | 2.24 | 95 | (4) | 98 | 95 | (4) | 98 | 95 | (0) | 95 | | | | | | |
| 4 | 0.56 | 12 | 2.24 | 100 | (0) | 100 | 95 | (5) | 100 | 95 | (5) | 100 | | | | | | |
| 4 | 0.56 | 12 | 2.24 | | | | | | | 80 | (0) | 80 | 25 | (73) | 90 | | | |
| 4 | 1.12 | 12 | 2.24 | | | | | | | 70 | (13) | 80 | 95 | (3) | 97 | | | |
| 4 | 1.12 | 12 | 2.24 | | | | | | | 85 | | 70 | | | | 30 | | 7 |
| 4 | 2.24 | 12 | 2.24 | | | | | | | 65 | (11) | 73 | | | | 15 | (50) | 30 |
| 4 | 0.14 | 12 | 8.96 | 100 | | 98 | 45 | (55) | 98 | 100 | | 95 | | | | | | |
| 4 | 0.56 | 12 | 8.96 | 95 | | 100 | 100 | | 100 | 100 | | 100 | | | | | | |

-continued

| | | | | | | | | | | | | | | | | | | | | | | | | |
|---|---|---|---|---|---|---|---|---|---|---|---|---|---|---|---|---|---|---|---|---|---|---|---|---|
| | | | | | (5) | | | (0) | | | (0) | | | | | | | | | | | | | |
| 4 | 0.56 | 12 | 8.96 | | | | | | | 95 | | 80 | 5 | | 90 | | | | | | | | | |
| | | | | | | | | | | | | | | (95) | | | | | | | | | | |
| 4 | 1.12 | 12 | 8.96 | | | | | | | 95 | | 80 | 95 | | 97 | | | | | | | | | |
| | | | | | | | | | | | | | | (3) | | | | | | | | | | |
| 4 | 1.12 | 12 | 8.96 | | | | | | | 95 | | 70 | | | | 0 | | 7 | | | | | | |
| | | | | | | | | | | | | | | | | | (100) | | | | | | | |
| 4 | 2.24 | 12 | 8.96 | | | | | | | 85 | | 73 | | | | 65 | | 30 | | | | | | |
| 5 | 0.14 | 12 | 0.56 | | | | | | | 0 | | 85 | | | | 40 | | 28 | | | | | | |
| | | | | | | | | | | | (100) | | | | | | | | | | | | | |
| 5 | 0.14 | 12 | 0.56 | | | | | | | 50 | | 35 | 0 | | | | | | | | | | | |
| 5 | 0.14 | 12 | 0.56 | | | | 40 | | 32 | 40 | | 60 | | | | | | | 95 | | 100 | | | |
| | | | | | | | | | | | (34) | | | | | | | | | (5) | | | | |
| 5 | 0.56 | 12 | 0.56 | | | | | | | 95 | | 90 | | | | 65 | | 50 | | | | | | |
| 5 | 0.56 | 12 | 0.56 | | | | 75 | | 95 | 80 | | 90 | | | | | | | 100 | | 100 | | | |
| | | | | | | | | (22) | | | (12) | | | | | | | | | (0) | | | | |
| 5 | 0.56 | 12 | 0.56 | | | | | | | 70 | | 80 | 45 | | 75 | | | | | | | | | |
| | | | | | | | | | | | (13) | | | (40) | | | | | | | | | | |
| 5 | 0.14 | 12 | 2.24 | | | | | | | 45 | | 35 | 0 | | | | | | | | | | | |
| 5 | 0.14 | 12 | 2.24 | | | | | | | 70 | | 85 | | | | 60 | | 28 | | | | | | |
| | | | | | | | | | | | (18) | | | | | | | | | | | | | |
| 5 | 0.14 | 12 | 2.24 | | | | 5 | | 32 | 60 | | 60 | | | | | | | 95 | | 100 | | | |
| | | | | | | | | (85) | | | (0) | | | | | | | | | (5) | | | | |
| 5 | 0.56 | 12 | 2.24 | | | | | | | 90 | | 90 | | | | 40 | | 50 | | | | | | |
| | | | | | | | | | | | (0) | | | | | | (20) | | | | | | | |
| 5 | 0.56 | 12 | 2.24 | | | | | | | 70 | | 80 | 55 | | 75 | | | | | | | | | |
| | | | | | | | | | | | (13) | | | (27) | | | | | | | | | | |
| 5 | 0.56 | 12 | 2.24 | | | | 80 | | 95 | 85 | | 90 | | | | | | | 100 | | 100 | | | |
| | | | | | | | | (16) | | | (6) | | | | | | | | | (0) | | | | |
| 5 | 0.14 | 12 | 8.96 | | | | | | | 95 | | 85 | | | | 10 | | 28 | | | | | | |
| | | | | | | | | | | | | | | | | | (65) | | | | | | | |
| 5 | 0.14 | 12 | 8.96 | | | | | | | 80 | | 35 | 0 | | | | | | | | | | | |
| 5 | 0.14 | 12 | 8.96 | | | | 20 | | 32 | 60 | | 60 | | | | | | | 80 | | 100 | | | |
| | | | | | | | | (38) | | | (0) | | | | | | | | | (20) | | | | |
| 5 | 0.56 | 12 | 8.96 | | | | 35 | | 95 | 95 | | 90 | | | | | | | 100 | | 100 | | | |
| | | | | | | | | (64) | | | | | | | | | | | | (0) | | | | |
| 5 | 0.56 | 12 | 8.96 | | | | | | | 95 | | 90 | | | | 60 | | 50 | | | | | | |
| 5 | 0.56 | 12 | 8.96 | | | | | | | 85 | | 80 | 5 | | 75 | | | | | | | | | |
| | | | | | | | | | | | | | | (94) | | | | | | | | | | |
| 1 | 0.14 | 13 | 0.56 | | | | | | | | | | 38 | | 99 | | | | 60 | | 55 | | | |
| | | | | | | | | | | | | | | (62) | | | | | | | | | | |
| 1 | 0.56 | 13 | 0.56 | | | | | | | | | | 99 | | 100 | | | | | | | 70 | | 70 |
| | | | | | | | | | | | | | | (1) | | | | | | | | | (0) | |
| 1 | 0.03 | 13 | 1.12 | | | | | | | 0 | | | 0 | | | | | | | | | | | |
| 1 | 0.03 | 13 | 1.12 | 0 | | | 15 | | 25 | 55 | | 15 | | | | | | | | | | | | |
| | | | | | | | | (40) | | | | | | | | | | | | | | | | |
| 1 | 0.14 | 13 | 1.12 | 45 | | 58 | 85 | | 83 | 50 | | 50 | | | | | | | | | | | | |
| | | | | | (23) | | | | | | (0) | | | | | | | | | | | | | |
| 1 | 0.14 | 13 | 1.12 | | | | | | | 10 | | 75 | 0 | | 68 | | | | | | | | | |
| | | | | | | | | | | | (87) | | | (100) | | | | | | | | | | |
| 1 | 0.14 | 13 | 2.24 | | | | | | | | | | 53 | | 99 | | | | | | | 75 | | 55 |
| | | | | | | | | | | | | | | (47) | | | | | | | | | | |
| 1 | 0.56 | 13 | 2.24 | | | | | | | | | | 99 | | 100 | | | | | | | 70 | | 70 |
| | | | | | | | | | | | | | | (1) | | | | | | | | | (0) | |

-continued

| | | | | | | | | | | | | | | | | | | | | | |
|---|---|---|---|---|---|---|---|---|---|---|---|---|---|---|---|---|---|---|---|---|---|
| 1 | 0.03 | 13 | 4.48 | | | | | | | 0 | | | 0 | | | | | | | | |
| 1 | 0.03 | 13 | 4.48 | 10 | | | 5 | (80) | 25 | 10 | (34) | 15 | | | | | | | | | |
| 1 | 0.14 | 13 | 4.48 | 10 | (83) | 58 | 80 | (4) | 83 | 75 | | 50 | | | | | | | | | |
| 1 | 0.14 | 13 | 4.48 | | | | | | | 0 | (100) | 75 | 5 | (93) | 68 | | | | | | |
| 1 | 0.14 | 13 | 8.96 | | | | | | | | | | 73 | (27) | 99 | | | | 60 | | 55 |
| 1 | 0.56 | 13 | 8.96 | | | | | | | | | | 99 | (1) | 100 | | | | 70 | (0) | 70 |
| 2 | 0.14 | 13 | 0.56 | | | | | | | 10 | (84) | 60 | | | | 35 | (8) | 38 | | | |
| 2 | 0.14 | 13 | 0.56 | 10 | (77) | 43 | 90 | (3) | 92 | 50 | | 35 | | | | | | | | | |
| 2 | 0.56 | 13 | 0.56 | 95 | (0) | 95 | 95 | (0) | 95 | 95 | | 80 | | | | | | | | | |
| 2 | 0.56 | 13 | 0.56 | | | | | | | 95 | | 85 | | | | 95 | | 77 | | | |
| 2 | 0.14 | 13 | 1.12 | 80 | | 23 | 90 | | 52 | 15 | (69) | 48 | | | | | | | | | |
| 2 | 0.56 | 13 | 1.12 | 95 | (0) | 95 | 95 | (0) | 95 | 90 | (6) | 95 | | | | | | | | | |
| 2 | 0.14 | 13 | 2.24 | 35 | (19) | 43 | 90 | (3) | 92 | 60 | | 35 | | | | | | | | | |
| 2 | 0.14 | 13 | 2.24 | | | | | | | 35 | (42) | 60 | | | | 70 | | 38 | | | |
| 2 | 0.56 | 13 | 2.24 | | | | | | | 90 | | 85 | | | | 90 | | 77 | | | |
| 2 | 0.56 | 13 | 2.24 | 95 | (0) | 95 | 100 | | 95 | 95 | | 80 | | | | | | | | | |
| 2 | 0.14 | 13 | 4.48 | 25 | | 23 | 85 | | 52 | 0 | (100) | 48 | | | | | | | | | |
| 2 | 0.56 | 13 | 4.48 | 95 | (0) | 95 | 95 | (0) | 95 | 95 | (0) | 95 | | | | | | | | | |
| 2 | 0.14 | 13 | 8.96 | | | | | | | 45 | (25) | 60 | | | | 45 | | 38 | | | |
| 2 | 0.14 | 13 | 8.96 | 0 | (100) | 43 | 10 | (90) | 92 | 0 | (100) | 35 | | | | | | | | | |
| 2 | 0.56 | 13 | 8.96 | 65 | (32) | 95 | 95 | (0) | 95 | 70 | (13) | 80 | | | | | | | | | |
| 2 | 0.56 | 13 | 8.96 | | | | | | | 10 | (89) | 85 | | | | 85 | | 77 | | | |
| 4 | 0.14 | 13 | 0.56 | | | | | | | | | | 0 | (100) | 8 | | | | 70 | (0) | 70 |
| 4 | 0.56 | 13 | 0.56 | | | | | | | | | | 88 | (10) | 97 | | | | 80 | (6) | 85 |
| 4 | 1.12 | 13 | 0.56 | | | | | | | 70 | (0) | 70 | | | | 0 | (100) | 7 | | | |
| 4 | 2.24 | 13 | 0.56 | | | | | | | 70 | (5) | 73 | | | | 0 | (100) | 30 | | | |
| 4 | 0.14 | 13 | 1.12 | | | | | | | 15 | (63) | 40 | 0 | (100) | 12 | | | | | | |
| 4 | 0.56 | 13 | 1.12 | | | | | | | 70 | | 65 | 75 | | 53 | | | | | | |
| 4 | 0.14 | 13 | 2.24 | | | | | | | | | | 0 | (100) | 8 | | | | 70 | (0) | 70 |

-continued

| | | | | | | | | | | | | | | | | | | | | | | | | | | | |
|---|---|---|---|---|---|---|---|---|---|---|---|---|---|---|---|---|---|---|---|---|---|---|---|---|---|---|---|
| 4 | 0.56 | 13 | 2.24 | | | | | | | | | | 43 | (56) | 97 | | | | | | | | | | 85 | (0) | 85 |
| 4 | 1.12 | 13 | 2.24 | | | | | | | 60 | (15) | 70 | | | | | | | 0 | (100) | 7 | | | | | | |
| 4 | 2.24 | 13 | 2.24 | | | | | | | 100 | | 73 | | | | | | | 40 | | 30 | | | | | | |
| 4 | 0.14 | 13 | 4.48 | | | | | | | 45 | | 40 | 0 | (100) | 12 | | | | | | | | | | | | |
| 4 | 0.56 | 13 | 4.48 | | | | | | | 75 | | 65 | 30 | (44) | 53 | | | | | | | | | | | | |
| 4 | 0.14 | 13 | 8.96 | | | | | | | | | | 0 | (100) | 8 | | | | | | | | | | 75 | | 70 |
| 4 | 0.56 | 13 | 8.96 | | | | | | | | | | 8 | (92) | 97 | | | | | | | | | | 75 | (12) | 85 |
| 4 | 1.12 | 13 | 8.96 | | | | | | | 80 | | 70 | | | | | | | 20 | | 7 | | | | | | |
| 4 | 2.24 | 13 | 8.96 | | | | | | | 90 | | 73 | | | | | | | 35 | | 30 | | | | | | |
| 5 | 0.14 | 13 | 0.56 | | | | | | | 40 | | 35 | 0 | | | | | | | | | | | | | | |
| 5 | 0.14 | 13 | 0.56 | | | | 35 | | 32 | 80 | | 60 | | | | | | | | | | 100 | (0) | 100 | | | |
| 5 | 0.14 | 13 | 0.56 | | | | | | | 80 | (6) | 85 | | | | | | | 0 | (100) | 28 | | | | | | |
| 5 | 0.56 | 13 | 0.56 | | | | 60 | (37) | 95 | 95 | | 90 | | | | | | | | (0) | | 100 | | 100 | | | |
| 5 | 0.56 | 13 | 0.56 | | | | | | | 90 | (0) | 90 | | | | | | | 30 | (40) | 50 | | | | | | |
| 5 | 0.56 | 13 | 0.56 | | | | | | | 60 | (25) | 80 | 30 | (60) | 75 | | | | | | | | | | | | |
| 5 | 0.14 | 13 | 2.24 | | | | | | | 35 | (0) | 35 | 0 | | | | | | | | | | | | | | |
| 5 | 0.14 | 13 | 2.24 | | | | | | | 60 | (30) | 85 | | | | | | | 80 | | 28 | | | | | | |
| 5 | 0.14 | 13 | 2.24 | 50 | | 32 | 0 | | 60 | | (100) | | | | | | | | 80 | | 100 | | (20) | | | | |
| 5 | 0.56 | 13 | 2.24 | | | | | | | 35 | (57) | 80 | 0 | (100) | 75 | | | | | | | | | | | | |
| 5 | 0.56 | 13 | 2.24 | | | | 70 | (27) | 95 | 85 | (6) | 90 | | | | | | | | | | 100 | (0) | 100 | | | |
| 5 | 0.56 | 13 | 2.24 | | | | | | | 90 | (0) | 90 | | | | | | | 45 | (10) | 50 | | | | | | |
| 5 | 0.14 | 13 | 8.96 | | | | 10 | (69) | 32 | 35 | (42) | 60 | | | | | | | | | | 75 | (25) | 100 | | | |
| 5 | 0.14 | 13 | 8.96 | | | | | | | 55 | | 35 | 0 | | | | | | | | | | | | | | |
| 5 | 0.14 | 13 | 8.96 | | | | | | | 70 | (18) | 85 | | | | | | | 60 | | 28 | | | | | | |
| 5 | 0.56 | 13 | 8.96 | | | | 55 | (43) | 95 | 95 | | 90 | | | | | | | | | | 100 | (0) | 100 | | | |
| 5 | 0.56 | 13 | 8.96 | | | | | | | 70 | (13) | 80 | 0 | (100) | 75 | | | | | | | | | | | | |
| 5 | 0.56 | 13 | 8.96 | | | | | | | 95 | | 90 | | | | | | | 65 | | 50 | | | | | | |
| 1 | 0.03 | 14 | 0.56 | 0 | (100) | 35 | 0 | (100) | 45 | 80 | | 65 | 20 | (20) | 25 | 10 | (60) | 25 | | | | | | | | | |
| 1 | 0.14 | 14 | 0.56 | 100 | | 95 | 95 | (3) | 97 | 95 | | 90 | 90 | | 80 | 25 | (50) | 50 | | | | | | | | | |
| 1 | 0.03 | 14 | 2.24 | 5 | (86) | 35 | 0 | (100) | 45 | 95 | | 65 | 15 | (40) | 25 | 20 | (20) | 25 | | | | | | | | | |

-continued

| | | | | | | | | | | | | | | | | | | | | | |
|---|---|---|---|---|---|---|---|---|---|---|---|---|---|---|---|---|---|---|---|---|---|
| 1 | 0.14 | 14 | 2.24 | 60 | (37) | 95 | 90 | (8) | 97 | 95 | | 90 | 80 | (0) | 80 | 40 | (20) | 50 | | | |
| 1 | 0.03 | 14 | 8.96 | 10 | (72) | 35 | 0 | (100) | 45 | 100 | | 65 | 10 | (60) | 25 | 10 | (60) | 25 | | | |
| 1 | 0.14 | 14 | 8.96 | 35 | (64) | 95 | 25 | (75) | 97 | 100 | | 90 | 50 | (38) | 80 | 40 | (20) | 50 | | | |
| 2 | 0.14 | 14 | 0.56 | 0 | (100) | 43 | 70 | (24) | 92 | 20 | (43) | 35 | | | | | | | | | |
| 2 | 0.14 | 14 | 0.56 | | | | | | | 20 | (67) | 60 | | | | | | | 10 | (74) | 38 |
| 2 | 0.28 | 14 | 0.56 | | | | | | | 100 | | 98 | 95 | | 82 | | | | | | |
| 2 | 0.28 | 14 | 0.56 | | | | | | | 60 | (0) | 60 | 35 | (62) | 92 | | | | | | |
| 2 | 0.56 | 14 | 0.56 | | | | | | | 100 | | 85 | | | | | | | 80 | | 77 |
| 2 | 0.56 | 14 | 0.56 | 95 | (0) | 95 | 95 | (0) | 95 | 65 | (19) | 80 | | | | | | | | | |
| 2 | 1.12 | 14 | 0.56 | | | | | | | 100 | (0) | 100 | 100 | (0) | 100 | | | | | | |
| 2 | 1.12 | 14 | 0.56 | | | | | | | 85 | | 70 | 100 | (0) | 100 | | | | | | |
| 2 | 0.14 | 14 | 2.24 | 65 | | 43 | 70 | (24) | 92 | 75 | | 35 | | | | | | | | | |
| 2 | 0.14 | 14 | 2.24 | | | | | | | 10 | (84) | 60 | | | | | | | 5 | (87) | 38 |
| 2 | 0.28 | 14 | 2.24 | | | | | | | 100 | | 98 | 100 | | 82 | | | | | | |
| 2 | 0.28 | 14 | 2.24 | | | | | | | 85 | | 60 | 95 | | 92 | | | | | | |
| 2 | 0.56 | 14 | 2.24 | 95 | (0) | 95 | 95 | (0) | 95 | 70 | (13) | 80 | | | | | | | | | |
| 2 | 0.56 | 14 | 2.24 | | | | | | | 90 | | 85 | | | | | | | 95 | | 77 |
| 2 | 1.12 | 14 | 2.24 | | | | | | | 95 | (5) | 100 | 100 | (0) | 100 | | | | | | |
| 2 | 1.12 | 14 | 2.24 | | | | | | | 95 | | 70 | 95 | (5) | 100 | | | | | | |
| 2 | 0.14 | 14 | 8.96 | | | | | | | 100 | | 60 | | | | | | | 20 | (48) | 38 |
| 2 | 0.14 | 14 | 8.96 | 85 | | 43 | 75 | (19) | 92 | 90 | | 35 | | | | | | | | | |
| 2 | 0.28 | 14 | 8.96 | | | | | | | 100 | | 98 | 95 | | 82 | | | | | | |
| 2 | 0.28 | 14 | 8.96 | | | | | | | 95 | | 60 | 60 | (35) | 92 | | | | | | |
| 2 | 0.56 | 14 | 8.96 | 95 | (0) | 95 | 95 | (0) | 95 | 95 | | 80 | | | | | | | | | |
| 2 | 0.56 | 14 | 8.96 | | | | | | | 80 | (6) | 85 | | | | | | | 85 | | 77 |
| 2 | 1.12 | 14 | 8.96 | | | | | | | 100 | (0) | 100 | 100 | (0) | 100 | | | | | | |
| 2 | 1.12 | 14 | 8.96 | | | | | | | 95 | | 70 | 95 | (5) | 100 | | | | | | |
| 3 | 2.24 | 14 | 0.56 | | | | | | | 25 | (55) | 55 | 5 | (50) | 10 | | | | | | |
| 3 | 4.48 | 14 | 0.56 | | | | | | | 15 | (73) | 55 | 20 | (50) | 40 | | | | | | |
| 3 | 2.24 | 14 | 2.24 | | | | | | | 90 | | 55 | 10 | (0) | 10 | | | | | | |

-continued

| | | | | | | | | | | | | | | | | | | |
|---|---|---|---|---|---|---|---|---|---|---|---|---|---|---|---|---|---|---|
| 3 | 4.48 | 14 | 2.24 | | | | | | | 70 | | 55 | 5 | (88) | 40 | | | |
| 3 | 2.24 | 14 | 8.96 | | | | | | | 90 | | 55 | 5 | (50) | 10 | | | |
| 3 | 4.48 | 14 | 8.96 | | | | | | | 90 | | 55 | 5 | (88) | 40 | | | |
| 4 | 0.14 | 14 | 0.56 | 100 | | 98 | 100 | | 98 | 100 | | 95 | | | | | | |
| 4 | 0.56 | 14 | 0.56 | 100 | (0) | 100 | 100 | (0) | 100 | 95 | (5) | 100 | | | | | | |
| 4 | 0.56 | 14 | 0.56 | | | | | | | 85 | | 80 | 90 | (0) | 90 | | | |
| 4 | 1.12 | 14 | 0.56 | | | | | | | 95 | | 80 | 95 | (3) | 97 | | | |
| 4 | 1.12 | 14 | 0.56 | | | | | | | 55 | (22) | 70 | | | | 10 | | 7 |
| 4 | 2.24 | 14 | 0.56 | | | | | | | 70 | (5) | 73 | | | | 0 | (100) | 30 |
| 4 | 0.14 | 14 | 2.24 | 95 | (4) | 98 | 75 | (24) | 98 | 90 | (6) | 95 | | | | | | |
| 4 | 0.56 | 14 | 2.24 | | | | | | | 90 | | 80 | 75 | (17) | 90 | | | |
| 4 | 0.56 | 14 | 2.24 | 100 | (0) | 100 | 100 | (0) | 100 | 95 | (5) | 100 | | | | | | |
| 4 | 1.12 | 14 | 2.24 | | | | | | | 85 | | 80 | 90 | (8) | 97 | | | |
| 4 | 1.12 | 14 | 2.24 | | | | | | | 70 | (0) | 70 | | | | 20 | | 7 |
| 4 | 2.24 | 14 | 2.24 | | | | | | | 70 | (5) | 73 | | | | 30 | (0) | 30 |
| 4 | 0.14 | 14 | 8.96 | 100 | | 98 | 95 | (4) | 98 | 100 | | 95 | | | | | | |
| 4 | 1.12 | 14 | 0.56 | | | | | | | 95 | | 80 | 95 | (3) | 97 | | | |
| 4 | 1.12 | 14 | 0.56 | | | | | | | 55 | (22) | 70 | | | | 10 | | 7 |
| 4 | 2.24 | 14 | 0.56 | | | | | | | 70 | (5) | 73 | | | | 0 | (100) | 30 |
| 4 | 0.14 | 14 | 2.24 | 95 | (4) | 98 | 75 | (24) | 98 | 90 | (6) | 95 | | | | | | |
| 4 | 0.56 | 14 | 2.24 | | | | | | | 90 | | 80 | 75 | (17) | 90 | | | |
| 4 | 0.56 | 14 | 2.24 | 100 | (0) | 100 | 100 | (0) | 100 | 95 | (5) | 100 | | | | | | |
| 4 | 1.12 | 14 | 2.24 | | | | | | | 85 | | 80 | 90 | (8) | 97 | | | |
| 4 | 1.12 | 14 | 2.24 | | | | | | | 70 | (0) | 70 | | | | 20 | | 7 |
| 4 | 2.24 | 14 | 2.24 | | | | | | | 70 | (5) | 73 | | | | 30 | (0) | 30 |
| 4 | 0.14 | 14 | 8.96 | 100 | | 98 | 95 | (4) | 98 | 100 | | 95 | | | | | | |
| 4 | 0.56 | 14 | 8.96 | 100 | (0) | 100 | 100 | (0) | 100 | 100 | (0) | 100 | | | | | | |
| 4 | 0.56 | 14 | 8.96 | | | | | | | 95 | | 80 | 70 | | 90 | | | |

-continued

| | | | | | | | | | | | | | | | | | | | | | | | | |
|---|---|---|---|---|---|---|---|---|---|---|---|---|---|---|---|---|---|---|---|---|---|---|---|---|
| | | | | | | | | | | | | | | (23) | | | | | | | | | | |
| 4 | 1.12 | 14 | 8.96 | | | | | | | 75 | | 70 | | | | | | | 10 | | 7 | | | |
| 4 | 1.12 | 14 | 8.96 | | | | | | | 95 | | 80 | 95 | | 97 | | | | | | | | | |
| | | | | | | | | | | | | | | (3) | | | | | | | | | | |
| 4 | 2.24 | 14 | 8.96 | | | | | | | 90 | | 73 | | | | | | | 45 | | 30 | | | |
| 5 | 0.14 | 14 | 0.56 | | | | | | | 45 | | 35 | 0 | | | | | | | | | | | |
| 5 | 0.14 | 14 | 0.56 | | | | | | | 55 | | 85 | | | | | | | 20 | | 28 | | | |
| | | | | | | | | | | | (36) | | | | | | | | | (29) | | | | |
| 5 | 0.14 | 14 | 0.56 | | | | 30 | | 32 | 70 | | 60 | | | | | | | | | | 95 | | 100 |
| | | | | | | | | (7) | | | | | | | | | | | | | | | (5) | |
| 5 | 0.56 | 14 | 0.56 | | | | | | | 80 | | 90 | | | | | | | 40 | | 50 | | | |
| | | | | | | | | | | | (12) | | | | | | | | | (20) | | | | |
| 5 | 0.56 | 14 | 0.56 | | | | 95 | | 95 | 90 | | 90 | | | | | | | | | | 100 | | 100 |
| | | | | | | | | (0) | | | (0) | | | | | | | | | | | | (0) | |
| 5 | 0.56 | 14 | 0.56 | | | | | | | 70 | | 80 | 0 | | 75 | | | | | | | | | |
| | | | | | | | | | | | (13) | | | (100) | | | | | | | | | | |
| 5 | 0.14 | 14 | 2.24 | | | | | | | 50 | | 35 | 0 | | | | | | | | | | | |
| 5 | 0.14 | 14 | 2.24 | | | | 10 | | 32 | 55 | | 60 | | | | | | | | | | 100 | | 100 |
| | | | | | | | | (69) | | | (9) | | | | | | | | | | | | (0) | |
| 5 | 0.14 | 14 | 2.24 | | | | | | | 50 | | 85 | | | | | | | 80 | | 28 | | | |
| | | | | | | | | | | | (42) | | | | | | | | | | | | | |
| 5 | 0.56 | 14 | 2.24 | | | | | | | 90 | | 90 | | | | | | | 30 | | 50 | | | |
| | | | | | | | | | | | (0) | | | | | | | | | (40) | | | | |
| 5 | 0.56 | 14 | 2.24 | | | | 55 | | 95 | 95 | | 90 | | | | | | | | | | 100 | | 100 |
| | | | | | | | | (43) | | | | | | | | | | | | | | | (0) | |
| 5 | 0.56 | 14 | 2.24 | | | | | | | 40 | | 80 | 25 | | 75 | | | | | | | | | |
| | | | | | | | | | | | (50) | | | (67) | | | | | | | | | | |
| 5 | 0.14 | 14 | 8.96 | | | | | | | 65 | | 35 | 0 | | | | | | | | | | | |
| 5 | 0.14 | 14 | 8.96 | | | | 35 | | 32 | 60 | | 60 | | | | | | | | | | 90 | | 100 |
| | | | | | | | | | | | (0) | | | | | | | | | | | | (10) | |
| 5 | 0.14 | 14 | 8.96 | | | | | | | 90 | | 85 | | | | | | | 55 | | 28 | | | |
| 5 | 0.56 | 14 | 8.96 | | | | 85 | | 95 | 90 | | 90 | | | | | | | | | | 100 | | 100 |
| | | | | | | | | (11) | | | (0) | | | | | | | | | | | | (0) | |
| 5 | 0.56 | 14 | 8.96 | | | | | | | 80 | | 90 | | | | | | | 30 | | 50 | | | |
| | | | | | | | | | | | (12) | | | | | | | | | (40) | | | | |
| 5 | 0.56 | 14 | 8.96 | | | | | | | 70 | | 80 | 15 | | 75 | | | | | | | | | |
| | | | | | | | | | | | (13) | | | (80) | | | | | | | | | | |
| 1 | 0.03 | 15 | 0.56 | 10 | | 35 | 50 | | 45 | 95 | | 65 | 0 | | 25 | 10 | | 25 | | | | | | |
| | | | | | (72) | | | | | | | | | (100) | | | (60) | | | | | | | |
| 1 | 0.14 | 15 | 0.56 | 80 | | 95 | 75 | | 97 | 95 | | 90 | 85 | | 80 | 40 | | 50 | | | | | | |
| | | | | | (16) | | | (23) | | | | | | | | | (20) | | | | | | | |
| 1 | 0.03 | 15 | 2.24 | 0 | | 35 | 0 | | 45 | 95 | | 65 | 25 | | 25 | 15 | | 25 | | | | | | |
| | | | | | (100) | | | (100) | | | | | | (0) | | | (40) | | | | | | | |
| 1 | 0.14 | 15 | 2.24 | 90 | | 95 | 100 | | 97 | 95 | | 90 | 90 | | 80 | 35 | | 50 | | | | | | |
| | | | | | (6) | | | | | | | | | | | | (30) | | | | | | | |
| 1 | 0.03 | 15 | 8.96 | 0 | | 35 | 0 | | 45 | 90 | | 65 | 20 | | 25 | 10 | | 25 | | | | | | |
| | | | | | (100) | | | (100) | | | | | | (20) | | | (60) | | | | | | | |
| 1 | 0.14 | 15 | 8.96 | 65 | | 95 | 0 | | 97 | 90 | | 90 | 85 | | 80 | 40 | | 50 | | | | | | |
| | | | | | (32) | | | (100) | | | (0) | | | | | | (20) | | | | | | | |
| 2 | 0.14 | 15 | 0.56 | | | | | | | 70 | | 60 | | | | | | | 25 | | 38 | | | |
| | | | | | | | | | | | | | | | | | | | | (35) | | | | |
| 5 | 0.14 | 14 | 8.96 | | | | 35 | | 32 | 60 | | 60 | | | | | | | | | | 90 | | 100 |
| | | | | | | | | | | | (0) | | | | | | | | | | | | (10) | |
| | | | | (100) | | | (100) | | | | | | (0) | | | (40) | | | | | | | | |

-continued

| | | | | | | | | | | | | | | | |
|---|---|---|---|---|---|---|---|---|---|---|---|---|---|---|---|
| 1 | 0.14 | 15 | 2.24 | 90 | (6) 95 | 100 | 97 | 95 | 90 | 90 | 80 | 35 | (30) 50 | | |
| 1 | 0.03 | 15 | 8.96 | 0 | (100) 35 | 0 | (100) 45 | 90 | 65 | 20 | (20) 25 | 10 | (60) 25 | | |
| 1 | 0.14 | 15 | 8.96 | 65 | (32) 95 | 0 | (100) 97 | 90 | (0) 90 | 85 | 80 | 40 | (20) 50 | | |
| 2 | 0.14 | 15 | 0.56 | | | | | 70 | 60 | | | | | 25 | (35) 38 |

| | | | | | | | | | | | | | | | | | | | | | | |
|---|---|---|---|---|---|---|---|---|---|---|---|---|---|---|---|---|---|---|---|---|---|---|
| 5 | 0.14 | 14 | 8.96 | | | | | | | 90 | | 85 | | | | | | | 55 | | 28 | |
| 5 | 0.56 | 14 | 8.96 | 85 | | 95 | 90 | | 90 | | | | | | | | | | 100 | | 100 | |
| | | | | | | | | (11) | | | (0) | | | | | | | | | | | (0) |
| 5 | 0.56 | 14 | 8.96 | | | | | | | 80 | | 90 | | | | | | | 30 | | 50 | |
| | | | | | | | | | | | (12) | | | | | | | | | (40) | | |
| 5 | 0.56 | 14 | 8.96 | | | | | | | 70 | | 80 | 15 | | 75 | | | | | | | |
| | | | | | | | | | | | (13) | | | (80) | | | | | | | | |
| 1 | 0.03 | 15 | 0.56 | 10 | | 35 | 50 | | 45 | 95 | | 65 | 0 | | 25 | 10 | | 25 | | | | |
| | | | | | (72) | | | | | | | | | (100) | | | (60) | | | | | |
| 1 | 0.14 | 15 | 0.56 | 80 | | 95 | 75 | | 97 | 95 | | 90 | 85 | | 80 | 40 | | 50 | | | | |
| | | | | | (16) | | | (23) | | | | | | | | | (20) | | | | | |
| 1 | 0.03 | 15 | 2.24 | 0 | | 35 | 0 | | 45 | 95 | | 65 | 25 | | 25 | 15 | | 25 | | | | |
| | | | | | (100) | | | (100) | | | | | | (0) | | | (40) | | | | | |
| 1 | 0.14 | 15 | 2.24 | 90 | | 95 | 100 | | 97 | 95 | | 90 | 90 | | 80 | 35 | | 50 | | | | |
| | | | | | (6) | | | | | | | | | | | | (30) | | | | | |
| 1 | 0.03 | 15 | 8.96 | 0 | | 35 | 0 | | 45 | 90 | | 65 | 20 | | 25 | 10 | | 25 | | | | |
| | | | | | (100) | | | (100) | | | | | | (20) | | | (60) | | | | | |
| 1 | 0.14 | 15 | 8.96 | 65 | | 95 | 0 | | 97 | 90 | | 90 | 85 | | 80 | 40 | | 50 | | | | |
| | | | | | (32) | | | (100) | | | (0) | | | | | | (20) | | | | | |
| 2 | 0.14 | 15 | 0.56 | | | | | | | 70 | | 60 | | | | | | | 25 | | 38 | |
| | | | | | | | | | | | | | | | | | | | | (35) | | |
| 2 | 0.14 | 15 | 0.56 | 10 | | 43 | 65 | | 92 | 10 | | 35 | | | | | | | | | | |
| | | | | | (77) | | | (30) | | | (72) | | | | | | | | | | | |
| 2 | 0.28 | 15 | 0.56 | | | | | | | 100 | | 98 | 100 | | 82 | | | | | | | |
| 2 | 0.28 | 15 | 0.56 | | | | | | | 80 | | 60 | 85 | | 92 | | | | | | | |
| | | | | | | | | | | | | | | (8) | | | | | | | | |
| 2 | 0.56 | 15 | 0.56 | | | | | | | 85 | | 85 | | | | | | | 80 | | 77 | |
| | | | | | | | | | | | (0) | | | | | | | | | | | |
| 2 | 0.56 | 15 | 0.56 | 80 | | 95 | 95 | | 95 | 75 | | 80 | | | | | | | | | | |
| | | | | | (16) | | | (0) | | | (7) | | | | | | | | | | | |
| 2 | 1.12 | 15 | 0.56 | | | | | | | 100 | | 100 | 100 | | 100 | | | | | | | |
| | | | | | | | | | | | (0) | | | (0) | | | | | | | | |
| 2 | 1.12 | 15 | 0.56 | | | | | | | 75 | | 70 | 100 | | 100 | | | | | | | |
| | | | | | | | | | | | | | | (0) | | | | | | | | |
| 2 | 0.14 | 15 | 2.24 | | | | | | | 10 | | 60 | | | | | | | 50 | | 38 | |
| | | | | | | | | | | | (84) | | | | | | | | | | | |
| 2 | 0.14 | 15 | 2.24 | 45 | | 43 | 95 | | 92 | 85 | | 35 | | | | | | | | | | |
| 2 | 0.28 | 15 | 2.24 | | | | | | | 100 | | 98 | 75 | | 82 | | | | | | | |
| | | | | | | | | | | | | | | (9) | | | | | | | | |
| 2 | 0.28 | 15 | 2.24 | | | | | | | 50 | | 60 | 90 | | 92 | | | | | | | |
| | | | | | | | | | | | (17) | | | (3) | | | | | | | | |
| 2 | 0.56 | 15 | 2.24 | 95 | | 95 | 95 | | 95 | 85 | | 80 | | | | | | | | | | |
| | | | | | (0) | | | (0) | | | | | | | | | | | | | | |
| 2 | 0.56 | 15 | 2.24 | | | | | | | 90 | | 85 | | | | | | | 95 | | 77 | |
| 2 | 1.12 | 15 | 2.24 | | | | | | | 100 | | 100 | 100 | | 100 | | | | | | | |
| | | | | | | | | | | | (0) | | | (0) | | | | | | | | |
| 2 | 1.12 | 15 | 2.24 | | | | | | | 50 | | 70 | 100 | | 100 | | | | | | | |
| | | | | | | | | | | | (29) | | | (0) | | | | | | | | |
| 2 | 0.14 | 15 | 8.96 | | | | | | | 75 | | 60 | | | | | | | 55 | | 38 | |
| 2 | 0.14 | 15 | 8.96 | 10 | | 43 | 95 | | 92 | 90 | | 35 | | | | | | | | | | |
| | | | | | (77) | | | | | | | | | | | | | | | | | |
| 2 | 0.28 | 15 | 8.96 | | | | | | | 95 | | 98 | 95 | | 82 | | | | | | | |
| | | | | | | | | | | | (4) | | | | | | | | | | | |
| 2 | 0.28 | 15 | 8.96 | | | | | | | 70 | | 60 | 100 | | 92 | | | | | | | |

-continued

| | | | | | | | | | | | | | | | | | | |
|---|---|---|---|---|---|---|---|---|---|---|---|---|---|---|---|---|---|---|
| 2 | 0.56 | 15 | 8.96 | | | | | | | 90 | | 85 | | | | 95 | | 77 |
| 2 | 0.56 | 15 | 8.96 | 95 | (0) | 95 | 95 | (0) | 95 | 90 | | 80 | | | | | | |
| 2 | 1.12 | 15 | 8.96 | | | | | | | 45 | (36) | 70 | 100 | (0) | 100 | | | |
| 2 | 1.12 | 15 | 8.96 | 100 | | 100 | 100 | | 100 | | (0) | | | (0) | | | | |
| 3 | 2.24 | 15 | 0.56 | | | | | | | 60 | | 55 | 5 | (50) | 10 | | | |
| 3 | 4.48 | 15 | 0.56 | | | | | | | 70 | | 55 | 15 | (63) | 40 | | | |
| 3 | 2.24 | 15 | 2.24 | | | | | | | 10 | (82) | 55 | 25 | | 10 | | | |
| 3 | 4.48 | 15 | 2.24 | | | | | | | 40 | (28) | 55 | 20 | (50) | 40 | | | |
| 3 | 2.24 | 15 | 8.96 | | | | | | | 40 | (28) | 55 | 0 | (100) | 10 | | | |
| 3 | 4.48 | 15 | 8.96 | | | | | | | 50 | (10) | 55 | 10 | (75) | 40 | | | |
| 4 | 0.14 | 15 | 0.56 | 100 | | 98 | 95 | (4) | 98 | 100 | | 95 | | | | | | |
| 4 | 0.56 | 15 | 0.56 | | | | | | | 55 | (32) | 80 | 95 | | 90 | | | |
| 4 | 0.56 | 15 | 0.56 | 95 | (5) | 100 | 100 | (0) | 100 | 100 | (0) | 100 | | | | | | |
| 4 | 1.12 | 15 | 0.56 | | | | | | | 90 | | 80 | 100 | | 97 | | | |
| 4 | 1.12 | 15 | 0.56 | | | | | | | 55 | (22) | 70 | | | | 0 | (100) | 7 |
| 4 | 2.24 | 15 | 0.56 | | | | | | | 75 | | 73 | | | | 5 | (84) | 30 |
| 4 | 0.14 | 15 | 2.24 | 100 | | 98 | 95 | (4) | 98 | 95 | (0) | 95 | | | | | | |
| 4 | 0.56 | 15 | 2.24 | 100 | (0) | 100 | 100 | (0) | 100 | 95 | (5) | 100 | | | | | | |
| 4 | 0.56 | 15 | 2.24 | | | | | | | 40 | (50) | 80 | 40 | (56) | 90 | | | |
| 4 | 1.12 | 15 | 2.24 | | | | | | | 65 | (19) | 80 | 95 | (3) | 97 | | | |
| 4 | 1.12 | 15 | 2.24 | | | | | | | 85 | | 70 | | | | 0 | (100) | 7 |
| 4 | 2.24 | 15 | 2.24 | | | | | | | 55 | (25) | 73 | | | | 20 | (34) | 30 |
| 4 | 0.14 | 15 | 8.96 | 100 | | 98 | 80 | (19) | 98 | 95 | (0) | 95 | | | | | | |
| 4 | 0.56 | 15 | 8.96 | 100 | (0) | 100 | 100 | (0) | 100 | 95 | (5) | 100 | | | | | | |
| 4 | 0.56 | 15 | 8.96 | | | | | | | 70 | (13) | 80 | 80 | (12) | 90 | | | |
| 4 | 1.12 | 15 | 8.96 | | | | | | | 65 | (19) | 80 | 90 | (8) | 97 | | | |
| 4 | 1.12 | 15 | 8.96 | | | | | | | 60 | (15) | 70 | | | | 0 | (100) | 7 |
| 4 | 2.24 | 15 | 8.96 | | | | | | | 60 | (18) | 73 | | | | 5 | (84) | 30 |

-continued

| | | | | | | | | | | | | | | | | | | | | | | | | |
|---|---|---|---|---|---|---|---|---|---|---|---|---|---|---|---|---|---|---|---|---|---|---|---|---|
| 5 | 0.14 | 15 | 0.56 | | | | | | | 45 | (48) | 85 | | | | | | | 20 | (29) | 28 | | | |
| 5 | 0.14 | 15 | 0.56 | | | | 30 | (7) | 32 | 15 | (75) | 60 | | | | | | | | | | 95 | (5) | 100 |
| 5 | 0.14 | 15 | 0.56 | | | | | | | 60 | | 35 | 0 | | | | | | | | | | | |
| 5 | 0.56 | 15 | 0.56 | | | | | | | 55 | (32) | 80 | 10 | (87) | 75 | | | | | | | | | |
| 5 | 0.56 | 15 | 0.56 | | | | 95 | (0) | 95 | 95 | | 90 | | | | | | | | | | 100 | (0) | 100 |
| 5 | 0.56 | 15 | 0.56 | | | | | | | 90 | (0) | 90 | | | | | | | 50 | (0) | 50 | | | |
| 5 | 0.14 | 15 | 2.24 | | | | 50 | (100) | 32 | 0 | | 60 | | | | | | | | (40) | | 60 | | 100 |
| 5 | 0.14 | 15 | 2.24 | | | | | | | 55 | (36) | 85 | | | | | | | 40 | | 28 | | | |
| 5 | 0.14 | 15 | 2.24 | | | | | | | 20 | (43) | 35 | 0 | | | | | | | | | | | |
| 5 | 0.56 | 15 | 2.24 | | | | | | | 70 | (13) | 80 | 0 | (100) | 75 | | | | | | | | | |
| 5 | 0.56 | 15 | 2.24 | | | | 80 | (16) | 95 | 70 | (23) | 90 | | | | | | | | | | 100 | (0) | 100 |
| 5 | 0.56 | 15 | 2.24 | | | | | | | 85 | (6) | 90 | | | | | | | 50 | (0) | 50 | | | |
| 5 | 0.14 | 15 | 8.96 | | | | | | | 90 | | 85 | | | | | | | 0 | (100) | 28 | | | |
| 5 | 0.14 | 15 | 8.96 | | | | 20 | (38) | 32 | 70 | | 60 | | | | | | | | | | 95 | (5) | 100 |
| 5 | 0.14 | 15 | 8.96 | | | | | | | 55 | | 35 | 0 | | | | | | | | | | | |
| 5 | 0.56 | 15 | 8.96 | | | | | | | 65 | (19) | 80 | 30 | (60) | 75 | | | | | | | | | |
| 5 | 0.56 | 15 | 8.96 | | | | 70 | (27) | 95 | 95 | | 90 | | | | | | | | | | 100 | (0) | 100 |
| 5 | 0.56 | 15 | 8.96 | | | | | | | 90 | (0) | 90 | | | | | | | 75 | | 50 | | | |
| 1 | 0.03 | 16 | 0.56 | 55 | | 35 | 75 | | 45 | 95 | | 65 | 0 | (100) | 25 | 30 | | 25 | | | | | | |
| 1 | 0.14 | 16 | 0.56 | 0 | (100) | 95 | 90 | (8) | 97 | 100 | | 90 | 75 | (7) | 80 | 45 | (10) | 50 | | | | | | |
| 1 | 0.03 | 16 | 2.24 | 20 | (43) | 35 | 55 | | 45 | 100 | | 65 | 5 | (80) | 25 | 10 | (60) | 25 | | | | | | |
| 1 | 0.14 | 16 | 2.24 | 80 | (16) | 95 | 100 | | 97 | 95 | | 90 | 80 | (0) | 80 | 35 | (30) | 50 | | | | | | |
| 1 | 0.03 | 16 | 8.96 | 0 | (100) | 35 | 70 | | 45 | 95 | | 65 | 10 | (60) | 25 | 25 | (0) | 25 | | | | | | |
| 1 | 0.14 | 16 | 8.96 | 80 | (16) | 95 | 90 | (8) | 97 | 95 | | 90 | 85 | | 80 | 40 | (20) | 50 | | | | | | |
| 2 | 0.14 | 16 | 0.56 | 0 | (100) | 43 | 30 | (68) | 92 | 15 | (58) | 35 | | | | | | | | | | | | |
| 2 | 0.14 | 16 | 0.56 | | | | | | | 55 | (9) | 60 | | | | | | | 15 | (61) | 38 | | | |
| 2 | 0.28 | 16 | 0.56 | | | | | | | 100 | | 98 | 75 | (9) | 82 | | | | | | | | | |
| 2 | 0.28 | 16 | 0.56 | | | | | | | 70 | | 60 | 70 | (24) | 92 | | | | | | | | | |

-continued

| | | | | | | | | | | | | | | | | | | |
|---|---|---|---|---|---|---|---|---|---|---|---|---|---|---|---|---|---|---|
| 2 | 0.56 | 16 | 0.56 | | | | | | | 85 | (0) | 85 | | | | 95 | | 77 |
| 2 | 0.56 | 16 | 0.56 | 95 | (0) | 95 | 95 | (0) | 95 | 70 | (13) | 80 | | | | | | |
| 2 | 1.12 | 16 | 0.56 | | | | | | | 100 | (0) | 100 | 100 | (0) | 100 | | | |
| 2 | 1.12 | 16 | 0.56 | | | | | | | 90 | | 70 | 95 | (5) | 100 | | | |
| 2 | 0.14 | 16 | 2.24 | 25 | (42) | 43 | 55 | (41) | 92 | 80 | | 35 | | | | | | |
| 2 | 0.14 | 16 | 2.24 | | | | | | | 90 | | 60 | | | | 45 | | 38 |
| 2 | 0.28 | 16 | 2.24 | | | | | | | 95 | (4) | 98 | 100 | | 82 | | | |
| 2 | 0.28 | 16 | 2.24 | | | | | | | 80 | | 60 | 75 | (19) | 92 | | | |
| 2 | 0.56 | 16 | 2.24 | 90 | (6) | 95 | 95 | (0) | 95 | 90 | | 80 | | | | | | |
| 2 | 0.56 | 16 | 2.24 | | | | | | | 100 | | 85 | | | | 95 | | 77 |
| 2 | 1.12 | 16 | 2.24 | | | | | | | 95 | (5) | 100 | 100 | (0) | 100 | | | |
| 2 | 1.12 | 16 | 2.24 | | | | | | | 90 | | 70 | 100 | (0) | 100 | | | |
| 2 | 0.14 | 16 | 8.96 | | | | | | | 95 | | 60 | | | | 30 | (22) | 38 |
| 2 | 0.14 | 16 | 8.96 | 60 | | 43 | 20 | (79) | 92 | 100 | | 35 | | | | | | |
| 2 | 0.28 | 16 | 8.96 | | | | | | | 95 | (4) | 98 | 95 | | 82 | | | |
| 2 | 0.28 | 16 | 8.96 | | | | | | | 90 | | 60 | 95 | | 92 | | | |
| 2 | 0.56 | 16 | 8.96 | 95 | (0) | 95 | 95 | (0) | 95 | 90 | | 80 | | | | | | |
| 2 | 0.56 | 16 | 8.96 | | | | | | | 90 | | 85 | | | | 95 | | 77 |
| 2 | 1.12 | 16 | 8.96 | | | | | | | 100 | (0) | 100 | 100 | (0) | 100 | | | |
| 2 | 1.12 | 16 | 8.96 | | | | | | | 90 | | 70 | 100 | (0) | 100 | | | |
| 2 | 2.24 | 16 | 0.56 | | | | | | | 20 | (64) | 55 | 0 | (100) | 10 | | | |
| 3 | 4.48 | 16 | 0.56 | | | | | | | 60 | | 55 | 10 | (75) | 40 | | | |
| 3 | 2.24 | 16 | 2.24 | | | | | | | 25 | (55) | 55 | 10 | (0) | 10 | | | |
| 3 | 4.48 | 16 | 2.24 | | | | | | | 60 | | 55 | 55 | | 40 | | | |
| 3 | 2.24 | 16 | 8.96 | | | | | | | 75 | | 55 | 5 | (50) | 10 | | | |
| 3 | 4.48 | 16 | 8.96 | | | | | | | 100 | | 55 | 35 | (13) | 40 | | | |
| 4 | 0.14 | 16 | 0.56 | 95 | (4) | 98 | 90 | (9) | 98 | 95 | (0) | 95 | | | | | | |
| 4 | 0.56 | 16 | 0.56 | 100 | (0) | 100 | 100 | (0) | 100 | 100 | (0) | 100 | | | | | | |
| 4 | 0.56 | 16 | 0.56 | | | | | | | 85 | | 80 | 90 | (0) | 90 | | | |
| 4 | 1.12 | 16 | 0.56 | | | | | | | 95 | | 80 | 95 | | 97 | | | |

-continued

| | | | | | | | | | | | | | | | | | | | | | |
|---|---|---|---|---|---|---|---|---|---|---|---|---|---|---|---|---|---|---|---|---|---|
| | | | | | | | | | | | | | | (3) | | | | | | | |
| 4 | 1.12 | 16 | 0.56 | | | | | | | 65 | (8) | 70 | | | | 35 | | 7 | | | |
| 4 | 2.24 | 16 | 0.56 | | | | | | | 75 | | 73 | | | | 10 | (67) | 30 | | | |
| 4 | 0.14 | 16 | 2.24 | 90 | (9) | 98 | 85 | (14) | 98 | 95 | (0) | 95 | | | | | | | | | |
| 4 | 0.56 | 16 | 2.24 | | | | | | | 95 | | 80 | 60 | (34) | 90 | | | | | | |
| 4 | 0.56 | 16 | 2.24 | 100 | (0) | 100 | 100 | (0) | 100 | 95 | (5) | 100 | | | | | | | | | |
| 4 | 1.12 | 16 | 2.24 | | | | | | | 95 | | 80 | 95 | (3) | 97 | | | | | | |
| 4 | 1.12 | 16 | 2.24 | | | | | | | 75 | | 70 | | | | 25 | | 7 | | | |
| 4 | 2.24 | 16 | 2.24 | | | | | | | 90 | | 73 | | | | 35 | | 30 | | | |
| 4 | 0.14 | 16 | 8.96 | 100 | | 98 | 100 | | 98 | 100 | | 95 | | | | | | | | | |
| 4 | 0.56 | 16 | 8.96 | 100 | (0) | 100 | 100 | (0) | 100 | 100 | (0) | 100 | | | | | | | | | |
| 4 | 0.56 | 16 | 8.96 | | | | | | | 95 | | 80 | 90 | (0) | 90 | | | | | | |
| 4 | 1.12 | 16 | 8.96 | | | | | | | 95 | | 70 | | | | 60 | | 7 | | | |
| 4 | 1.12 | 16 | 8.96 | | | | | | | 95 | | 80 | 95 | (3) | 97 | | | | | | |
| 4 | 2.24 | 16 | 8.96 | | | | | | | 95 | | 73 | | | | 20 | (34) | 30 | | | |
| 5 | 0.14 | 16 | 0.56 | | | | | | | 70 | | 35 | 0 | | | | | | | | |
| 5 | 0.14 | 16 | 0.56 | | | | 60 | | 32 | 60 | (0) | 60 | | | | | | | 100 | (0) | 100 |
| 5 | 0.14 | 16 | 0.56 | | | | | | | 90 | | 85 | | | | 40 | | 28 | | | |
| 5 | 0.56 | 16 | 0.56 | | | | 95 | (0) | 95 | 90 | (0) | 90 | | | | | | | 100 | (0) | 100 |
| 5 | 0.56 | 16 | 0.56 | | | | | | | 90 | (0) | 90 | | | | 35 | (30) | 50 | | | |
| 5 | 0.56 | 16 | 0.56 | | | | | | 1.5 | 70 | (13) | 80 | 40 | (47) | 75 | | | | | | |
| 5 | 0.14 | 16 | 2.24 | | | | | | | 85 | (0) | 85 | | | | 20 | (29) | 28 | | | |
| 5 | 0.14 | 16 | 2.24 | | | | 60 | | 32 | 85 | | 60 | | | | | | | 100 | (0) | 100 |
| 5 | 0.14 | 16 | 2.24 | | | | | | | 65 | | 35 | 0 | | | | | | | | |
| 5 | 0.56 | 16 | 2.24 | | | | | | | 90 | (0) | 90 | | | | 75 | | 50 | | | |
| 5 | 0.56 | 16 | 2.24 | | | | | | | 70 | (13) | 80 | 35 | (54) | 75 | | | | | | |
| 5 | 0.56 | 16 | 2.24 | | | | 95 | (0) | 95 | 95 | | 90 | | | | | | | 100 | (0) | 100 |
| 5 | 0.14 | 16 | 8.96 | | | | | | | 75 | | 35 | 0 | | | | | | | | |
| 5 | 0.14 | 16 | 8.96 | | | | 15 | (54) | 32 | 95 | | 60 | | | | | | | 95 | (5) | 100 |
| 5 | 0.14 | 16 | 8.96 | | | | | | | 95 | | 85 | | | | 20 | (29) | 28 | | | |
| 5 | 0.56 | 16 | 8.96 | | | | 90 | (6) | 95 | 95 | | 90 | | | | | | | 100 | (0) | 100 |
| 5 | 0.56 | 16 | 8.96 | | | | | | | 100 | | 90 | | | | 10 | | 50 | | | |

-continued

| | | | | | | | | | | | | | | | | | | | | | |
|---|---|---|---|---|---|---|---|---|---|---|---|---|---|---|---|---|---|---|---|---|---|
| 5 | 0.56 | 16 | 8.96 | | | | | | | 95 | | 80 | 40 | (47) | 75 | | | | | (80) | |
| 1 | 0.03 | 17 | 0.56 | 30 | (15) | 35 | 30 | (34) | 45 | 95 | | 65 | 5 | (80) | 25 | 10 | (60) | 25 | | | |
| 1 | 0.14 | 17 | 0.56 | 95 | (0) | 95 | 100 | | 97 | 100 | | 90 | 65 | (19) | 80 | 25 | (50) | 50 | | | |
| 1 | 0.03 | 17 | 2.24 | 10 | (72) | 35 | 10 | (78) | 45 | 95 | | 65 | 5 | (80) | 25 | 20 | (20) | 25 | | | |
| 1 | 0.14 | 17 | 2.24 | 25 | (74) | 95 | 100 | | 97 | 100 | | 90 | 65 | (19) | 80 | 50 | (0) | 50 | | | |
| 1 | 0.03 | 17 | 8.96 | 15 | (58) | 35 | 30 | (34) | 45 | 85 | | 65 | 10 | (60) | 25 | 15 | (40) | 25 | | | |
| 1 | 0.14 | 17 | 8.96 | 40 | (58) | 95 | 95 | (3) | 97 | 95 | | 90 | 20 | (75) | 80 | 20 | (60) | 50 | | | |
| 2 | 0.14 | 17 | 0.56 | 0 | (100) | 43 | 35 | (62) | 92 | 10 | (72) | 35 | | | | | | | | | |
| 2 | 0.14 | 17 | 0.56 | | | | | | | 15 | (75) | 60 | | | | | | | 30 | (22) | 38 |
| 2 | 0.28 | 17 | 0.56 | | | | | | | 100 | | 98 | 100 | | 82 | | | | | | |
| 2 | 0.28 | 17 | 0.56 | | | | | | | 75 | | 60 | 90 | (3) | 92 | | | | | | |
| 2 | 0.56 | 17 | 0.56 | | | | | | | 95 | | 85 | | | | | | | 80 | | 77 |
| 2 | 0.56 | 17 | 0.56 | 90 | (6) | 95 | 95 | (0) | 95 | 80 | (0) | 80 | | | | | | | | | |
| 2 | 1.12 | 17 | 0.56 | | | | | | | 100 | (0) | 100 | 100 | (0) | 100 | | | | | | |
| 2 | 1.12 | 17 | 0.56 | | | | | | | 65 | (8) | 70 | 100 | (0) | 100 | | | | | | |
| 2 | 0.14 | 17 | 2.24 | 5 | (89) | 43 | 85 | (8) | 92 | 35 | (0) | 35 | | | | | | | | | |
| 2 | 0.14 | 17 | 2.24 | | | | | | | 90 | | 60 | | | | | | | 30 | (22) | 38 |
| 2 | 0.28 | 17 | 2.24 | | | | | | | 90 | (9) | 98 | 100 | | 82 | | | | | | |
| 2 | 0.28 | 17 | 2.24 | | | | | | | 55 | (9) | 60 | 90 | (3) | 92 | | | | | | |
| 2 | 0.56 | 17 | 2.24 | | | | | | | 90 | | 85 | | | | | | | 70 | (10) | 77 |
| 2 | 0.56 | 17 | 2.24 | 95 | (0) | 95 | 95 | (0) | 95 | 75 | (7) | 80 | | | | | | | | | |
| 2 | 1.12 | 17 | 2.24 | | | | | | | 90 | (10) | 100 | 100 | (0) | 100 | | | | | | |
| 2 | 1.12 | 17 | 2.24 | | | | | | | 50 | (29) | 70 | 100 | (0) | 100 | | | | | | |
| 2 | 0.14 | 17 | 8.96 | | | | | | | 80 | | 60 | | | | | | | 35 | (8) | 38 |
| 2 | 0.14 | 17 | 8.96 | 0 | (100) | 43 | 85 | (8) | 92 | 55 | | 35 | | | | | | | | | |
| 2 | 0.28 | 17 | 8.96 | | | | | | | 95 | (4) | 98 | 95 | | 82 | | | | | | |
| 2 | 0.28 | 17 | 8.96 | | | | | | | 80 | | 60 | 70 | (24) | 92 | | | | | | |
| 2 | 0.56 | 17 | 8.96 | | | | | | | 55 | | 85 | | | | | | | 85 | | 77 |

-continued

| | | | | | | | | | | | | | | | | | | |
|---|---|---|---|---|---|---|---|---|---|---|---|---|---|---|---|---|---|---|
| 2 | 0.56 | 17 | 8.96 | 95 | (0) | 95 | 100 | | 95 | 90 | (36) | 80 | | | | | | |
| 2 | 1.12 | 17 | 8.96 | | | | | | | 95 | (5) | 100 | 100 | (0) | 100 | | | |
| 2 | 1.12 | 17 | 8.96 | | | | | | | 75 | | 70 | 95 | (5) | 100 | | | |
| 3 | 2.24 | 17 | 0.56 | | | | | | | 85 | | 55 | 10 | (0) | 10 | | | |
| 3 | 4.48 | 17 | 0.56 | | | | | | | 10 | (82) | 55 | 10 | (75) | 40 | | | |
| 3 | 2.24 | 17 | 2.24 | | | | | | | 10 | (82) | 55 | 5 | (50) | 10 | | | |
| 3 | 4.48 | 17 | 2.24 | | | | | | | 25 | (55) | 55 | 10 | (75) | 40 | | | |
| 3 | 2.24 | 17 | 8.96 | | | | | | | 30 | (46) | 55 | 0 | (100) | 10 | | | |
| 3 | 4.48 | 17 | 8.96 | | | | | | | 75 | | 55 | 10 | (75) | 40 | | | |
| 4 | 0.14 | 17 | 0.56 | 100 | | 98 | 95 | (4) | 98 | 100 | | 95 | | | | | | |
| 4 | 0.56 | 17 | 0.56 | 100 | (0) | 100 | 100 | (0) | 100 | 95 | (5) | 100 | | | | | | |
| 4 | 0.56 | 17 | 0.56 | | | | | | | 75 | (7) | 80 | 65 | (28) | 90 | | | |
| 4 | 1.12 | 17 | 0.56 | | | | | | | 60 | (25) | 80 | 60 | (39) | 97 | | | |
| 4 | 1.12 | 17 | 0.56 | | | | | | | 65 | (8) | 70 | | | | 25 | | 7 |
| 4 | 2.24 | 17 | 0.56 | | | | | | | 65 | (11) | 73 | | | | 45 | | 30 |
| 4 | 0.14 | 17 | 2.24 | 95 | (4) | 98 | 85 | (14) | 98 | 100 | | 95 | | | | | | |
| 4 | 0.56 | 17 | 2.24 | 100 | (0) | 100 | 100 | (0) | 100 | 100 | (0) | 100 | | | | | | |
| 4 | 0.56 | 17 | 2.24 | | | | | | | 70 | (13) | 80 | 0 | (100) | 90 | | | |
| 4 | 1.12 | 17 | 2.24 | | | | | | | 75 | (7) | 80 | 75 | (23) | 97 | | | |
| 4 | 1.12 | 17 | 2.24 | | | | | | | 75 | | 70 | | | | 0 | (100) | 7 |
| 4 | 2.24 | 17 | 2.24 | | | | | | | 60 | (18) | 73 | | | | 0 | (100) | 30 |
| 4 | 0.14 | 17 | 8.96 | 95 | (4) | 98 | 100 | | 98 | 100 | | 95 | | | | | | |
| 4 | 0.56 | 17 | 8.96 | 100 | (0) | 100 | 95 | (5) | 100 | 100 | (0) | 100 | | | | | | |
| 4 | 0.56 | 17 | 8.96 | | | | | | | 70 | (13) | 80 | 65 | (28) | 90 | | | |
| 4 | 1.12 | 17 | 8.96 | | | | | | | 85 | | 80 | 85 | (13) | 97 | | | |
| 4 | 1.12 | 17 | 8.96 | | | | | | | 60 | (15) | 70 | | | | 0 | (100) | 7 |
| 4 | 2.24 | 17 | 8.96 | | | | | | | 60 | | 73 | | | | 0 | | 30 |

-continued

| | | | | | | | | | | | | | | | | | | | | | | | | |
|---|---|---|---|---|---|---|---|---|---|---|---|---|---|---|---|---|---|---|---|---|---|---|---|---|
| 5 | 0.14 | 17 | 0.56 | | | | 20 | (38) | 32 | 70 | (18) | 60 | | | | | | | | (100) | | 100 | (0) | 100 |
| 5 | 0.14 | 17 | 0.56 | | | | | | | 50 | | 35 | 0 | | | | | | 45 | | 28 | | | |
| 5 | 0.14 | 17 | 0.56 | | | | | | | 55 | (36) | 85 | | | | | | | | | | | | |
| 5 | 0.56 | 17 | 0.56 | | | | | | | 90 | (0) | 90 | | | | | | | 20 | (60) | 50 | | | |
| 5 | 0.56 | 17 | 0.56 | | | | | | | 80 | (0) | 80 | 40 | (47) | 75 | | | | | | | | | |
| 5 | 0.56 | 17 | 0.56 | | | | 95 | (0) | 95 | 90 | (0) | 90 | | | | | | | | | | 100 | (0) | 100 |
| 5 | 0.14 | 17 | 2.24 | | | | 20 | (38) | 32 | 70 | | 60 | | | | | | | | | | 95 | (5) | 100 |
| 55 | 0.14 | 17 | 2.24 | | | | | | | 75 | (12) | 85 | | | | | | | 60 | | 28 | | | |
| 5 | 0.14 | 17 | 2.24 | | | | | | | 65 | | 35 | 0 | | | | | | 65 | | 50 | | | |
| 5 | 0.56 | 17 | 2.24 | | | | | | | 90 | (0) | 90 | | | | | | | | | | | | |
| 5 | 0.56 | 17 | 2.24 | | | | | | | 70 | (13) | 80 | 30 | (60) | 75 | | | | | | | | | |
| 5 | 0.56 | 17 | 2.24 | | | | 95 | (0) | 95 | 75 | (17) | 90 | | | | | | | | | | 100 | (0) | 100 |
| 5 | 0.14 | 17 | 8.96 | | | | 30 | (7) | 32 | 50 | (17) | 60 | | | | | | | | | | 95 | (5) | 100 |
| 5 | 0.14 | 17 | 8.96 | | | | | | | 85 | (0) | 85 | | | | | | | 60 | | 28 | | | |
| 5 | 0.14 | 17 | 8.96 | | | | | | | 65 | | 35 | 0 | | | | | | | | | | | |
| 5 | 0.56 | 17 | 8.96 | | | | 95 | (0) | 95 | 90 | (0) | 90 | | | | | | | | | | 100 | (0) | 100 |
| 5 | 0.56 | 17 | 8.96 | | | | | | | 90 | (0) | 90 | | | | | | | 55 | | 50 | | | |
| 5 | 0.56 | 17 | 8.96 | | | | | | | 70 | (13) | 80 | 0 | (100) | 75 | | | | | | | | | |
| 1 | 0.03 | 18 | 0.56 | 15 | (58) | 35 | 35 | (23) | 45 | 95 | | 65 | 15 | (40) | 25 | 10 | (60) | 25 | | | | | | |
| 1 | 0.14 | 18 | 0.56 | 70 | (27) | 95 | 95 | (3) | 97 | 95 | | 90 | 75 | (7) | 80 | 20 | (60) | 50 | | | | | | |
| 1 | 0.03 | 18 | 2.24 | 10 | (72) | 35 | 35 | (23) | 45 | 95 | | 65 | 10 | (60) | 25 | 15 | (40) | 25 | | | | | | |
| 1 | 0.14 | 18 | 2.24 | 50 | (48) | 95 | 65 | (33) | 97 | 100 | | 90 | 0 | (100) | 80 | 30 | (40) | 50 | | | | | | |
| 1 | 0.03 | 18 | 8.96 | 5 | (86) | 35 | 40 | (12) | 45 | 95 | | 65 | 0 | (100) | 25 | 15 | (40) | 25 | | | | | | |
| 1 | 0.14 | 18 | 8.96 | 65 | (32) | 95 | 95 | (3) | 97 | 100 | | 90 | 45 | (44) | 80 | 30 | (40) | 50 | | | | | | |
| 2 | 0.14 | 18 | 0.56 | | | | | | | 70 | | 60 | | | | | | | 85 | | 38 | | | |
| 2 | 0.14 | 18 | 0.56 | 10 | (77) | 43 | 90 | (3) | 92 | 30 | (15) | 35 | | | | | | | | | | | | |
| 2 | 0.28 | 18 | 0.56 | | | | | | | 100 | | 98 | 95 | | 82 | | | | | | | | | |
| 2 | 0.28 | 18 | 0.56 | | | | | | | 80 | | 60 | 85 | (8) | 92 | | | | | | | | | |
| 2 | 0.56 | 18 | 0.56 | | | | | | | 90 | | 85 | | | | | | | 95 | | 77 | | | |
| 2 | 0.56 | 18 | 0.56 | 95 | | 95 | 95 | | 95 | 85 | | 80 | | | | | | | | | | | | |

-continued

| | | | | | | | | | | | | | | | | | | |
|---|---|---|---|---|---|---|---|---|---|---|---|---|---|---|---|---|---|---|
| 2 | 1.12 | 18 | 0.56 | | (0) | | | (0) | | 95 | (5) | 100 | 100 | (0) | 100 | | | |
| 2 | 1.12 | 18 | 0.56 | | | | | | | 90 | | 70 | 95 | (5) | 100 | | | |
| 2 | 0.14 | 18 | 2.24 | 45 | | 43 | 90 | (3) | 92 | 85 | | 35 | | | | | | |
| 2 | 0.14 | 18 | 2.24 | | | | | | | 100 | | 60 | | | | 40 | | 38 |
| 2 | 0.28 | 18 | 2.24 | | | | | | | 100 | | 98 | 95 | | 82 | | | |
| 2 | 0.28 | 18 | 2.24 | | | | | | | 80 | | 60 | 90 | (3) | 92 | | | |
| 2 | 0.56 | 18 | 2.24 | 95 | (0) | 95 | 95 | (0) | 95 | 90 | | 80 | | | | | | |
| 2 | 0.56 | 18 | 2.24 | | | | | | | 90 | | 85 | | | | 90 | | 77 |
| 2 | 1.12 | 18 | 2.24 | | | | | | | 100 | (0) | 100 | 100 | (0) | 100 | | | |
| 2 | 1.12 | 18 | 2.24 | | | | | | | 65 | (8) | 70 | 95 | (5) | 100 | | | |
| 2 | 0.14 | 18 | 8.96 | 35 | (19) | 43 | 70 | (24) | 92 | 65 | | 35 | | | | | | |
| 2 | 0.14 | 18 | 8.96 | | | | | | | 90 | | 60 | | | | 80 | | 38 |
| 2 | 0.28 | 18 | 8.96 | | | | | | | 95 | (4) | 98 | 100 | | 82 | | | |
| 2 | 0.28 | 18 | 8.96 | | | | | | | 70 | | 60 | 95 | | 92 | | | |
| 2 | 0.56 | 18 | 8.96 | 95 | (0) | 95 | 95 | (0) | 95 | 90 | | 80 | | | | | | |
| 2 | 0.56 | 18 | 8.96 | | | | | | | 95 | | 85 | | | | 90 | | 77 |
| 2 | 1.12 | 18 | 8.96 | | | | | | | 95 | (5) | 100 | 100 | (0) | 100 | | | |
| 2 | 1.12 | 18 | 8.96 | | | | | | | 95 | | 70 | 90 | (10) | 100 | | | |
| 3 | 2.24 | 18 | 0.56 | | | | | | | 80 | | 55 | 15 | | 10 | | | |
| 3 | 4.48 | 18 | 0.56 | | | | | | | 55 | (0) | 55 | 15 | (63) | 40 | | | |
| 3 | 2.24 | 18 | 2.24 | | | | | | | 60 | | 55 | 5 | (50) | 10 | | | |
| 3 | 4.48 | 18 | 2.24 | | | | | | | 40 | (28) | 55 | 10 | (75) | 40 | | | |
| 3 | 2.24 | 18 | 8.96 | | | | | | | 50 | (10) | 55 | 5 | (50) | 10 | | | |
| 3 | 4.48 | 18 | 8.96 | | | | | | | 75 | | 55 | 15 | (63) | 40 | | | |
| 4 | 0.14 | 18 | 0.56 | 95 | (4) | 98 | 25 | (75) | 98 | 95 | (0) | 95 | | | | | | |
| 4 | 0.56 | 18 | 0.56 | 100 | (0) | 100 | 100 | (0) | 100 | 100 | (0) | 100 | | | | | | |
| 4 | 0.56 | 18 | 0.56 | | | | | | | 75 | (7) | 80 | 85 | (6) | 90 | | | |
| 4 | 1.12 | 18 | 0.56 | | | | | | | 90 | | 80 | 75 | (23) | 97 | | | |
| 4 | 1.12 | 18 | 0.56 | | | | | | | 70 | (0) | 70 | | | | 10 | | 7 |
| 4 | 2.24 | 18 | 0.56 | | | | | | | 65 | (11) | 73 | | | | 0 | (100) | 30 |

-continued

| | | | | | | | | | | | | | | | | | | | | | |
|---|---|---|---|---|---|---|---|---|---|---|---|---|---|---|---|---|---|---|---|---|---|
| 4 | 0.14 | 18 | 2.24 | 100 | | 98 | 95 | (4) | 98 | 95 | (0) | 95 | | | | | | | | | |
| 4 | 0.56 | 18 | 2.24 | 100 | (0) | 100 | 100 | (0) | 100 | 95 | (5) | 100 | | | | | | | | | |
| 4 | 0.56 | 18 | 2.24 | | | | | | | 70 | (13) | 80 | 45 | (50) | 90 | | | | | | |
| 4 | 1.12 | 18 | 2.24 | | | | | | | 80 | (0) | 80 | 55 | (44) | 97 | | | | | | |
| 4 | 1.12 | 18 | 2.24 | | | | | | | 80 | | 70 | | | | 0 | (100) | 7 | | | |
| 4 | 2.24 | 18 | 2.24 | | | | | | | 70 | (5) | 73 | | | | 35 | | 30 | | | |
| 4 | 0.14 | 18 | 8.96 | 95 | (4) | 98 | 95 | (4) | 98 | 90 | (6) | 95 | | | | | | | | | |
| 4 | 0.56 | 18 | 8.96 | | | | | | | 70 | (13) | 80 | 45 | (50) | 90 | | | | | | |
| 4 | 0.56 | 18 | 8.96 | 100 | (0) | 100 | 100 | (0) | 100 | 100 | (0) | 100 | | | | | | | | | |
| 4 | 1.12 | 18 | 8.96 | | | | | | | 95 | | 80 | 85 | (13) | 97 | | | | | | |
| 4 | 1.12 | 18 | 8.96 | | | | | | | 70 | (0) | 70 | | | | 15 | | 7 | | | |
| 4 | 2.24 | 18 | 8.96 | | | | | | | 70 | (5) | 73 | | | | 5 | (84) | 30 | | | |
| 5 | 0.14 | 18 | 0.56 | | | | | | | 80 | (6) | 85 | | | | 45 | | 28 | | | |
| 5 | 0.14 | 18 | 0.56 | | | | | | | 60 | | 35 | 0 | | | | | | | | |
| 5 | 0.14 | 18 | 0.56 | | | | 70 | | 32 | 90 | | 60 | | | | | | | 95 | (5) | 100 |
| 5 | 0.56 | 18 | 0.56 | | | | 95 | (0) | 95 | 95 | | 90 | | | | | | | 100 | (0) | 100 |
| 5 | 0.56 | 18 | 0.56 | | | | | | | 90 | (0) | 90 | | | | 80 | | 50 | | | |
| 5 | 0.56 | 18 | 0.56 | | | | | | | 65 | (19) | 80 | 55 | (27) | 75 | | | | | | |
| 5 | 0.14 | 18 | 2.24 | | | | | | | 95 | | 85 | | | | 45 | | 28 | | | |
| 5 | 0.14 | 18 | 2.24 | | | | | | | 65 | | 35 | 0 | | | | | | | | |
| 5 | 0.14 | 18 | 2.24 | | | | 55 | | 32 | 65 | | 60 | | | | | | | 100 | (0) | 100 |
| 5 | 0.56 | 18 | 2.24 | | | | | | | 70 | (13) | 80 | 10 | (87) | 75 | | | | | | |
| 5 | 0.56 | 18 | 2.24 | | | | | | | 90 | (0) | 90 | | | | 60 | | 50 | | | |
| 5 | 0.56 | 18 | 2.24 | | | | 95 | (0) | 95 | 95 | | 90 | | | | | | | 100 | (0) | 100 |
| 5 | 0.14 | 18 | 8.96 | | | | 50 | | 32 | 75 | | 60 | | | | | | | 100 | (0) | 100 |
| 5 | 0.14 | 18 | 8.96 | | | | | | | 90 | | 85 | | | | 20 | (29) | 28 | | | |
| 5 | 0.14 | 18 | 8.96 | | | | | | | 50 | | 35 | 0 | | | | | | | | |
| 5 | 0.56 | 18 | 8.96 | | | | | | | 90 | (0) | 90 | | | | 45 | (10) | 50 | | | |
| 5 | 0.56 | 18 | 8.96 | | | | | | | 75 | (7) | 80 | 20 | (74) | 75 | | | | | | |

-continued

| | | | | | | | | | | | | | | | | | | | | | | | | | | |
|---|---|---|---|---|---|---|---|---|---|---|---|---|---|---|---|---|---|---|---|---|---|---|---|---|---|---|
| 5 | 0.56 | 18 | 8.96 | | | | 90 | (6) | 95 | 95 | | 90 | | | | | | | | | 100 | (0) | 100 | | | |
| 1 | 0.03 | 19 | 0.56 | 25 | (29) | 35 | 15 | (67) | 45 | 95 | | 65 | 10 | (60) | 25 | 5 | (80) | 25 | | | | | | | | |
| 1 | 0.14 | 19 | 0.56 | | | | | | | | | | 70 | (13) | 80 | 50 | (0) | 50 | | | | | | | | |
| 1 | 0.14 | 19 | 0.56 | 25 | (74) | 95 | 85 | (13) | 97 | 100 | | 90 | 58 | (42) | 99 | | | | | | | | | 60 | | 55 |
| 1 | 0.56 | 19 | 0.56 | | | | | | | | | | 90 | (10) | 100 | | | | | | | | | 70 | (0) | 70 |
| 1 | 0.03 | 19 | 1.12 | 0 | | | 35 | | 25 | 60 | | 15 | | | | | | | | | | | | | | |
| 1 | 0.03 | 19 | 1.12 | | | | | | | 0 | | 5 | | | | | | | | | | | | | | |
| 1 | 0.14 | 19 | 1.12 | 20 | (66) | 58 | 40 | (52) | 83 | 50 | (0) | 50 | | | | | | | | | | | | | | |
| 1 | 0.14 | 19 | 1.12 | | | | | | | 35 | (54) | 75 | 5 | (93) | 68 | | | | | | | | | | | |
| 1 | 0.03 | 19 | 2.24 | 10 | (72) | 35 | 0 | (100) | 45 | 80 | | 65 | 5 | (80) | 25 | 5 | (80) | 25 | | | | | | | | |
| 1 | 0.14 | 19 | 2.24 | 90 | (6) | 95 | 100 | | 97 | 100 | | 90 | 70 | (13) | 80 | 30 | (40) | 50 | | | | | | | | |
| 1 | 0.14 | 19 | 2.24 | | | | | | | | | | 23 | (77) | 99 | | | | | | | | | 35 | (37) | 55 |
| 1 | 0.56 | 19 | 2.24 | | | | | | | | | | 85 | (15) | 100 | | | | | | | | | 70 | (0) | 70 |
| 1 | 0.03 | 19 | 4.48 | 5 | | | 0 | (100) | 25 | 60 | | 15 | | | | | | | | | | | | | | |
| 1 | 0.03 | 19 | 4.48 | | | | | | | 50 | | 0 | | | | | | | | | | | | | | |
| 1 | 0.14 | 19 | 4.48 | 0 | (100) | 58 | 85 | | 83 | 40 | (20) | 50 | | | | | | | | | | | | | | |
| 1 | 0.14 | 19 | 4.48 | | | | | | | 15 | (80) | 75 | 0 | (100) | 68 | | | | | | | | | | | |
| 1 | 0.03 | 19 | 8.96 | 15 | (58) | 35 | 0 | (100) | 45 | 80 | | 65 | 15 | (40) | 25 | 15 | (40) | 25 | | | | | | | | |
| 1 | 0.14 | 19 | 8.96 | 55 | (43) | 95 | 85 | (13) | 97 | 100 | | 90 | 12 | (88) | 99 | | | | | | | | | 50 | (10) | 55 |
| 1 | 0.14 | 19 | 8.96 | | | | | | | | | | 55 | (32) | 80 | 45 | (10) | 50 | | | | | | | | |
| 1 | 0.56 | 19 | 8.96 | | | | | | | | | | 95 | (5) | 100 | | | | | | | | | 70 | (0) | 70 |
| 2 | 0.14 | 19 | 0.56 | 30 | (31) | 43 | 65 | (30) | 92 | 75 | | 35 | | | | | | | | | | | | | | |
| 2 | 0.14 | 19 | 0.56 | | | | | | | 55 | (9) | 60 | | | | | | | 40 | 38 | | | | | | |
| 2 | 0.28 | 19 | 0.56 | | | | | | | 100 | | 98 | 95 | | 82 | | | | | | | | | | | |
| 2 | 0.28 | 19 | 0.56 | | | | | | | 50 | (17) | 60 | 70 | (24) | 92 | | | | | | | | | | | |
| 2 | 0.56 | 19 | 0.56 | | | | | | | 90 | | 85 | | | | | | | 95 | 77 | | | | | | |
| 2 | 0.56 | 19 | 0.56 | 95 | (0) | 95 | 95 | (0) | 95 | 75 | (7) | 80 | | | | | | | | | | | | | | |
| 2 | 1.12 | 19 | 0.56 | | | | | | | 100 | (0) | 100 | 100 | (0) | 100 | | | | | | | | | | | |
| 2 | 1.12 | 19 | 0.56 | | | | | | | 80 | | 70 | 100 | (0) | 100 | | | | | | | | | | | |
| 2 | 0.14 | 19 | 1.12 | 70 | | 23 | 90 | | 52 | 20 | | 48 | | | | | | | | | | | | | | |

-continued

| | | | | | | | | | | | | | | | | | | | | | |
|---|---|---|---|---|---|---|---|---|---|---|---|---|---|---|---|---|---|---|---|---|---|
| | | | | | | | | | | | (59) | | | | | | | | | | |
| 2 | 0.56 | 19 | 1.12 | 100 | | 95 | 95 | | 95 | 80 | | 95 | | | | | | | | | |
| | | | | | | | | (0) | | | (16) | | | | | | | | | | |
| 2 | 0.14 | 19 | 2.24 | | | | | | | 100 | | 60 | | | | 40 | | 38 | | | |
| 2 | 0.14 | 19 | 2.24 | 0 | | 43 | 25 | | 92 | 10 | | 35 | | | | | | | | | |
| | | | | | (100) | | | (73) | | | (72) | | | | | | | | | | |
| 2 | 0.28 | 19 | 2.24 | | | | | | | 95 | | 98 | 90 | | 82 | | | | | | |
| | | | | | | | | | | | (4) | | | | | | | | | | |
| 2 | 0.28 | 19 | 2.24 | | | | | | | 85 | | 60 | 90 | | 92 | | | | | | |
| | | | | | | | | | | | | | | (3) | | | | | | | |
| 2 | 0.56 | 19 | 2.24 | 95 | | 95 | 95 | | 95 | 90 | | 80 | | | | | | | | | |
| | | | | | (0) | | | (0) | | | | | | | | | | | | | |
| 2 | 0.56 | 19 | 2.24 | | | | | | | 80 | | 85 | | | | 85 | | 77 | | | |
| | | | | | | | | | | | (6) | | | | | | | | | | |
| 2 | 1.12 | 19 | 2.24 | | | | | | | 80 | | 70 | 100 | | 100 | | | | | | |
| | | | | | | | | | | | | | | (0) | | | | | | | |
| 2 | 1.12 | 19 | 2.24 | | | | | | | 95 | | 100 | 100 | | 100 | | | | | | |
| | | | | | | | | | | | (5) | | | (0) | | | | | | | |
| 2 | 0.14 | 19 | 4.48 | 80 | | 23 | 95 | | 52 | 75 | | 48 | | | | | | | | | |
| 2 | 0.56 | 19 | 4.48 | 95 | | 95 | 95 | | 95 | 85 | | 95 | | | | | | | | | |
| | | | | | (0) | | | (0) | | | (11) | | | | | | | | | | |
| 2 | 0.14 | 19 | 8.96 | 30 | | 43 | 50 | | 92 | 75 | | 35 | | | | | | | | | |
| | | | | | (31) | | | (46) | | | | | | | | | | | | | |
| 2 | 0.14 | 19 | 8.96 | | | | | | | 90 | | 60 | | | | 30 | | 38 | | | |
| | | | | | | | | | | | | | | | | | (22) | | | | |
| 2 | 0.28 | 19 | 8.96 | | | | | | | 95 | | 98 | 95 | | 82 | | | | | | |
| | | | | | | | | | | | (4) | | | | | | | | | | |
| 2 | 0.28 | 19 | 8.96 | | | | | | | 85 | | 60 | 95 | | 92 | | | | | | |
| 2 | 0.56 | 19 | 8.96 | 85 | | 95 | 95 | | 95 | 90 | | 80 | | | | | | | | | |
| | | | | | (11) | | | (0) | | | | | | | | | | | | | |
| 2 | 0.56 | 19 | 8.96 | | | | | | | 90 | | 85 | | | | 80 | | 77 | | | |
| 2 | 1.12 | 19 | 8.96 | | | | | | | 100 | | 100 | 100 | | 100 | | | | | | |
| | | | | | | | | | | | (0) | | | (0) | | | | | | | |
| 2 | 1.12 | 19 | 8.96 | | | | | | | 80 | | 70 | 100 | | 100 | | | | | | |
| | | | | | | | | | | | | | | (0) | | | | | | | |
| 3 | 2.24 | 19 | 0.56 | | | | | | | 15 | | 55 | 20 | | 10 | | | | | | |
| | | | | | | | | | | | (73) | | | | | | | | | | |
| 3 | 4.48 | 19 | 0.56 | | | | | | | 60 | | 55 | 15 | | 40 | | | | | | |
| | | | | | | | | | | | | | | (63) | | | | | | | |
| 3 | 2.24 | 19 | 2.24 | | | | | | | 75 | | 55 | 40 | | 10 | | | | | | |
| 3 | 4.48 | 19 | 2.24 | | | | | | | 70 | | 55 | 10 | | 40 | | | | | | |
| | | | | | | | | | | | | | | (75) | | | | | | | |
| 3 | 2.24 | 19 | 8.96 | | | | | | | 80 | | 55 | 20 | | 10 | | | | | | |
| 3 | 4.48 | 19 | 8.96 | | | | | | | 80 | | 55 | 15 | | 40 | | | | | | |
| | | | | | | | | | | | | | | (63) | | | | | | | |
| 4 | 0.14 | 19 | 0.56 | 90 | | 98 | 90 | | 98 | 90 | | 95 | 0 | | 8 | | | | 75 | | 70 |
| | | | | | (9) | | | (9) | | | (6) | | | (100) | | | | | | | |
| 4 | 0.56 | 19 | 0.56 | | | | | | | 70 | | 80 | 60 | | 90 | | | | | | |
| | | | | | | | | | | | (13) | | | (34) | | | | | | | |
| 4 | 0.56 | 19 | 0.56 | 95 | | 100 | 95 | | 100 | 100 | | 100 | 53 | | 97 | | | | 85 | | 85 |
| | | | | | (5) | | | (5) | | | (0) | | | (46) | | | | | | (0) | |
| 4 | 1.12 | 19 | 0.56 | | | | | | | 85 | | 80 | 85 | | 97 | | | | | | |
| | | | | | | | | | | | | | | (13) | | | | | | | |
| 4 | 1.12 | 19 | 0.56 | | | | | | | 80 | | 70 | | | | 0 | | 7 | | | |

-continued

| | | | | | | | | | | | | | | | | | | | | | | | | |
|---|---|---|---|---|---|---|---|---|---|---|---|---|---|---|---|---|---|---|---|---|---|---|---|---|
| | | | | | | | | | | | | | | | | | (100) | | | | | | | |
| 4 | 2.24 | 19 | 0.56 | | | | | | | 70 | (5) | 73 | | | | 20 | (34) | 30 | | | | | | |
| 4 | 0.14 | 19 | 1.12 | | | | | | | 75 | | 40 | 0 | (100) | 12 | | | | | | | | | |
| 4 | 0.56 | 19 | 1.12 | | | | | | | 60 | (8) | 65 | 10 | (82) | 53 | | | | | | | | | |
| 4 | 0.14 | 19 | 2.24 | 95 | (4) | 98 | 95 | (4) | 98 | 95 | (0) | 95 | 0 | (100) | 8 | | | | | | | 70 | (0) | 70 |
| 4 | 0.56 | 19 | 2.24 | 100 | (0) | 100 | 95 | (5) | 100 | 100 | (0) | 100 | 15 | (85) | 97 | | | | | | | 80 | (6) | 85 |
| 4 | 0.56 | 19 | 2.24 | | | | | | | 90 | | 80 | 65 | (28) | 90 | | | | | | | | | |
| 4 | 1.12 | 19 | 2.24 | | | | | | | 70 | (13) | 80 | 75 | (23) | 97 | | | | | | | | | |
| 4 | 1.12 | 19 | 2.24 | | | | | | | 90 | | 70 | | | | 5 | (29) | 7 | | | | | | |
| 4 | 2.24 | 19 | 2.24 | | | | | | | 65 | (11) | 73 | | | | 20 | (34) | 30 | | | | | | |
| 4 | 0.14 | 19 | 4.48 | | | | | | | 60 | | 40 | 0 | (100) | 12 | | | | | | | | | |
| 4 | 0.56 | 19 | 4.48 | | | | | | | 75 | | 65 | 20 | (63) | 53 | | | | | | | | | |
| 4 | 0.14 | 19 | 8.96 | 100 | | 98 | 90 | (9) | 98 | 100 | | 95 | 0 | (100) | 8 | | | | | | | 75 | | 70 |
| 4 | 0.56 | 19 | 8.96 | 100 | (0) | 100 | 100 | (0) | 100 | 100 | (0) | 100 | | | | | | | | | | | | |
| 4 | 0.56 | 19 | 8.96 | | | | | | | 70 | (13) | 80 | 30 | (67) | 90 | | | | | | | | | |
| 4 | 0.56 | 19 | 8.96 | | | | | | | | | | 28 | (72) | 97 | | | | | | | 85 | (0) | 85 |
| 4 | 1.12 | 19 | 8.96 | | | | | | | 95 | | 80 | 90 | (8) | 97 | | | | | | | | | |
| 4 | 1.12 | 19 | 8.96 | | | | | | | 75 | | 70 | | | | 20 | | 7 | | | | | | |
| 4 | 2.24 | 19 | 8.96 | | | | | | | 65 | (11) | 73 | | | | 20 | (34) | 30 | | | | | | |
| 5 | 0.14 | 19 | 0.56 | | | | | | | 75 | | 35 | 0 | | | | | | | | | | | |
| 5 | 0.14 | 19 | 0.56 | | | | 10 | (69) | 32 | 60 | (0) | 60 | | | | | | | 95 | (5) | 100 | | | |
| 5 | 0.14 | 19 | 0.56 | | | | | | | 90 | | 85 | | | | 45 | | 28 | | | | | | |
| 5 | 0.56 | 19 | 0.56 | | | | | | | 90 | (0) | 90 | | | | 80 | | 50 | | | | | | |
| 5 | 0.56 | 19 | 0.56 | | | | 95 | (0) | 95 | 95 | | 90 | | | | | | | 100 | (0) | 100 | | | |
| 5 | 0.56 | 19 | 0.56 | | | | | | | 70 | (13) | 80 | 10 | (87) | 75 | | | | | | | | | |
| 5 | 0.14 | 19 | 2.24 | | | | | | | 65 | | 35 | 0 | | | | | | | | | | | |
| 5 | 0.14 | 19 | 2.24 | | | | | | | 95 | | 85 | | | | 5 | (83) | 28 | | | | | | |
| 5 | 0.14 | 19 | 2.24 | | | | 40 | | 32 | 60 | (0) | 60 | | | | | | | 100 | (0) | 100 | | | |
| 5 | 0.56 | 19 | 2.24 | | | | 95 | (0) | 95 | 75 | (17) | 90 | | | | | | | 100 | (0) | 100 | | | |
| 5 | 0.56 | 19 | 2.24 | | | | | | | 80 | | 80 | 15 | | 75 | | | | | | | | | |

-continued

| | | | | | | | | | | | | | | | | | | | | | | | | |
|---|---|---|---|---|---|---|---|---|---|---|---|---|---|---|---|---|---|---|---|---|---|---|---|---|
| | | | | | | | | | | | (0) | | | (80) | | | | | | | | | | |
| 5 | 0.56 | 19 | 2.24 | | | | | | | 90 | (0) | 90 | | | | 30 | (40) | 50 | | | | | | |
| 5 | 0.14 | 19 | 8.96 | | | | | | | 65 | | 35 | 0 | | | 80 | | 28 | | | | | | |
| 5 | 0.14 | 19 | 8.96 | | | | | | | 90 | | 85 | | | | | | | 85 | (15) | 100 | | | |
| 5 | 0.14 | 19 | 8.96 | | | | 0 | (100) | 32 | 50 | (17) | 60 | | | | | | | | | | | | |
| 5 | 0.56 | 19 | 8.96 | | | | 30 | (69) | 95 | 90 | (0) | 90 | | | | | | | 100 | (0) | 100 | | | |
| 5 | 0.56 | 19 | 8.96 | | | | | | | 65 | (19) | 80 | 25 | (67) | 75 | | | | | | | | | |
| 5 | 0.56 | 19 | 8.96 | | | | | | | 95 | | 90 | | | | 90 | | 50 | | | | | | |
| 1 | 0.14 | 20 | 0.56 | | | | | | | | | | 85 | (15) | 99 | | | | | | | 55 | (0) | 55 |
| 1 | 0.56 | 20 | 0.56 | | | | | | | | | | 99 | (1) | 100 | | | | | | | 65 | (8) | 70 |
| 1 | 0.03 | 20 | 1.12 | | | | | | | 20 | | 0 | | | | | | | | | | | | |
| 1 | 0.03 | 20 | 1.12 | 0 | | | 10 | (60) | 25 | 50 | | 15 | | | | | | | | | | | | |
| 1 | 0.14 | 20 | 1.12 | 15 | (75) | 58 | 85 | | 83 | 45 | (10) | 50 | | | | | | | | | | | | |
| 1 | 0.14 | 20 | 1.12 | | | | | | | 0 | (100) | 75 | 15 | (78) | 68 | | | | | | | | | |
| 1 | 0.14 | 20 | 2.24 | | | | | | | | | | 75 | (25) | 99 | | | | | | | 60 | | 55 |
| 1 | 0.56 | 20 | 2.24 | | | | | | | | | | 95 | (5) | 100 | | | | | | | 80 | | 70 |
| 1 | 0.03 | 20 | 4.48 | | | | | | | 0 | | | 0 | | | | | | | | | | | |
| 1 | 0.03 | 20 | 4.48 | 15 | | | 45 | | 25 | 60 | | 15 | | | | | | | | | | | | |
| 1 | 0.14 | 20 | 4.48 | 5 | (92) | 58 | 65 | (22) | 83 | 30 | (40) | 50 | | | | | | | | | | | | |
| 1 | 0.14 | 20 | 4.48 | | | | | | | 35 | (54) | 75 | 20 | (71) | 68 | | | | | | | | | |
| 1 | 0.14 | 20 | 8.96 | | | | | | | | | | 85 | (15) | 99 | | | | | | | 70 | | 55 |
| 1 | 0.56 | 20 | 8.96 | | | | | | | | | | 95 | (5) | 100 | | | | | | | 75 | | 70 |
| 2 | 0.14 | 20 | 0.56 | 45 | | 43 | 35 | (62) | 92 | 20 | (43) | 35 | | | | | | | | | | | | |
| 2 | 0.14 | 20 | 0.56 | | | | | | | 0 | (100) | 60 | | | | 15 | (61) | 38 | | | | | | |
| 2 | 0.28 | 20 | 0.56 | | | | | | | 100 | | 98 | 75 | (9) | 82 | | | | | | | | | |
| 2 | 0.28 | 20 | 0.56 | | | | | | | 70 | (3) | 60 | 90 | | 92 | | | | | | | | | |
| 2 | 0.56 | 20 | 0.56 | 95 | (0) | 95 | 95 | (0) | 95 | 85 | | 80 | | | | | | | | | | | | |
| 2 | 0.56 | 20 | 0.56 | | | | | | | 65 | (24) | 85 | | | | 90 | | 77 | | | | | | |
| 2 | 1.12 | 20 | 0.56 | | | | | | | 100 | (0) | 100 | 100 | (0) | 100 | | | | | | | | | |
| 2 | 1.12 | 20 | 0.56 | | | | | | | 75 | | 70 | 100 | (0) | 100 | | | | | | | | | |
| 2 | 0.14 | 20 | 1.12 | 35 | | 23 | 55 | | 52 | 0 | | 48 | | | | | | | | | | | | |

-continued

| | | | | | | | | | | | | | | | | | | | | |
|---|---|---|---|---|---|---|---|---|---|---|---|---|---|---|---|---|---|---|---|---|
| 2 | 0.56 | 20 | 1.12 | 80 | (16) | 95 | 95 | (0) | 95 | 90 | (100) | 95 | | | | | | | | |
| 2 | 0.14 | 20 | 2.24 | | | | | | | 55 | (6) | 60 | | | | 80 | 38 | | | |
| 2 | 0.14 | 20 | 2.24 | 10 | (77) | 43 | 65 | (30) | 92 | 10 | (9) | 35 | | | | | | | | |
| 2 | 0.28 | 20 | 2.24 | | | | | | | 95 | (72) | 98 | 95 | | 82 | | | | | |
| 2 | 0.28 | 20 | 2.24 | | | | | | | 85 | (4) | 60 | 70 | (24) | 92 | | | | | |
| 2 | 0.56 | 20 | 2.24 | 95 | (0) | 95 | 95 | (0) | 95 | 90 | | 80 | | | | | | | | |
| 2 | 0.56 | 20 | 2.24 | | | | | | | 95 | | 85 | | | | 80 | 77 | | | |
| 2 | 1.12 | 20 | 2.24 | | | | | | | 100 | (0) | 100 | 100 | (0) | 100 | | | | | |
| 2 | 1.12 | 20 | 2.24 | | | | | | | 100 | | 70 | 100 | (0) | 100 | | | | | |
| 2 | 0.14 | 20 | 4.48 | 5 | (79) | 23 | 80 | | 52 | 75 | | 48 | | | | | | | | |
| 2 | 0.56 | 20 | 4.48 | 95 | (0) | 95 | 95 | (0) | 95 | 95 | (0) | 95 | | | | | | | | |
| 2 | 0.14 | 20 | 8.96 | | | | | | | 95 | | 60 | | | | 70 | 38 | | | |
| 2 | 0.14 | 20 | 8.96 | 10 | (77) | 43 | 25 | (73) | 92 | 95 | | 35 | | | | | | | | |
| 2 | 0.28 | 20 | 8.96 | | | | | | | 100 | | 98 | 90 | | 82 | | | | | |
| 2 | 0.28 | 20 | 8.96 | | | | | | | 80 | | 60 | 95 | | 92 | | | | | |
| 2 | 0.56 | 20 | 8.96 | | | | | | | 95 | | 85 | | | | 85 | 77 | | | |
| 2 | 0.56 | 20 | 8.96 | 95 | (0) | 95 | 95 | (0) | 95 | 85 | | 80 | | | | | | | | |
| 2 | 1.12 | 20 | 8.96 | | | | | | | 100 | (0) | 100 | 100 | (0) | 100 | | | | | |
| 2 | 1.12 | 20 | 8.96 | | | | | | | 70 | (0) | 70 | 100 | (0) | 100 | | | | | |
| 3 | 2.24 | 20 | 0.56 | | | | | | | 15 | (73) | 55 | 0 | (100) | 10 | | | | | |
| 3 | 4.48 | 20 | 0.56 | | | | | | | 25 | (55) | 55 | 10 | (75) | 40 | | | | | |
| 3 | 2.24 | 20 | 2.24 | | | | | | | 0 | (100) | 55 | 10 | (0) | 10 | | | | | |
| 3 | 4.48 | 20 | 2.24 | | | | | | | 85 | | 55 | 5 | (88) | 40 | | | | | |
| 3 | 2.24 | 20 | 8.96 | | | | | | | 90 | | 55 | 10 | (0) | 10 | | | | | |
| 3 | 4.48 | 20 | 8.96 | | | | | | | 50 | (10) | 55 | 20 | (50) | 40 | | | | | |
| 4 | 0.14 | 20 | 0.56 | 95 | (4) | 98 | 85 | (14) | 98 | 100 | | 95 | 0 | (100) | 8 | | | 70 | (0) | 70 |
| 4 | 0.56 | 20 | 0.56 | 100 | (0) | 100 | 95 | (5) | 100 | 80 | (20) | 100 | | | | | | | | |
| 4 | 0.56 | 20 | 0.56 | | | | | | | 75 | (7) | 80 | 15 | (84) | 90 | | | | | |
| 4 | 0.56 | 20 | 0.56 | | | | | | | | | | 75 | (23) | 97 | | | 80 | (6) | 85 |

-continued

| | | | | | | | | | | | | | | | | | | | | | | | | |
|---|---|---|---|---|---|---|---|---|---|---|---|---|---|---|---|---|---|---|---|---|---|---|---|---|
| 4 | 1.12 | 20 | 0.56 | | | | | | | 70 | (13) | 80 | 80 | (18) | 97 | | | | | | | | | |
| 4 | 1.12 | 20 | 0.56 | | | | | | | 65 | (8) | 70 | | | | 20 | | 7 | | | | | | |
| 4 | 2.24 | 20 | 0.56 | | | | | | | 70 | (5) | 73 | | | | 5 | (84) | 30 | | | | | | |
| 4 | 0.14 | 20 | 1.12 | | | | | | | 0 | (100) | 40 | 5 | (59) | 12 | | | | | | | | | |
| 4 | 0.56 | 20 | 1.12 | | | | | | | 65 | (0) | 65 | 5 | (91) | 53 | | | | | | | | | |
| 4 | 0.14 | 20 | 2.24 | 95 | (4) | 98 | 80 | (19) | 98 | 100 | | 95 | 0 | (100) | 8 | 85 | | 70 | | | | | | |
| 4 | 0.56 | 20 | 2.24 | 100 | (0) | 100 | 100 | (0) | 100 | 95 | (5) | 100 | | | | | | | | | | | | |
| 4 | 0.56 | 20 | 2.24 | | | | | | | 85 | | 80 | 25 | (73) | 90 | | | | | | | | | |
| 4 | 0.56 | 20 | 2.24 | | | | | | | | | | 85 | (13) | 97 | | | | | | | 85 | (0) | 85 |
| 4 | 1.12 | 20 | 2.24 | | | | | | | 90 | | 80 | 85 | (13) | 97 | | | | | | | | | |
| 4 | 1.12 | 20 | 2.24 | | | | | | | 70 | (0) | 70 | | | | 0 | (100) | 7 | | | | | | |
| 4 | 2.24 | 20 | 2.24 | | | | | | | 75 | | 73 | | | | 20 | (34) | 30 | | | | | | |
| 4 | 0.14 | 20 | 4.48 | | | | | | | 25 | (38) | 40 | 0 | (100) | 12 | | | | | | | | | |
| 4 | 0.56 | 20 | 4.48 | | | | | | | 80 | | 65 | 40 | (25) | 53 | | | | | | | | | |
| 4 | 0.14 | 20 | 8.96 | 95 | (4) | 98 | 95 | (4) | 98 | 95 | (0) | 95 | 0 | (100) | 8 | | | | | | | 60 | (15) | 70 |
| 4 | 0.56 | 20 | 8.96 | 95 | (5) | 100 | 100 | (0) | 100 | 100 | (0) | 100 | | | | | | | | | | | | |
| 4 | 0.56 | 20 | 8.96 | | | | | | | 90 | | 80 | 35 | (62) | 90 | | | | | | | | | |
| 4 | 0.56 | 20 | 8.96 | | | | | | | | | | 12 | (88) | 97 | | | | | | | 80 | (6) | 85 |
| 4 | 1.12 | 20 | 8.96 | | | | | | | 90 | | 80 | 60 | (39) | 97 | | | | | | | | | |
| 4 | 1.12 | 20 | 8.96 | | | | | | | 65 | (8) | 70 | | | | 0 | (100) | 7 | | | | | | |
| 4 | 2.24 | 20 | 8.96 | | | | | | | 65 | (11) | 73 | | | | 20 | (34) | 30 | | | | | | |
| 5 | 0.14 | 20 | 0.56 | | | | | | | 60 | | 35 | 0 | | | | | | | | | | | |
| 5 | 0.14 | 20 | 0.56 | | | | 30 | (7) | 32 | 85 | | 60 | | | | | | | 100 | (0) | 100 | | | |
| 5 | 0.14 | 20 | 0.56 | | | | | | | 75 | (12) | 85 | | | | 80 | | 28 | | | | | | |
| 5 | 0.56 | 20 | 0.56 | | | | | | | 70 | (13) | 80 | 30 | (60) | 75 | | | | | | | | | |
| 5 | 0.56 | 20 | 0.56 | | | | | | | 85 | (6) | 90 | | | | 50 | (0) | 50 | | | | | | |
| 5 | 0.56 | 20 | 0.56 | | | | 95 | (0) | 95 | 95 | | 90 | | | | | | | 100 | (0) | 100 | | | |
| 5 | 0.14 | 20 | 2.24 | | | | | | | 55 | | 35 | 0 | | | | | | | | | | | |

-continued

| | | | | | | | | | | | | | | | | | | | | | |
|---|---|---|---|---|---|---|---|---|---|---|---|---|---|---|---|---|---|---|---|---|---|
| 5 | 0.14 | 20 | 2.24 | 90 | | 85 | | | | | | | 40 | | 28 | | | | | | |
| 5 | 0.14 | 20 | 2.24 | | | | 30 | (7) | 32 | 25 | (59) | 60 | | | | | | | 95 | (5) | 100 |
| 5 | 0.56 | 20 | 2.24 | | | | | | | 70 | (13) | 80 | 5 | (94) | 75 | | | | | | |
| 5 | 0.56 | 20 | 2.24 | 95 | (0) | 95 | 90 | (0) | 90 | | | | | | | 100 | (0) | 100 | | | |
| 5 | 0.56 | 20 | 2.24 | | | | | | | 90 | (0) | 90 | | | | 35 | (30) | 50 | | | |
| 5 | 0.14 | 20 | 8.96 | | | | 30 | (7) | 32 | 25 | (59) | 60 | | | | | | | 80 | (20) | 100 |
| 5 | 0.14 | 20 | 8.96 | | | | | | | 95 | | 85 | | | | 30 | | 28 | | | |
| 5 | 0.14 | 20 | 8.96 | | | | | | | 65 | | 35 | 0 | | | | | | | | |
| 5 | 0.56 | 20 | 8.96 | | | | | | | 90 | (0) | 90 | | | | 30 | (40) | 50 | | | |
| 5 | 0.56 | 20 | 8.96 | | | | | | | 75 | (7) | 80 | 10 | (87) | 75 | | | | | | |
| 5 | 0.56 | 20 | 8.96 | | | | 90 | (6) | 95 | 95 | | 90 | | | | | | | 100 (0) | | 100 |

EXAMPLE 7

The following procedure shows interaction between herbicide and antidote when applied together as a mixture before emergence of the crop and weed species, simulating a "tank-mixture" application. Containers were filled and compacted with fumigated silt loam top soil to a depth of about 1.3 cm from the top of the container. A first container was designated as an untreated control, a second container was designated as a herbicide control, and a third container was designated as a herbicide+antidote test container. Each of the containers was seeded with both crop plant and weed species. The herbicide (imazaquin) and the herbicide+antidote test mixture were applied to the seeded containers either by a procedure of topical application to a soil layer placed over the seed bed followed by watering to achieve incorporation, or by a procedure of incorporation into soil and then placement of the treated soil into the container over the seed bed. The containers were then placed on a greenhouse bench, and sub-irrigated as required for the duration of the test. Plant response was observed about three weeks after initial treatment. Results are reported in Table 3.

TABLE 3

| Herb No. 1 Kg/Ha | Antidote No. 0.56 Kg/Ha | % Plant Inhibition / % Inhibition Corn | Sorghum | Wheat | Rice | Soybeans |
|---|---|---|---|---|---|---|
| 0 | 0 | 0 | 0 | 0 | 0 | 0 |
| 0.28 | 0 | 10 | 15 | 10 | 30 | 0 |
| 0.56 | 0 | 15 | 35 | 35 | 55 | 10 |
| 1.12 | 0 | 50 | 50 | 45 | 70 | 15 |
| 0.28 | 2 | 15 | 20 | 15 | 45 | 0 |
| 0.56 | 2 | 20 | 25 | 10 | 60 | 0 |
| 1.12 | 2 | 25 | 25 | 15 | 55 | 10 |
| 0.28 | 8 | 10 | 20 | 10 | 20 | 0 |
| 0.56 | 8 | 20 | 15 | 20 | 45 | 0 |
| 1.12 | 8 | 35 | 25 | 15 | 55 | 10 |
| 0.28 | 9 | 15 | 25 | 15 | 15 | 0 |
| 0.56 | 9 | 15 | 35 | 40 | 70 | 0 |
| 1.12 | 9 | 25 | 30 | 30 | 55 | 0 |
| 0.28 | 14 | 5 | 10 | 0 | 10 | 0 |
| 0.56 | 14 | 25 | 25 | 20 | 55 | 0 |
| 1.12 | 14 | 45 | 35 | 25 | 55 | 10 |
| 0.28 | 16 | 5 | 20 | 5 | 30 | 0 |
| 0.56 | 16 | 15 | 20 | 20 | 45 | 0 |
| 1.12 | 16 | 30 | 35 | 35 | 65 | 10 |
| 0.28 | 17 | 5 | 15 | 10 | 15 | 0 |
| 0.56 | 17 | 10 | 15 | 10 | 45 | 0 |
| 1.12 | 17 | 20 | 30 | 35 | 60 | 10 |
| 0.28 | 4 | 10 | 20 | 15 | 15 | 0 |
| 0.56 | 4 | 25 | 20 | 30 | 45 | 0 |
| 1.12 | 4 | 30 | 35 | 30 | 70 | 20 |
| 0.28 | 3 | 10 | 25 | 25 | 20 | 0 |
| 0.56 | 3 | 20 | 15 | 35 | 45 | 5 |
| 1.12 | 3 | 40 | 40 | 40 | 70 | 15 |

Summarizing the data in Table 3 it is shown that corn, wheat, rice and sorghum were significantly safened against the herbicidal activity of imazaquin (Herbicide No. 1) by one or more of the antidotes in the test. Soybeans were not significantly injured by the herbicide, hence Preventing evaluation of the antidotes. Imazaquin injury on corn at 1.12 kg/ha was reduced from an average of 50% to an average of 26% for Antidote Nos. 2, 4, 9 and 16. Sorghum injury by imazaquin was reduced from 50% to an average of 28% at 0.56 kg/ha by Antidotes Nos. 2, 8, 9, 77 and 17. Wheat injury by the herbicide was reduced from an average of 45% to 18% at 0.56 kg/ha by Antidotes Nos. 2, 8 and 14. And rice injury was reduced from an average of 55% to an average of 35% when Antidote No. 77 (0.56kg/ha) was mixed with 0.56 kg/ha of the herbicide.

Overall, corn and sorghum, were more susceptible to safening against the herbicide than rice and wheat.

EXAMPLE 8

The following procedure was used to determine the interaction between a herbicide (imazaquin) and various antidotes when the herbicide is topically applied to crop seed. Crop plant seed may be treated with the antidote either by contacting the seed with antidote in powder form or by contacting the seed with solution or suspension of antidote compound dissolved or suspended in a suitable solvent, typically methylene chloride or toluene. Relative amounts of antidote compound and seed are used to provide an antidote-on-seed concentration, on a percent weight/weight basis, typically within the range of about 0.03 to 0.13%. Containers were filled and compacted with fumigated silt loam type soil to a depth of about 1.3 cm from the top of the container. A first container was designated as an untreated control, a second container was designated as a herbicide control, and a third container was designated as a herbicide+antidote test container. Untreated crop seed was placed in the first and second containers. Antidote-treated crop seed was placed in the third container. Then, each of the second and third containers was filled and leveled with a cover layer of soil having incorporated therein the selected herbicide at a pre-determined concentration. The first container was filled and leveled with soil containing no herbicide. All containers were given about 0.6 cm of overhead water to simulate an activating rainfall. The containers were placed on a greenhouse bench and sub-irrigated as required for the duration of the test. Plant response was observed about three weeks after initial treatment.

In Table 4, the herbicide was applied in the preplanted soil-incorporated mode with the antidote-coated seed as described above and in Table 4A, the herbicide was applied in a postemergence mode when the corn was in the 2-leaf stage (7–8 cm) and the sorghum was in the 3-leaf stage (6–8 cm).

In this example, the antidotes were coated onto Pioneer corn seed and DeKalb sorghum seed for testing with imazaquin herbicide. Test results are shown in Tables 4 and 4A. The percent injury values shown for the herbicide treatment only (no antidote) are averages of six replications.

TABLE 4

SEED TREATMENT - PREPLANT INCORPORATION

| Herb No. 1 Kg/Ha | Antidote No. 0.125% w/w | % Inhibition Pioneer Corn | DeKalb Sorghum |
|---|---|---|---|
| 0 | 0 | 0 | 0 |
| 0.56 | 0 | 70 | 60 |
| 1.12 | 0 | 80 | 75 |
| 2.24 | 0 | 95 | 85 |
| 0 | 3 | 0 | 0 |
| 0.56 | 3 | 65 | 50 |
| 1.12 | 3 | 75 | 60 |
| 2.24 | 3 | 90 | 75 |
| 0 | 7 | 0 | 0 |
| 0.56 | 7 | 55 | 55 |
| 1.12 | 7 | 65 | 50 |
| 2.24 | 7 | 85 | 80 |
| 0 | 13 | 0 | 0 |
| 0.56 | 13 | 60 | 50 |
| 1.12 | 13 | 65 | 50 |
| 2.24 | 13 | 90 | 80 |
| 0 | 2 | 0 | 0 |

TABLE 4-continued

| SEED TREATMENT - PREPLANT INCORPORATION | | | |
|---|---|---|---|
| Herb No. 1 Kg/Ha | Antidote No. 0.125% w/w | % Inhibition Pioneer Corn | % Inhibition DeKalb Sorghum |
| 0.56 | 2 | 65 | 55 |
| 1.12 | 2 | 75 | 65 |
| 2.24 | 2 | 95 | 85 |
| 0 | 14 | 0 | 0 |
| 0.56 | 14 | 55 | 60 |
| 1.12 | 14 | 75 | 70 |
| 2.24 | 14 | 80 | 80 |
| 0 | 16 | 0 | 0 |
| 0.56 | 16 | 80 | 60 |
| 1.12 | 16 | 90 | 75 |
| 2.24 | 16 | 90 | 65 |
| 0 | 77 | 0 | 0 |
| 0.56 | 77 | 65 | 60 |
| 1.12 | 77 | 75 | 60 |
| 2.24 | 77 | 95 | 70 |

TABLE 4A

| SEED TREATMENT - POSTEMERGENCE TREATMENT | | | |
|---|---|---|---|
| Herb No. 1 Kg/Ha | Antidote No. 0.125% w/w | % Inhibition Pioneer Corn | % Inhibition DeKalb Sorghum |
| 0 | 0 | 0 | 0 |
| 0.56 | 0 | 90 | 75 |
| 1.12 | 0 | 95 | 80 |
| 2.24 | 0 | 90 | 90 |
| 0 | 3 | 0 | 0 |
| 0.56 | 3 | 85 | 60 |
| 1.12 | 3 | 95 | 65 |
| 2.24 | 3 | 98 | 70 |
| 0 | 7 | 0 | 0 |
| 0.56 | 7 | 80 | 55 |
| 1.12 | 7 | 95 | 60 |
| 2.24 | 7 | 98 | 80 |
| 0 | 13 | 0 | 0 |
| 0.56 | 13 | 85 | 55 |
| 1.12 | 13 | 95 | 65 |
| 2.24 | 13 | 98 | 70 |
| 0 | 2 | 0 | 0 |
| 0.56 | 2 | 85 | 60 |
| 1.12 | 2 | 90 | 65 |
| 2.24 | 2 | 98 | 75 |
| 0 | 14 | 0 | 0 |
| 0.56 | 14 | 80 | 60 |
| 1.12 | 14 | 90 | 65 |
| 2.24 | 14 | 98 | 80 |
| 0 | 16 | 0 | 0 |
| 0.56 | 16 | 75 | 55 |
| 1.12 | 16 | 90 | 60 |
| 2.24 | 16 | 98 | 80 |
| 0 | 77 | 0 | 0 |
| 0.56 | 77 | 85 | 65 |
| 1.12 | 77 | 90 | 75 |
| 2.24 | 77 | 95 | 80 |

Referring to the data in Tables 4 and 4A, it appears that corn was not significantly safened in this test. However, some sorghum safening was observed with both preplant incorporated (PPI) and postemergence applications of the herbicide on treated seed. Although replicates were somewhat erratic, when averaged, Antidote No. 3, 7, 13, 14 and 16 demonstrated significant safening against imazaquin applied PPI and/or postemergence.

Sorghum injury levels were reduced from a range of 75%-85% to a range of 50%-65% for imazaquin at 1.12 kg/ha applied PPI or postemergence.

EXAMPLE9

This example follows the procedure described in Example 6, but uses certain modifications thereof. These procedures are designed to test the interaction between herbicide and antidote when both are incorporated in a soil cover layer before emergence of crop and weed species. The imidazolinone herbicide in this example was No. 4 (imazethapyr) mixed with acetochlor as a co-herbicide. The numbered antidotes are identified above.

Containers were filled and compacted with a fumigated silt loam top soil to a depth of about 1.3 cm from the top of the container. A first container was designated as an untreated control, a second container was designated as a herbicide control, and a third container was designated as a herbicide+antidote test container. Each of the containers was seeded with a crop species. A measured amount of each herbicide dispersed or dissolved in acetone or water was applied to a measured quantity of soil. To this same quantity of soil treated with herbicide, there was added a measured amount of antidote dispersed or dissolved in acetone or water. The quantity of soil treated with the herbicide and antidote was thoroughly mixed to incorporate the herbicide and antidote in the soil uniformly. The seed bed in the third container of soil was covered with the soil treated with the herbicide and antidote and the container was leveled. For each test series, the seed beds of the first and second containers were likewise covered by soil layers. The cover layer of the first container was not treated with herbicide or antidote. The cover layer of the second container had a measured quantity of both herbicides alone incorporated therein. Each container received 0.6 cm overhead irrigation. The containers were then placed on a bench in a greenhouse and sub-irrigated as required for the duration of the test. Plant response was observed about three weeks after initial treatment. Results are reported in Table 5, wherein the weeds in the test, redroot pigweed and barnyardgrass have the symbols "RRP" and "BYG", respectively. The first three treatments (without the antidote are the average of three replications and all others one replication.

TABLE 5

| Herbicide Acetochlor Rate | Herbicide No. 4 (Kg/Ha) | Antidote No. | Antidote Kg/Ha | % Injury Corn | % Injury RRP | % Injury BYG |
|---|---|---|---|---|---|---|
| 4.48 | — | 1 | — | 45 | 100 | 100 |
| — | 0.56 | 1 | — | 85 | 100 | 80 |
| 4.48 | 0.56 | 1 | — | 100 | 100 | 100 |
| — | — | 1 | 8.96 | 0 | 0 | 0 |
| 4.48 | — | 1 | 2.24 | 0 | 0 | 0 |
| 4.48 | — | 1 | 8.96 | 20 | 100 | 100 |
| — | 0.56 | 1 | 2.24 | 15 | 0 | 90 |
| — | 0.56 | 1 | 8.96 | 20 | 90 | 95 |
| 4.48 | 0.56 | 1 | 2.24 | 40 | 100 | 100 |
| 4.48 | 0.56 | 1 | 8.96 | 15 | 100 | 100 |
| — | — | 3 | 8.96 | 35 | 0 | 0 |
| 4.48 | — | 3 | 2.24 | 0 | 100 | 100 |
| 4.48 | — | 3 | 8.96 | 30 | 100 | 100 |
| — | 0.56 | 3 | 2.24 | 40 | 25 | 85 |
| — | 0.56 | 3 | 8.96 | 40 | 100 | 80 |
| 4.48 | 0.56 | 3 | 2.24 | 60 | 100 | 100 |
| 4.48 | 0.56 | 3 | 8.96 | 40 | 100 | 100 |
| — | — | 5 | 8.96 | 0 | 0 | 0 |
| 4.48 | — | 5 | 2.24 | 60 | 100 | 100 |
| 4.48 | — | 5 | 8.96 | 25 | 100 | 100 |
| — | 0.56 | 5 | 2.24 | 60 | 100 | 100 |
| — | 0.56 | 5 | 8.96 | 20 | 90 | 85 |
| 4.48 | 0.56 | 5 | 2.24 | 90 | 100 | 100 |
| 4.48 | 0.56 | 5 | 8.96 | 55 | 100 | 100 |
| — | — | 4 | 8.96 | 15 | 0 | 0 |
| 4.48 | — | 4 | 2.24 | 35 | 100 | 100 |
| 4.48 | — | 4 | 8.96 | 35 | 100 | 100 |
| — | 0.56 | 4 | 2.24 | 10 | 0 | 75 |

TABLE 5-continued

| Herbicide | | | | | | |
|---|---|---|---|---|---|---|
| Acetochlor Rate | No. 4 (Kg/Ha) | Antidote No. | Antidote Kg/Ha | % Injury Corn | % Injury RRP | % Injury BYG |
| — | 0.56 | 4 | 8.96 | 5 | 30 | 85 |
| 4.48 | 0.56 | 4 | 2.24 | 50 | 100 | 100 |
| 4.48 | 0.56 | 4 | 8.96 | 35 | 100 | 100 |
| — | — | 9 | 8.96 | 0 | 100 | 75 |
| 4.48 | — | 9 | 2.24 | 55 | 100 | 100 |
| 4.48 | — | 9 | 8.96 | 10 | 100 | 100 |
| — | 0.56 | 9 | 2.24 | 10 | 20 | 80 |
| — | 0.56 | 9 | 8.96 | 20 | 90 | 85 |
| 4.48 | 0.56 | 9 | 2.24 | 50 | 100 | 100 |
| 4.48 | 0.56 | 9 | 8.96 | 60 | 100 | 100 |
| — | — | 13 | 8.96 | 0 | 100 | 0 |
| 4.48 | — | 13 | 2.24 | 5 | 100 | 100 |
| 4.48 | — | 13 | 8.96 | 0 | 100 | 100 |
| — | 0.56 | 13 | 2.24 | 30 | 15 | 65 |
| — | 0.56 | 13 | 8.96 | 20 | 0 | 95 |
| 4.48 | 0.56 | 13 | 2.24 | 65 | 100 | 100 |
| 4.48 | 0.56 | 13 | 8.96 | 35 | 100 | 100 |
| — | — | 18 | 8.96 | 0 | 100 | 90 |
| 4.48 | — | 18 | 2.24 | 20 | 100 | 100 |
| 4.48 | — | 18 | 8.96 | 0 | 100 | 100 |
| — | 0.56 | 18 | 2.24 | 5 | 25 | 70 |
| — | 0.56 | 18 | 8.96 | 20 | 85 | 85 |
| 4.48 | 0.56 | 18 | 2.24 | 25 | 100 | 100 |
| 4.48 | 0.56 | 18 | 8.96 | 10 | 100 | 100 |
| — | — | 19 | 8.96 | 0 | 100 | 85 |
| 4.48 | — | 19 | 2.24 | 0 | 100 | 100 |
| 4.48 | — | 19 | 8.96 | 10 | 100 | 100 |
| — | 0.56 | 19 | 2.24 | 15 | 100 | 85 |
| — | 0.56 | 19 | 8.96 | 15 | 10 | 15 |
| 4.48 | 0.56 | 19 | 2.24 | 25 | 100 | 100 |
| 4.48 | 0.56 | 19 | 8.96 | 5 | 100 | 100 |

Overall, Antidote No. 19 was the most active, followed closely by Antidote No. 18. These antidotes both reduced injury to corn by combinations of 4.48 kg/ha of acetochlor and 0.56 kg/ha of Herbicide No. 4 (imazethapyr) from 92% to 25% at 2.24 kg/ha.

EXAMPLE 10

This test was conducted to evaluate the antidotal (safening) effect of a number of antidotes against combinations of imazethapyr and metolachlor in corn in the presence of the weeds redroot pigweed (RRP) and barnyardgrass (BYG).

The test procedure her was the same as that described in Example 9. Percent injury values to the plants treated with herbicide formulations containing no antidote represent averages of three replications, while percent injuries resulting from antidote-containing formulations are based on one replicate. Test results are shown in Table 6.

TABLE 6

| Herbicide | | | | | | |
|---|---|---|---|---|---|---|
| Metolachlor Rate | No. 4 (Kg/Ha) | Antidote No. | Antidote Kg/Ha | % Injury Corn | % Injury RRP | % Injury BYG |
| 8.96 | — | — | — | 40 | 90 | 100 |
| — | 0.56 | — | — | 88 | 75 | 100 |
| 8.96 | 0.56 | — | — | 95 | 100 | 100 |
| — | — | 1 | 8.96 | 0 | 0 | 0 |
| 8.96 | — | 1 | 2.24 | 0 | 90 | 100 |
| 8.96 | — | 1 | 8.96 | 5 | 100 | 100 |
| — | 0.56 | 1 | 2.24 | 85 | 80 | 100 |
| — | 0.56 | 1 | 8.96 | 75 | 85 | 100 |
| 8.96 | 0.56 | 1 | 2.24 | 90 | 100 | 100 |
| 8.96 | 0.56 | 1 | 8.96 | 90 | 100 | 100 |
| — | — | 22 | 8.96 | 0 | 0 | 0 |
| 8.96 | — | 22 | 2.24 | 0 | 100 | 100 |
| 8.96 | — | 22 | 8.96 | 0 | 100 | 100 |
| — | 0.56 | 22 | 2.24 | 95 | 60 | 95 |
| — | 0.56 | 22 | 8.96 | 95 | 75 | 100 |

TABLE 6-continued

| Herbicide | | | | | | |
|---|---|---|---|---|---|---|
| Metolachlor Rate | No. 4 (Kg/Ha) | Antidote No. | Antidote Kg/Ha | % Injury Corn | % Injury RRP | % Injury BYG |
| 8.96 | 0.56 | 22 | 2.24 | 95 | 100 | 100 |
| 8.96 | 0.56 | 22 | 8.96 | 85 | 100 | 100 |
| — | — | 24 | 8.96 | 0 | 0 | 0 |
| 8.96 | — | 24 | 2.24 | 20 | 100 | 100 |
| 8.96 | — | 24 | 8.96 | 10 | 100 | 100 |
| — | 0.56 | 24 | 2.24 | 75 | 65 | 100 |
| — | 0.56 | 24 | 8.96 | 65 | 55 | 20 |
| 8.96 | 0.56 | 24 | 2.24 | 80 | 95 | 100 |
| 8.96 | 0.56 | 24 | 8.96 | 80 | 100 | 100 |
| — | — | 4 | 8.96 | 0 | 0 | 0 |
| 8.96 | — | 4 | 2.24 | 0 | 100 | 100 |
| 8.96 | — | 4 | 8.96 | 0 | 95 | 100 |
| — | 0.56 | 4 | 2.24 | 75 | 60 | 100 |
| — | 0.56 | 4 | 8.96 | 75 | 65 | 95 |
| 8.96 | 0.56 | 4 | 2.24 | 95 | 100 | 100 |
| 8.96 | 0.56 | 4 | 8.96 | 90 | 100 | 100 |
| — | — | 5 | 8.96 | 5 | 100 | 60 |
| 8.96 | — | 5 | 2.24 | 15 | 100 | 100 |
| 8.96 | — | 5 | 8.96 | 25 | 100 | 100 |
| — | 0.56 | 5 | 2.24 | 75 | 90 | 95 |
| — | 0.56 | 5 | 8.96 | 50 | 100 | 100 |
| 8.96 | 0.56 | 5 | 2.24 | 70 | 100 | 100 |
| 8.96 | 0.56 | 5 | 8.96 | 80 | 100 | 100 |
| — | — | 7 | 8.96 | 0 | 100 | 0 |
| 8.96 | — | 7 | 2.24 | 0 | 100 | 100 |
| 8.96 | — | 7 | 8.96 | 25 | 100 | 100 |
| — | 0.56 | 7 | 2.24 | 80 | 100 | 100 |
| — | 0.56 | 7 | 8.96 | 65 | 100 | 100 |
| 8.96 | 0.56 | 7 | 2.24 | 90 | 100 | 100 |
| 8.96 | 0.56 | 7 | 8.96 | 75 | 100 | 100 |
| — | — | 9 | 8.96 | 0 | 0 | 30 |
| 8.96 | — | 9 | 2.24 | 0 | 100 | 100 |
| 8.96 | — | 9 | 8.96 | 0 | 100 | 100 |
| — | 0.56 | 9 | 2.24 | 70 | 100 | 100 |
| — | 0.56 | 9 | 8.96 | 80 | 100 | 100 |
| 8.96 | 0.56 | 9 | 2.24 | 80 | 100 | 100 |
| 8.96 | 0.56 | 9 | 8.96 | 80 | 100 | 100 |
| — | — | 13 | 8.96 | 50 | 0 | 0 |
| 8.96 | — | 13 | 2.24 | 0 | 95 | 100 |
| 8.96 | — | 13 | 8.96 | 0 | 100 | 100 |
| — | 0.56 | 13 | 2.24 | 75 | 85 | 95 |
| — | 0.56 | 13 | 8.96 | 65 | 65 | 95 |
| 8.96 | 0.56 | 13 | 2.24 | 90 | 100 | 100 |
| 8.96 | 0.56 | 13 | 8.96 | 75 | 100 | 100 |
| — | — | 18 | 8.96 | 0 | 50 | 85 |
| 8.96 | — | 18 | 2.24 | 0 | 100 | 100 |
| 8.96 | — | 18 | 8.96 | 0 | 100 | 100 |
| — | 0.56 | 18 | 2.24 | 80 | 80 | 95 |
| — | 0.56 | 18 | 8.96 | 80 | 95 | 95 |
| 8.96 | 0.56 | 18 | 2.24 | 95 | 100 | 100 |
| 8.96 | 0.56 | 18 | 8.96 | 85 | 100 | 100 |
| — | — | 19 | 8.96 | 10 | 0 | 0 |
| 8.96 | — | 19 | 2.24 | 5 | 95 | 100 |
| 8.96 | — | 19 | 8.96 | 0 | 95 | 100 |
| — | 0.56 | 19 | 2.24 | 50 | 95 | 95 |
| — | 0.56 | 19 | 8.96 | 75 | 85 | 95 |
| 8.96 | 0.56 | 19 | 2.24 | 95 | 100 | 100 |
| 8.96 | 0.56 | 19 | 8.96 | 60 | 100 | 100 |

Although injury to corn was in most instances severe, some safening was observed. For example, 8.96 kg/ha of Antidote No. 19 reduced herbicidal injury from 95% to 60% against a combination of 8.96 kg/ha of metolachlor and 0.56 kg/ha of imazethapyr. It was concluded that the test rates for these herbicides were too high due to their high unit activity and that increased antidote:-herbicide ratios would further enhance antidotal activity and crop plant protection.

EXAMPLE 11

This example illustrates the safening effect of several antidotes against a combination of Herbicide No. 5 (AC-263222) with metolachlor as the co-herbicide.

The procedure of this example was the same as described in the preceding example, including the crop and weeds and number of replications to obtain the stated percent injury average values. However, the application rate of the imidazolinone compound was reduced in view of other data indicating high unit activity for this class of compounds requiring smaller amounts thereof and/or higher antidote:herbicide ratios. Test data are shown in Table 7.

TABLE 7

| Herbicide | | | | | | |
|---|---|---|---|---|---|---|
| Metolachlor Rate | No. 5 (Kg/Ha) | Antidote No. | Antidote Kg/Ha | % Injury Corn | % Injury RRP | % Injury BYG |
| 8.96 | — | — | — | 52 | 100 | 100 |
| — | 0.56 | — | — | 28 | 75 | 95 |
| 8.96 | 0.56 | — | — | 93 | 100 | 100 |
| — | — | 1 | 8.96 | 10 | 0 | 0 |
| 8.96 | — | 1 | 2.24 | 5 | 95 | 100 |
| 8.96 | — | 1 | 8.96 | 10 | 90 | 100 |
| — | 0.56 | 1 | 2.24 | 25 | 65 | 95 |
| — | 0.56 | 1 | 8.96 | 15 | 80 | 85 |
| 8.96 | 0.56 | 1 | 2.24 | 85 | 100 | 100 |
| 8.96 | 0.56 | 1 | 8.96 | 90 | 100 | 100 |
| — | — | 22 | 8.96 | 0 | 0 | 0 |
| 8.96 | — | 22 | 2.24 | 0 | 95 | 100 |
| 8.96 | — | 22 | 8.96 | 0 | 95 | 100 |
| — | 0.56 | 22 | 2.24 | 40 | 85 | 95 |
| — | 0.56 | 22 | 8.96 | 60 | 85 | 95 |
| 8.96 | 0.56 | 22 | 2.24 | 65 | 100 | 100 |
| 8.96 | 0.56 | 22 | 8.96 | 30 | 100 | 100 |
| — | — | 24 | 8.96 | 0 | 0 | 0 |
| 8.96 | — | 24 | 2.24 | 0 | 100 | 100 |
| 8.96 | — | 24 | 8.96 | 15 | 100 | 100 |
| — | 0.56 | 24 | 2.24 | 10 | 100 | 90 |
| — | 0.56 | 24 | 8.96 | 40 | 55 | 90 |
| 8.96 | 0.56 | 24 | 2.24 | 45 | 100 | 100 |
| 8.96 | 0.56 | 24 | 8.96 | 30 | 100 | 100 |
| — | — | 4 | 8.96 | 5 | 0 | 0 |
| 8.96 | — | 4 | 2.24 | 15 | 85 | 100 |
| 8.96 | — | 4 | 8.96 | 10 | 95 | 100 |
| — | 0.56 | 4 | 2.24 | 20 | 60 | 80 |
| — | 0.56 | 4 | 8.96 | 25 | 45 | 85 |
| 8.96 | 0.56 | 4 | 2.24 | 60 | 100 | 100 |
| 8.96 | 0.56 | 4 | 8.96 | 60 | 100 | 100 |
| — | — | 5 | 8.96 | 5 | 100 | 0 |
| 8.96 | — | 5 | 2.24 | 25 | 95 | 100 |
| 8.96 | — | 5 | 8.96 | 20 | 95 | 100 |
| — | 0.56 | 5 | 2.24 | 10 | 70 | 70 |
| — | 0.56 | 5 | 8.96 | 15 | 90 | 90 |
| 8.96 | 0.56 | 5 | 2.24 | 25 | 100 | 100 |
| 8.96 | 0.56 | 5 | 8.96 | 0 | 85 | 0 |
| — | — | 7 | 8.96 | 0 | 85 | 0 |
| 8.96 | — | 7 | 2.24 | 30 | 95 | 100 |
| 8.96 | — | 7 | 8.96 | 5 | 100 | 100 |
| — | 0.56 | 7 | 2.24 | 60 | 100 | 100 |
| — | — | 7 | 8.96 | 25 | 100 | 100 |
| 8.96 | 0.56 | 7 | 2.24 | 45 | 100 | 100 |
| 8.96 | 0.56 | 7 | 8.96 | 25 | 100 | 100 |
| — | — | 9 | 8.96 | 0 | 90 | 15 |
| 8.96 | — | 9 | 2.24 | 0 | 100 | 100 |
| 8.96 | — | 9 | 8.96 | 0 | 100 | 100 |
| — | 0.56 | 9 | 2.24 | 0 | 70 | 80 |
| — | 0.56 | 9 | 8.96 | 10 | 90 | 90 |
| 8.96 | 0.56 | 9 | 2.24 | 75 | 100 | 100 |
| 8.96 | 0.56 | 9 | 8.96 | 75 | 100 | 100 |
| — | — | 13 | 8.96 | 0 | 0 | 0 |
| 8.96 | — | 13 | 2.24 | 10 | 100 | 100 |
| 8.96 | — | 13 | 8.96 | 5 | 100 | 100 |
| — | 0.56 | 13 | 2.24 | 5 | 50 | 80 |
| — | 0.56 | 13 | 8.96 | 15 | 90 | 90 |
| 8.96 | 0.56 | 13 | 2.24 | 60 | 100 | 100 |
| 8.96 | 0.56 | 13 | 8.96 | 60 | 100 | 100 |
| — | — | 18 | 8.96 | 0 | 0 | 0 |
| 8.96 | — | 18 | 2.24 | 5 | 95 | 100 |
| 8.96 | — | 18 | 8.96 | 5 | 100 | 100 |
| — | 0.56 | 18 | 2.24 | 15 | 85 | 90 |
| — | 0.56 | 18 | 8.96 | 10 | 95 | 90 |
| 8.96 | 0.56 | 18 | 2.24 | 70 | 100 | 100 |
| 8.96 | 0.56 | 18 | 8.96 | 65 | 100 | 100 |
| — | — | 19 | 8.96 | 10 | 0 | 0 |

TABLE 7-continued

| Herbicide | | | | | | |
|---|---|---|---|---|---|---|
| Metolachlor Rate | No. 5 (Kg/Ha) | Antidote No. | Antidote Kg/Ha | % Injury Corn | % Injury RRP | % Injury BYG |
| 8.96 | — | 19 | 2.24 | 10 | 95 | 100 |
| 8.96 | — | 19 | 8.96 | 0 | 100 | 100 |
| — | 0.56 | 19 | 2.24 | 0 | 80 | 80 |
| — | 0.56 | 19 | 8.96 | 35 | 85 | 90 |
| 8.96 | 0.56 | 19 | 2.24 | 10 | 100 | 100 |
| 8.96 | 0.56 | 19 | 8.96 | 40 | 100 | 100 |

Again, as in the preceding table, it is noted that while crop injury was severe with many combinations of the test herbicides, a number of antidotes were found to demonstrate safening effect against some of those combinations. Again, Antidote No. 19 was most efficacious, reducing herbicidal injury to corn from 93% to 10% at the 2.24 kg/ha rate against a combination of metolachlor at 8.96 kg/ha mixed with 0.56 kg/ha of AC-263222. Further adjustments in antidote-to-herbicide rates are indicated as desirable.

EXAMPLE 12

This example describes the antidotal effect of various antidotal compounds against imazaquin and metolachlor as co-herbicide.

The test procedure used in this example was the same as that described in Example 11. Test data for the experiments in this example are shown in Table 8.

TABLE 8

| Herbicide | | | | | | |
|---|---|---|---|---|---|---|
| Metolachlor Rate | No. 1 (Kg/Ha) | Antidote No. | Antidote Kg/Ha | % Injury Corn | % Injury RRP | % Injury BYG |
| 8.96 | — | — | — | 28 | 95 | 100 |
| — | — | — | — | 8 | 12 | 23 |
| 8.96 | 0.07 | — | — | 40 | 100 | 100 |
| — | — | 1 | 8.96 | 15 | 0 | 0 |
| 8.96 | — | 1 | 2.24 | 0 | 100 | 100 |
| 8.96 | — | 1 | 8.96 | 0 | 100 | 100 |
| — | 0.07 | 1 | 2.24 | 0 | 25 | 10 |
| — | 0.07 | 1 | 8.96 | 0 | 20 | 80 |
| 8.96 | 0.07 | 1 | 2.24 | 0 | 100 | 100 |
| 8.96 | 0.07 | 1 | 8.96 | 0 | 10 | 100 |
| — | — | 3 | 8.96 | 0 | 0 | 0 |
| 8.96 | — | 3 | 2.24 | 15 | 95 | 100 |
| 8.96 | — | 3 | 8.96 | 0 | 100 | 100 |
| — | 0.07 | 3 | 2.24 | 0 | 10 | 20 |
| — | 0.07 | 3 | 8.96 | 0 | 0 | 0 |
| 8.96 | 0.07 | 3 | 2.24 | 25 | 100 | 100 |
| 8.96 | 0.07 | 3 | 8.96 | 15 | 100 | 100 |
| — | — | 5 | 8.96 | 0 | 0 | 0 |
| 8.96 | — | 5 | 2.24 | 30 | 90 | 100 |
| 8.96 | — | 5 | 8.96 | 10 | 100 | 100 |
| — | 0.07 | 5 | 2.24 | 0 | 50 | 75 |
| — | 0.07 | 5 | 8.96 | 0 | 85 | 10 |
| 8.96 | 0.07 | 5 | 2.24 | 20 | 100 | 100 |
| 8.96 | 0.07 | 5 | 8.96 | 0 | 100 | 100 |
| — | — | 4 | 8.96 | 0 | 0 | 0 |
| 8.96 | — | 4 | 2.24 | 0 | 100 | 100 |
| 8.96 | — | 4 | 8.96 | 15 | 100 | 100 |
| — | 0.07 | 4 | 2.24 | 0 | 10 | 10 |
| — | 0.07 | 4 | 8.96 | 0 | 15 | 25 |
| 8.96 | 0.07 | 4 | 2.24 | 0 | 100 | 100 |
| 8.96 | 0.07 | 4 | 8.96 | 10 | 100 | 100 |
| — | — | 9 | 8.96 | 0 | 0 | 0 |
| 8.96 | — | 9 | 2.24 | 15 | 100 | 100 |
| 8.96 | — | 9 | 8.96 | 0 | 100 | 100 |
| — | 0.07 | 9 | 2.24 | 5 | 55 | 80 |
| — | 0.07 | 9 | 8.96 | 0 | 40 | 10 |
| 8.96 | 0.07 | 9 | 2.24 | 0 | 100 | 100 |
| 8.96 | 0.07 | 9 | 8.96 | 5 | 100 | 100 |
| — | — | 13 | 8.96 | 0 | 0 | 0 |
| 8.96 | — | 13 | 2.24 | 0 | 100 | 100 |
| 8.96 | — | 13 | 8.96 | 0 | 100 | 100 |
| — | 0.07 | 13 | 2.24 | 5 | 80 | 15 |

TABLE 8-continued

| Herbicide | | Antidote | | % Injury | | |
|---|---|---|---|---|---|---|
| Metolachlor Rate | No. 1 (Kg/Ha) | No. | Kg/Ha | Corn | RRP | BYG |
| — | 0.07 | 13 | 8.96 | 5 | 100 | 5 |
| 8.96 | 0.07 | 13 | 2.24 | 0 | 100 | 100 |
| 8.96 | 0.07 | 13 | 8.96 | 0 | 100 | 100 |
| — | — | 18 | 8.96 | 0 | 80 | 0 |
| 8.96 | — | 18 | 2.24 | 0 | 100 | 100 |
| 8.96 | — | 18 | 8.96 | 5 | 100 | 100 |
| — | 0.07 | 18 | 2.24 | 0 | 65 | 25 |
| — | 0.07 | 18 | 8.96 | 0 | 70 | 85 |
| 8.96 | 0.07 | 18 | 2.24 | 0 | 100 | 100 |
| 8.96 | 0.07 | 18 | 8.96 | 0 | 100 | 100 |
| — | — | 19 | 8.96 | 0 | 0 | 0 |
| 8.96 | — | 19 | 2.24 | 0 | 90 | 100 |
| 8.96 | — | 19 | 8.96 | 0 | 100 | 100 |
| — | 0.07 | 19 | 2.24 | 5 | 85 | 25 |
| — | 0.07 | 19 | 8.96 | 10 | 10 | 25 |
| 8.96 | 0.07 | 19 | 2.24 | 10 | 100 | 100 |
| 8.96 | 0.07 | 19 | 8.96 | 0 | 95 | 100 |

In the test of Example 12 the data in Table 8 show that good safening against the imazaquin/metolachlor combination while maintaining good weed control. This improved safening effect may be due in part to reduced rates of the high unit activity of imazaquin resulting in higher antidote:herbicide ratios.

EXAMPLE 13

In the test described in this example, an objective was to determine the antidotal effect of a variety of antidotes on the combination of imazaquin containing acetochlor as co-herbicide. The test procedure here was the same as in preceding examples, but using an application rate of 0.14 kg/ha of the imidazoline and 4.48 kg/ha of acetochlor. Test results are shown in Table 9.

TABLE 9

| Herbicide | | Antidote | | % Injury | | |
|---|---|---|---|---|---|---|
| Metolachlor Rate | No. 1 (Kg/Ha) | No. | Kg/Ha | Corn | RRP | BYG |
| 4.48 | — | — | — | 40 | 100 | 100 |
| — | 0.14 | — | — | 95 | 83 | 88 |
| 4.48 | 0.14 | — | — | 100 | 100 | 100 |
| — | — | 3 | 8.96 | 5 | 0 | 0 |
| 4.48 | — | 3 | 0.56 | 5 | 100 | 100 |
| 4.48 | — | 3 | 2.24 | 0 | 100 | 100 |
| 4.48 | — | 3 | 8.96 | 0 | 100 | 100 |
| — | 0.14 | 3 | 0.56 | 65 | 50 | 95 |
| — | 0.14 | 3 | 2.24 | 95 | 100 | 85 |
| — | 0.14 | 3 | 8.96 | 85 | 35 | 95 |
| 4.48 | 0.14 | 3 | 0.56 | 95 | 95 | 100 |
| 4.48 | 0.14 | 3 | 2.24 | 95 | 95 | 100 |
| 4.48 | 0.14 | 3 | 8.96 | 90 | 100 | 100 |
| — | — | 5 | 8.96 | 0 | 0 | 0 |
| 4.48 | — | 5 | 0.56 | 25 | 95 | 100 |
| 4.48 | — | 5 | 2.24 | 15 | 100 | 95 |
| 4.48 | — | 5 | 8.96 | 5 | 100 | 100 |
| — | 0.14 | 5 | 0.56 | 80 | 90 | 10 |
| — | 0.14 | 5 | 2.24 | 90 | 90 | 50 |
| — | 0.14 | 5 | 8.96 | 75 | 85 | 85 |
| 4.48 | 0.14 | 5 | 0.56 | 95 | 95 | 100 |
| 4.48 | 0.14 | 5 | 2.24 | 95 | 100 | 100 |
| 4.48 | 0.14 | 5 | 8.96 | 85 | 100 | 100 |
| — | — | 4 | 8.96 | 0 | 0 | 85 |
| 4.48 | — | 4 | 0.56 | 0 | 100 | 100 |
| 4.48 | — | 4 | 2.24 | 0 | 100 | 100 |
| 4.48 | — | 4 | 8.96 | 0 | 90 | 100 |
| — | 0.14 | 4 | 0.56 | 30 | 100 | 95 |
| — | 0.14 | 4 | 2.24 | 45 | 95 | 95 |
| — | 0.14 | 4 | 8.96 | 45 | 95 | 90 |
| 4.48 | 0.14 | 4 | 0.56 | 90 | 100 | 100 |
| 4.48 | 0.14 | 4 | 2.24 | 90 | 90 | 100 |

The data in Table 9 indicate high corn injury making antidote evaluation difficult. However, Antidote No. 19 was again the most active compound in the test, exhibiting moderate safening of the herbicidal combination of 4.48 kg/ha of acetochlor and 0.14 kg/ha of imazaquin from 100% to 65% to 0.56 kg/ha.

Herbicidal formulations of the types described above may be exemplified in several illustrative embodiments below.

| | Weight Percent |
|---|---|
| I. Suspension Concentrates | |
| A. Imazaquin | 16.0 |
| AD-67 | 16.0 |
| Nonylphenol ethoxylate 9.5 mole EO Sterox NJ | 5.8 |
| Sodium lignosulfonate (Reax 88B) | 4.2 |
| Water | 58.0 |
| | 100.0 |
| B. Imazapyr | 32.5 |
| Antidote No. 1 | 11.0 |
| Potassium salt of napthalene sulfonate formaldehyde condensate (DAXAD 11 g) | 3.0 |
| Nonylphenol ethoxylate 10 mole EO (Igepal CO-660) | 4.0 |
| Water | 49.5 |
| | 100.0 |
| C. AC-222293 | 10.0 |
| Antidote No. 4 | 15.0 |
| Sodium dioctyl sulfosuccinate Aerosol OT-B | 3.0 |
| Castor oil + 36 Ethylene oxide (FloMo 3G) | 4.0 |
| Methanol | 70.0 |
| | 100.0 |
| II. Suspoemulsions | |
| A. Imazethyr | 10.0 |
| AD-67 | 15.0 |
| Acetochlor | 20.0 |
| Calcium dodecylbenzene sulfonate/polyoxyethylene ethers blend (e.g., Atlox= 3437F) | 5.0 |
| Calcium dodecylbenzene sulfonate (FloMo 60H) | 2.0 |
| Sodium salt of a polymerized alkyl napthalene sulfonic acid Daxad 1G) | 3.0 |
| Water | 45.0 |
| | 100.0 |
| B. Imazethapyr | 20.0 |
| Antidote No. 1 | 25.0 |
| Metolachlor | 15.0 |
| Calcium dodecyl sulfonate/alkylaryl polyether alcohol blend | 4.0 |
| Sodium Lignosulfonate (Marasperse N-22) | 2.10 |
| Water | 34.0 |
| | 100.0 |
| C. AC-263222 | 15.0 |
| Antidote No. 19 | 11.25 |
| Metolachlor | 30.0 |
| Calcium dodecylbenzene sulfonate/polyoxyethylene ethers blend (Atlox ® 3437F) | 4.0 |
| Sodium dioctyl sulfosuccinate Aerosol OT | 3.0 |
| Water | 36.75 |
| | 100.0 |
| D. Imazaquin | 10.0 |
| Antidote No. 13 | 10.0 |
| Acetochlor | 25.0 |
| Atlox 3437F | 4.0 |
| Sodium salt of a condensed | 3.0 |

-continued

| | Weight Percent |
|---|---|
| napthalene sulfonic acid (Tamol SN) | |
| Water | 48.0 |
| | 100.0 |
| E. Imazaquin | 2.5 |
| Antidote No. 18 | 15.0 |
| Alachlor | 10.0 |
| Monochlorobenzene | 4.0 |
| Atlox 3437F | 4.0 |
| Sodium lignosulfonate (Reax 88B) | 3.0 |
| Water | 61.5 |
| | 100.0 |
| III. Liquid Concentrates | |
| A. AC-263222 | 10.0 |
| Antidote No. 9 | 20.0 |
| Xylene | 70.0 |
| | 100.0 |
| B. Imazethapyr | 25.0 |
| Antidote No. 13 | 25.0 |
| Dimethyl sulfoxide | 50.0 |
| | 100.0 |
| C. AC-222293 | 30.0 |
| Antidote No. 1 | 40.0 |
| N-methylpyrrolidone | 30.0 |
| | 100.0 |
| D. Imazapyr | 5.0 |
| Antidote No. 4 | 10.0 |
| Ethoxylated castor oil | 15.0 |
| Rhodamine B | .5 |
| Dimethylformamide | 69.5 |
| | 100.0 |
| E. Imazaquin Sodium salt | 5.0 |
| Acetochlor | 15.0 |
| Atlox 3437F | 5.0 |
| Water | 75.0 |
| | 100.0 |
| F. Imazapyr sodium salt | 10.0 |
| Antidote No. 19 | 20.0 |
| Metolachlor | 15.0 |
| Calcium dodecylsulfonate polyether alcohol blend | 4.0 |
| Water | 51.0 |
| | 100.0 |
| IV. Wettable Powders | |
| A. Imazaquin | 35.0 |
| Antidote No. 6 | 25.0 |
| Sodium lignosulfonate | 3.0 |
| Sodium N-methyl-N-oleyl-taurate | 1.0 |
| Amorphous silica (synthetic) | 36.0 |
| | 100.0 |
| B. AC-222293 | 15.0 |
| Antidote No. 2 | 20.0 |
| Sodium dioctyl sulfosuccinate | 2.75 |
| Calcium lignosulfonate | 1.25 |
| Amorphous silica synthetic | 51.00 |
| | 100.0 |
| C. AC-263222 | 10.0 |
| Antidote No. 4 | 15.0 |
| Sodium lignosulfonate | 2.0 |
| Sodium N-methyl-N-oleyl-taurate | 1.0 |
| Kaolinite clay | 72.0 |
| | 100.0 |
| V. Dusts | |
| A. Imazapyr | 2.0 |
| Antidote No. 5 | 5.0 |
| Attapulgite | 93.0 |
| | 100.0 |
| B. Imazethapyr | 10.0 |
| Antidote No. 18 | 30.0 |
| Montmorillonite | 60.0 |
| | 100.0 |
| C. Imazaquin | 15.0 |
| Antidote No. 18 | 15.0 |
| Bentonite | 70.0 |

-continued

| | Weight Percent |
|---|---|
| | 100.0 |
| D. Imazapyr | 2.0 |
| Antidote No. 19 | 10.0 |
| Diatomaceous earth | 78.0 |
| | 100.0 |
| VI. Granules | |
| A. Imazaquin | 8.0 |
| Antidote No. 13 | 16.0 |
| Granular attapulgite (20/40 mesh) | 76.0 |
| | 100.0 |
| B. Imazapyr | 12.0 |
| Antidote No. 15 | 15.0 |
| Diatomaceous earth 20/40 | 73.0 |
| | 100.0 |
| C. Imazethapyr | 5.0 |
| Antidote No. 20 | 10.0 |
| Bentonite (20/40) | 85.0 |
| | 100.0 |
| D. AC-222293 | 15.0 |
| Antidote No. 35 | 15.0 |
| Pyrophyllite (20/40) | 70.0 |
| | 100.0 |
| VII. Microcapsules | |
| A. Imazaquin | 5.0 |
| Acetochlor encapsulated in a polyurea shell wall | 16.0 |
| Antidote No. 19 | 20.0 |
| Reax ® C-21 | 5.0 |
| Water | 54.0 |
| | 100.0 |
| B. Imazapyr | 4.5 |
| Alachlor encapsulated in a polyurea shell wall | 15.0 |
| AD-67 | 15.0 |
| Treax, LTM ® | 3.0 |
| Water | 63.0 |
| | 100.0 |
| C. Imazethapyr | 10.0 |
| Metolachlor encapsulated in a polyurea shell wall | 12.0 |
| Antidote No. 13 | 25.0 |
| Reax C-21 | 1.0 |
| Water | 52.0 |
| | 100.0 |
| D. AC-222293 | 8.0 |
| Acetochlor encapsulated in a polyurea shell wall | 16.0 |
| Antidote No. 1 | 10.0 |
| Reax 88 ® B | 1.0 |
| Water | 55.0 |
| | 100.0 |

It will be understood by those skilled in the art that certain combinations of an imidazoline with a particular co-herbicide and/or antidote may be incompatible with each other in one or another liquid media, hence rendering some formulations unfeasible. For example, AC-222293 (active ingredient in ASSERT 2.5 LC herbicide) is not compatible with dicamba or amine formulations of 2,4-D or MCPA. Some of these co-herbicide combinations are known to be incompatible, but otherwise are readily determined without undue experimentation by those skilled in the art.

Suitable carriers for many of the herbicides and antidotes disclosed herein include common ketone, alcohol, hydrocarbon-based solvents, e.g., acetone, dimethyl sulfoxide, n-heptane, methanol, methylene chloride, cyclohexane, toluene, etc.

While the invention herein has been specifically exemplified with representative imidazolinone compounds of Formula I, by acetochlor, alachlor and metolachlor as representative of the compounds of Formula IV and by various dichloroacetamide antidotes such as AD-67 and the safener of Example 3 as representative of the compounds according to Formulae II and III respectively, as well as a multiplicity of other antidotes having a variety of chemical structures, it is to be understood that other compounds within the scope of the above formulae and other chemical classes are specifically contemplated as within the scope of this invention.

Examples of other herbicidal imidazolinone or imidazolidinone or -dione compounds within the purview of this invention which may be safened for use in various crops include the compounds disclosed in the following exemplary publications: EP Numbers 041623, 133310, 198552, 216360 and 298029; JA 1109-790, JA 1197-580A, J6 1183-272A, J6 3196-57OA; and Australian published Application No. AU 8661-073A, GB 2 172 886A, and U.S. Pat. Nos. 4,188,487, 4,297,128, 4,562,257, 4,554,013, 4,647,301, 4,638,068, 4,650,514, 4,709,036, 4,749,403, 4,749,404, 4,741,767, 4,776,876 and 4,798,619.

The above specifically mentioned herbicidal compounds used as co-herbicides herein are intended merely as exemplary of the classes of herbicides which they represent. However, it is expressly contemplated that many other herbicidal compounds analogous to those represented herein having a variety of equivalent radicals substituted on the central nucleus may similarly be safened to various crop plants to a greater or lesser extent with the antidotal compounds of this invention. For example, other α-haloacetanilide compounds useful as herbicides are described in U.S. Pat. Nos. 3,442,945, 3,547,620, 3,830,841, 3,901,768, 4,517,011, 4,601,745, 4,319,918, 3,586,496, 3,574,746 and 4,249,935.

Herbicidally-useful thiocarbamate compounds are described in U.S. Pat. Nos. 2,913,327, 3,330,643 and 3,330,821.

Other herbicidal pyridine compounds are described in U.S. Pat. No. 4,692,184 and copending U.S. Ser. No. 07/134,231 (U.S. Pat. No. 4,988,384) and U.S. Pat. No. 4,826,532, both of common assignment herewith.

Herbicidally-useful heterocycyl phenyl ethers (especially pyrazolyl aryl ethers) are described in U.S. Pat. No. 4,298,749 and copending U.S. Ser. Nos. 07/175,460 (abandoned), entitled "Substituted 3-(4-Nitrophenoxy) Pyrazoles and Their Use As Herbicides", of common assignment herewith.

Herbicidal diphenyl ethers and nitrophenyl ethers include 2,4-dichlorophenyl 4′-nitrophenyl ether ("nitrofen"), 2-chloro-1-(3′-ethoxy-4′-nitrophenoxy)-4-trifluoromethylbenzene ("Oxyfluorfen"), 2′,4′-dichlorophenyl 3-methoxy-4-nitrophenyl ether ("Chlormethoxynil"), methyl 2-[4′-(2″, 4″-dichlorophenoxy)-phenoxyl-propionate, N-(2′-phenoxyethyl)-2-[5′-(2″-chloro-4″-trifluoromethylphenoxy)-phenoxyl]-propionamide, 2-methoxyethyl 2-[nitro-5-(2-chloro-4-trifluoromethylphenoxy)-phenoxyl-propionate and 2-chloro-4-trifluoromethylphenyl 3′-oxazolin-2′-yl-4′-nitrophenylether.

Another generic class of agrichemicallyimportant herbicidal compounds specifically contemplated for use as co-herbicidal compounds in combination with the antidotal compounds of this invention are the ureas and sulfonylurea derivatives. Important herbicidal ureas include 1-(benzothiazol-2-yl)-1,3-dimethylurea; phenylureas, for example: 3-(3-chloro-p-tolyl)-1,1-dimethylurea ("chlorotoluron"), 1,1-dimethyl-3-(α,α,αtrifluoro-m-tolyl)urea ("fluometuron"), 3-(4-bromo3-chlorophenyl)-methoxy-1-methylurea ("chlorbromuron"), 3-(4-bromophenyl)-1-methoxy-1-methylurea ("metobromuron"), 3-(3,4-dichlorophenyl)-1-methoxy-1-methylurea ("linuron"), 3-(4-chlorophenyl)-1-methoxy-1-methylurea ("monolinuron"), 3-(3,4-dichlorophenyl)-1,1-dimethylurea ("diuron"), 3-(4-chlorophenyl)-1,1-dimethylurea ("monuron") and 3-(3-chloro-4-methoxyphenyl)-1,1-dimethylurea ("metoxuron");

Important herbicidal sulfonylureas specifically contemplated as useful as co-herbicides in compositions with the antidotal compounds of this invention include those disclosed in the following patents: U.S. Pat. Nos. 4,383,113, 4,127,405, 4,481,029, 4,514,212, 4,420,325, 4,638,004, 4,675,046, 4,681,620, 4,741,760, 4,723,123, 4,411,690, 4,718,937, 4,620,868, 4,668,277, 4,592,776, 4,666,508, 4,696,695, 4,731,446 and 4,668,279; EP Numbers 084224, 173312, 190105, 256396, 264021, 264672, 142152, 244847, 176304, 177163, 187470, 187489, 184385, 232067, 234352, 189069, 224842, 249938, 246984 and 246984 and German Offen. DE 3,618,004.

Among the herbicidal sulfonylureas disclosed in one or more of the above patents which are of particular interest are mentioned the species N-[(4-methoxy-6-methylpyrimidin-2-yl)aminocarbonyl]-3-chloro-4-methoxycarbonyl-1-methylpyrazole-5-sulfonamide, N-[(4,6-dimethoxypyrimidin-2-yl)aminocarbonyl]3-chloro-4-methoxycarbonyl-1-methylpyrazole-5-sulfonamide N-[(4-methoxy-6-methylpyrimidin-2-yl)aminocarbonyl]-3-chloro-4-ethoxycarbonyl-1-methylpyrazole5-sulfonamide, N-[(4,6-dimethoxypyrimidin-2-yl)aminocarbonyl]-3-chloro-4-ethoxycarbonyl-1-methylpyrazole-5-sulfonamide N-[(4-methoxy-6-methylpyrimidin-2-yl)aminocarbonyl]-3-bromo-4-ethoxycarbonyl-1-methylpyrazole-5-sulfonamide, N-[(4,6-dimethoxypyrimidin-2-yl)aminocarbonyl]-3-bromo-4-ethoxycarbonyl-1-methylpyrazole-5-sulfonamide and N-(methoxycarbonyl-1-phenyl sulfonylN′-(bis-difluoromethoxy pyrimidin-2-yl)urea.

Still other classes of herbicidal compounds contemplated for combination with imidazolinone derivatives and the antidotes of this invention include the following representative species:

Triazines and triazinones: 2,4-bis-(isopropylamino)-6-methylthio-1,3,5-triazine ("prometryn"), 2,4-bis(ethylamino)-6-methylthio-1,3,5-triazine ("simetryn"), 2-(1′,2′-dimethylpropylamino)-4-ethylamino-6-methylthio-1,3,5-triazine ("dimethametryn"), 2-chloro-4,6-bis-(ethylamino)-1,3,5-triazine ("simazine"), 2-tert-butylamino-4-chloro-6-ethylamino-1,3,5-triazine ("terbuthylazine"), 2-tert-butylamino-4-ethylamino6-methoxy-1,3,5-triazine ("terbumeton"), 2-tert-butylamino-4-ethylamino-6-methylthio-1,3,5-triazine ("terbutryn"), 2-ethylamino-4-isopropylamino-6-methylthio-1,3,5-triazine ("ametryn") and 3,4-bis(methylamino)-6-tert-butyl-4,4-dihydro-1,2,4-triazin5-one.

Oxadiazolones: 5-tert-butyl-3-(2′,4′-dichloro-5′-isopropoxyphenyl)-1,3,4-oxadiazol-2-one ("Oxadiazon").

Phosphates: S-2-methylpiperidinocarbonylmethyl O,O-dipropyl phosphorodithioate ("Piperophos").

Pyrazoles: 1,3-dimethyl-4-(2′,4′-dichlorobenzolyl)-5-(4′-tolylsulfonyloxy)-pyrazole.

Also α-(phenoxyphenoxy)-propionic acid derivatives and a-pyridyl-2-oxyphenoxy)-propionic acid derivatives.

In addition to the antidotal compounds exemplified herein, other representative antidotal compounds according to Formula II are expressly disclosed in various patents, e.g., U.S. Pat. Nos. 3,959,304, 4,072,688, 4,137,070, 4,124,372, 4,124,376, 4,483,706, 4,636,244, 4,033,756, 4,708,735, 4,256,481, 4,199,506, 4,251,261, 4,070,389, 4,231,783, 4,269,775, 4,152,137 and 4,294,764, and EP Nos. 0253291, 0007588, 0190105, 0229649, 16618 and W. German Patent Application Nos. 28 28 222, 28 28 293.1, and 29 30 450.5, South African Patent No. 82/7681, and PRC Application No. 102 879-87.

As will be appreciated by those skilled in the art, the practice of this invention comprises the use of the antidotal compounds disclosed and claimed herein with any herbicidally-active imidazolinone compound which may optionally be combined with co-herbicides from many different classes of chemistry. Obviously, the above listings of exemplary compounds is not intended to be exhaustive, but representative. Again, as noted earlier herein, it is expected that not every combination of herbicide and antidote will result in safening of all crops, but is within the skill of the art to test any given herbicide with an invention antidote in plant screens of any spectrum of plants and note the results.

The foregoing embodiments illustrate that the combinations of herbicide and antidote of this invention are useful in controlling weeds while reducing herbicidal injury to crop plants under greenhouse and field test conditions.

In field applications, the herbicide, antidote, or a mixture thereof, may be applied to the plant locus without any adjuvants other than a solvent. Usually, the herbicide, antidote, or a mixture thereof, is applied in conjunction with one or more adjuvants in liquid or solid form. Compositions or formulations containing mixtures of an appropriate herbicide(s) and antidote usually are prepared by admixing the herbicide and antidote with one or more adjuvants such as diluents, solvents, extenders, carriers, conditioning agents, water, wetting agents, dispersing agents, or emulsifying agents, or any suitable combination of these adjuvants. These mixtures may be in the form of emulsifiable concentrates, microencapsulates, particulate solids, granules of varying particle size, e.g., water-dispersible or water-soluble granules or larger dry granules, pellets, wettable powders, dusts, solutions, aqueous dispersions, or emulsions.

Examples of suitable adjuvants are finely-divided solid carriers and extenders including talcs, clays, pumice, silica, diatomaceous earth, quartz, Fuller's earth, sulfur, powdered cork, powdered wood, walnut flour, chalk, tobacco dust, charcoal, and the like. Typical liquid diluents include Stoddard's solvent, acetone, methylene chloride, alcohols, glycols, ethyl acetate, benzene, and the like. Liquids and wettable powders usually contain as a conditioning agent one or more surface-active agents in amounts sufficient to make a composition readily dispersible in water or in oil. The term "surface-active agent" includes wetting agents, dispersing agents, suspending agents, and emulsifying agents. Typical surface-active agents are mentioned in U.S. Pat. No. 2,547,724.

Compositions of this invention generally contain from about 5 to 95 parts herbicide-and-antidote, about 1 to 50 parts surface-active agent, and about 4 to 94 parts solvent, all parts being by weight based on the total weight of the composition.

Application of the herbicide, antidote, or mixture thereof, can be carried out by conventional techniques utilizing, for example, hand-carried or tractor-mounted spreaders, power dusters, boom and hand sprayers, spray dusters, and granular applicators. If desired, application of the compositions of the invention to plants can be accomplished by incorporating the compositions in the soil or other media.

The crop may be protected by treating the crop seed with an effective amount of antidote prior to planting. Generally, smaller amounts of antidote are required to treat such seeds. A weight ratio of as little as 0.6 parts of antidote per 1000 parts of seed may be effective. The amount of antidote utilized in treating the seed may be increased if desired. Generally, however, a weight ratio of antidote-to-seed weight may range from 0.1 to 10.0 parts of antidote per 1000 parts of seed. Since only a very small amount of active antidote is usually required for the seed treatment, the compound preferably is formulated as an organic solution, powder, emulsifiable concentrate, water solution, or flowable formulation, which can be diluted with water by the seed treater for use in seed treating apparatus. Under certain conditions, it may be desirable to dissolve the antidote in an organic solvent or carrier for use as a seed treatment or the pure compound alone may be used under properly controlled conditions.

For antidote seed-coating or for antidotes applied to soil in granular or liquid formulations, suitable carriers may be either solids, such as talc, sand, clay, diatomaceous earth, sawdust, calcium carbonate, and the like, or liquids, such as water, kerosene, acetone, benzene, toluene, xylene, and the like, in which the active antidote may be either dissolved or dispersed. Emulsifying agents are used to achieve a suitable emulsion if two immiscible liquids are used as a carrier. Wetting agents may also be used to aid in dispersing the active antidote in liquids used as a carrier in which the antidote is not completely soluble. Emulsifying agents and wetting agents are sold under numerous tradenames and trademarks and may be either pure compounds, mixtures of compounds of the same general groups, or they may be mixtures of compounds of different classes. Typical satisfactory surface active agents which may be used are alkali metal higher-alkylarylsulfonates such as sodium dodecylbenzenesulfonate and the sodium salts of alkylnaphthalenesulfonic acids, fatty alcohol sulfates such as the sodium salts of monoesters of sulfuric acid with n-aliphatic alcohols containing 8-18 carbon atoms, long-chain quaternary ammonium compounds, sodium salts of petroleum-derived alkylsulfonic acids, polyethylene sorbitan monooleate, alkylaryl polyether alcohols, water-soluble lignin sulfonate salts, alkali casein compositions, longchain alcohols usually containing 10-18 carbon atoms, and condensation products of ethylene oxide with fatty acids, alkylphenols, and mercaptans.

Although this invention has been described with respect to specific embodiments, the details of these embodiments are not to be construed as limitations. Various equivalents, changes, and modifications may be made without departing from the spirit and scope of this invention, and it is understood that such equivalent embodiments are part of this invention.

We claim:

1. Composition comprising (a) a herbicidally-effective amount of a compound according to Formula IA

IA

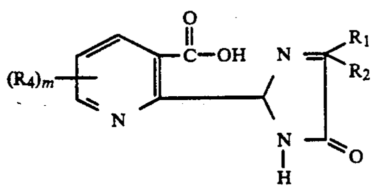

wherein $R_1$ and $R_2$ are $C_{1-4}$ alkyl;

$R_4$ is $C_{1-6}$ alkyl and m is 1 and (b) an antidotally-effective amount of a compound of Formula III

III

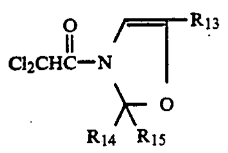

wherein $R_{13}$ is a saturated or unsaturated heterocyclic radical having $C_{5-10}$ ring atoms and containing O, N or S ring atoms and $R_{14}$ and $R_{15}$ are $C_{1-4}$ alkyl radicals.

2. Composition according to claim 1 wherein $R_1$ is methyl; $R_2$ is isopropyl; $R_4$ is ethyl and $R_{13}$ is furanyl.

3. Composition according to claim 2 wherein said herbicidal compound is imazethapyr and said antidotal compound is oxazolidine, 3-(dichloroacetyl)-2,2-dimethyl-5-(2-furanyl).

4. Composition according to claim 1 wherein said compound of Formula III is oxazolidine, 3-(dichloroacetyl)-2,2-dimethyl-5-(2-furanyl)-.

5. Composition according to claim 1 wherein said compound of Formula III is oxazolidine, 3-di-chloroacetyl-2,2-dimethyl-5-(2-thienyl)-.

6. Composition according to claim 1 wherein said compound of Formula III is pyridine, 3-[3-(dichloroacetyl)-2,2-dimethyl-5-oxazolidinyl]-.

7. Method for reducing phytotoxycity to crop plants due to herbicidal compounds of the formula

IA

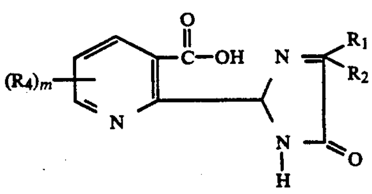

wherein $R_1$ and $R_2$ are $C_{1-4}$ alkyl;

$R_4$ is $C_{1-6}$ alkyl and m is 1, which comprises applying to the locus of the crop plant an antidotally-effective amount of a compound according to Formula III

III

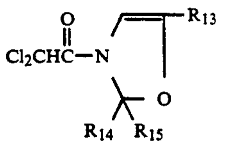

wherein $R_{13}$ is a saturated or unsaturated heterocyclic radical having $C_{5-10}$ ring atoms and containing O, N or S ring atoms and $R_{14}$ and $R_{15}$ are $C_{1-4}$ alkyl radicals.

8. Method according to claim 7 wherein $R_1$ is methyl; $R_2$ is isopropyl; $R_4$ is ethyl and $R_{13}$ is furanyl.

9. Method according to claim 8 wherein said herbicidal compound is imazethapyr and said antidotal compound is oxazolidine, 3-(dichloroacetyl)-2,2-dimethyl-5-(2-furanyl).

10. Method according to any of claims 7, 8 or 9 wherein said crop plant is corn.

11. Method according to claim 7 wherein said compound of Formula III is oxazolidine, 3-(dichloroacetyl)-2,2-dimethyl-5-(2-furanyl).

12. Composition comprising (a) a herbicidally-effective amount of 2-(4-isopropyl-4-methyl-5-oxo-2-imidazolin-2yl)-6-tetrahydrofurfuryloxy nicotinic acid or one or more compounds according to Formula IA

IA

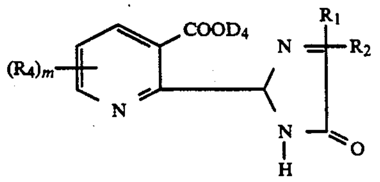

wherein $D_4$ is H, $C_{1-12}$ alkyl or an ammonium cation;

$R_1$ and $R_2$ are $C_{14}$ alkyl or haloalkyl;

$R_4$ is H, $C_{1-6}$ alkyl or two $R_4$ members may combine to form a $-(CH{=}CH)_m-$ or $-(CH_2)-$ radical;

m is 2 or 3;

n is 2–4; and (b) an antidotally-effective amount of oxazolidine, 3-(dichloroacetyl)-2,2-dimethyl-5-(2-furanyl)- or oxazolidine, 3-(dichloroacetyl)-2-(trichloromethyl)-.

13. Composition according to claim 12 wherein said compound 12 of Formula IA is imazaquin.

14. Composition according to claim 12 wherein said compound of Formula IA is imazethapyr.

15. Composition according to claim 12 wherein said compound of Formula IA is imazapyr.

16. Composition according to claim 12 wherein said compound of Formula IA is 3-pyridinecarboxylic acid, 2-[4,5-dihydro-4-methyl-4-(1-methylethyl)-5-oxo-1H-imidazol-2-yl]-5-methyl-.

17. Composition comprising a herbicidally-effective amount of imazethapyr or 2-(4-isopropyl-4-methyl-5-oxo-2-imidazolin-2-yl)-6-tetrahydrofurfuryloxy nicotinic acid and an antidotally-effective amount of oxazolidine, 3-(dichloroacetyl)-2,2-dimethyl-5-(2-furanyl)-, or oxazolidine, 3-(dichloroacetyl)-2-(trichloromethyl)-.

* * * * *